(12) United States Patent
Glassmeyer et al.

(10) Patent No.: US 12,129,594 B2
(45) Date of Patent: *Oct. 29, 2024

(54) ACTIVE AGENT-CONTAINING ARTICLES THAT EXHIBIT CONSUMER ACCEPTABLE ARTICLE IN-USE PROPERTIES

(71) Applicant: The Procter & Gamble Company, Cincinnati, OH (US)

(72) Inventors: Stephen Robert Glassmeyer, Cincinnati, OH (US); Michael Sean Pratt, St. Bernard, OH (US); Gregory Charles Gordon, Loveland, OH (US); Mark Robert Sivik, Mason, OH (US); Paul Thomas Weisman, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/203,885

(22) Filed: May 31, 2023

(65) Prior Publication Data
US 2023/0313445 A1 Oct. 5, 2023

Related U.S. Application Data

(63) Continuation of application No. 15/877,593, filed on Jan. 23, 2018, now Pat. No. 11,697,905.
(Continued)

(51) Int. Cl.
*D06M 13/00* (2006.01)
*A61K 8/02* (2006.01)
(Continued)

(52) U.S. Cl.
CPC .......... *D06M 13/005* (2013.01); *A61K 8/027* (2013.01); *B32B 5/02* (2013.01); *B32B 5/022* (2013.01); *B32B 5/22* (2013.01); *B32B 5/26* (2013.01); *C11D 17/044* (2013.01); *D04H 1/4209* (2013.01); *D04H 1/4374* (2013.01); *D04H 1/559* (2013.01); *D04H 3/007* (2013.01);
(Continued)

(58) Field of Classification Search
None
See application file for complete search history.

(56) References Cited

U.S. PATENT DOCUMENTS 3,066,347 A 12/1962 Vosbikian et al.
3,097,787 A 7/1963 Schur
(Continued)

FOREIGN PATENT DOCUMENTS

CN 1724725 A 1/2006
CN 103556250 A 2/2014
(Continued)

OTHER PUBLICATIONS

14509 Third Party Opposition for 18706884.6 dated May 16, 2023, 18 pages.
(Continued)

*Primary Examiner* — Shawn Mckinnon
(74) *Attorney, Agent, or Firm* — James E. Oehlenschlager

(57) ABSTRACT

Active agent-containing articles, for example fibrous structures, that exhibit consumer acceptable article in-use properties, such as article peel strength, flexibility, article dimensions, and/or dissolvability, and methods for making same are provided.

26 Claims, 15 Drawing Sheets

Related U.S. Application Data

(60) Provisional application No. 62/451,085, filed on Jan. 27, 2017.

(51) Int. Cl.

| | | |
|---|---|---|
| *B32B 5/02* | (2006.01) | |
| *B32B 5/22* | (2006.01) | |
| *B32B 5/26* | (2006.01) | |
| *C11D 17/04* | (2006.01) | |
| *D04H 1/4209* | (2012.01) | |
| *D04H 1/4374* | (2012.01) | |
| *D04H 1/559* | (2012.01) | |
| *D04H 3/007* | (2012.01) | |
| *D06M 16/00* | (2006.01) | |
| *D06M 17/00* | (2006.01) | |
| *D21H 27/00* | (2006.01) | |
| *D21H 27/30* | (2006.01) | |
| *D21H 27/32* | (2006.01) | |
| *D21H 27/38* | (2006.01) | |

(52) U.S. Cl.
CPC ............ *D06M 16/00* (2013.01); *D06M 17/00* (2013.01); *D21H 27/004* (2013.01); *D21H 27/30* (2013.01); *D21H 27/32* (2013.01); *D21H 27/38* (2013.01); *D06M 2200/00* (2013.01)

(56) References Cited

U.S. PATENT DOCUMENTS

| | | | |
|---|---|---|---|
| 3,823,816 A | 7/1974 | Controulis et al. |
| 3,994,771 A | 11/1976 | Morgan, Jr. et al. |
| 4,155,971 A | 5/1979 | Wysong |
| 4,188,304 A | 2/1980 | Clarke et al. |
| 4,555,354 A | 11/1985 | Clarke |
| 4,588,630 A | 5/1986 | Shimalla |
| 4,637,859 A | 1/1987 | Trokhan |
| 4,741,941 A | 5/1988 | Englebert |
| 4,762,738 A | 8/1988 | Keyes et al. |
| 4,776,455 A | 10/1988 | Anderson et al. |
| 4,806,261 A | 2/1989 | Ciallella et al. |
| 4,820,435 A | 4/1989 | Zafiroglu |
| 4,839,076 A | 6/1989 | Willman et al. |
| 4,876,023 A | 10/1989 | Dickenson |
| 5,053,270 A | 10/1991 | Mack |
| 5,160,654 A | 11/1992 | Falou et al. |
| 5,518,730 A | 5/1996 | Fuisz |
| 5,534,178 A | 7/1996 | Bailly et al. |
| 5,780,418 A | 7/1998 | Niinaka |
| 5,801,141 A | 9/1998 | Steber et al. |
| 6,270,623 B1 | 8/2001 | Goda et al. |
| 6,486,095 B1 | 11/2002 | Fujita et al. |
| 6,793,856 B2 | 9/2004 | Hartmann et al. |
| 6,818,606 B1 | 11/2004 | Hanada |
| 6,955,850 B1 | 10/2005 | Cabell et al. |
| 7,226,899 B2 | 6/2007 | Cole |
| 7,285,520 B2 | 10/2007 | Krzysik |
| 7,595,290 B2 | 9/2009 | Pounds et al. |
| 8,250,837 B2 | 8/2012 | Catlin et al. |
| 8,551,929 B2 | 10/2013 | Graham et al. |
| 8,754,022 B2 | 6/2014 | Zhang et al. |
| 8,980,816 B2 | 3/2015 | Dreher |
| 9,005,510 B2 | 4/2015 | Ishaque |
| 9,139,802 B2 | 9/2015 | Weisman et al. |
| 10,376,125 B2 | 8/2019 | Dreher et al. |
| 10,526,570 B2 | 1/2020 | Dreher et al. |
| 10,723,983 B2 | 7/2020 | Dreher et al. |
| 10,792,229 B2 | 10/2020 | Pratt et al. |
| 11,118,033 B2 | 9/2021 | Heinzman |
| 11,697,904 B2 | 7/2023 | Pratt et al. |
| 11,697,905 B2 | 7/2023 | Glassmeyer et al. |
| 11,697,906 B2 | 7/2023 | Weisman et al. |
| 2002/0025215 A1 | 2/2002 | Duden et al. |
| 2002/0077264 A1 | 6/2002 | Roberts et al. |
| 2002/0132746 A1 | 9/2002 | Desenna et al. |
| 2002/0169092 A1 | 11/2002 | Alexandre et al. |
| 2003/0049326 A1 | 3/2003 | Nimni |
| 2003/0065297 A1 | 4/2003 | Davis |
| 2003/0080150 A1 | 5/2003 | Cowan et al. |
| 2003/0203196 A1 | 10/2003 | Trokhan |
| 2004/0144681 A1 | 7/2004 | Wiedemann et al. |
| 2005/0217045 A1 | 10/2005 | Minkler et al. |
| 2005/0220828 A1 | 10/2005 | Ullom et al. |
| 2005/0250667 A1 | 11/2005 | Quellet et al. |
| 2005/0282725 A1 | 12/2005 | Dasque et al. |
| 2006/0005333 A1 | 1/2006 | Catalfamo et al. |
| 2006/0037724 A1 | 2/2006 | Akai et al. |
| 2006/0075253 A1 | 4/2006 | Sonkin et al. |
| 2006/0213801 A1 | 9/2006 | Karaoren |
| 2006/0243630 A1 | 11/2006 | Bourgoin et al. |
| 2007/0071537 A1 | 3/2007 | Reddy et al. |
| 2008/0004198 A1 | 1/2008 | Joinson |
| 2008/0132438 A1 | 6/2008 | Hoffman et al. |
| 2008/0160286 A1 | 7/2008 | Asrar et al. |
| 2008/0177241 A1 | 7/2008 | Hasse et al. |
| 2008/0242572 A1 | 10/2008 | Icht |
| 2009/0181587 A1 | 7/2009 | Kang |
| 2009/0214140 A1 | 8/2009 | Jacobson |
| 2009/0287034 A1 | 11/2009 | Siggelkow |
| 2009/0306277 A1 | 12/2009 | Goenner et al. |
| 2010/0018641 A1 | 1/2010 | Branham |
| 2010/0029377 A1 | 2/2010 | Canterbury et al. |
| 2010/0115708 A1 | 5/2010 | Caswell et al. |
| 2010/0158987 A1 | 6/2010 | Lehrke |
| 2010/0294678 A1 | 11/2010 | Arnold |
| 2010/0297377 A1 | 11/2010 | Mcneil et al. |
| 2011/0028373 A1 | 2/2011 | Fossum et al. |
| 2011/0033509 A1 | 2/2011 | Simon |
| 2011/0129510 A1 | 6/2011 | Liebmann |
| 2011/0135587 A1 | 6/2011 | Kinoshita et al. |
| 2011/0207646 A1 | 8/2011 | Baez et al. |
| 2011/0250256 A1 | 10/2011 | Hyun-oh et al. |
| 2011/0301070 A1 | 12/2011 | Ochomogo |
| 2012/0021026 A1 | 1/2012 | Glenn, Jr. |
| 2012/0027838 A1 | 2/2012 | Gordon et al. |
| 2012/0036733 A1 | 2/2012 | Dehn |
| 2012/0052036 A1 | 3/2012 | Glenn, Jr. |
| 2012/0052037 A1 | 3/2012 | Sivik et al. |
| 2012/0053103 A1 | 3/2012 | Sivik |
| 2012/0053106 A1 | 3/2012 | Labeque |
| 2012/0053107 A1 | 3/2012 | Labeque et al. |
| 2012/0053108 A1 | 3/2012 | Glenn, Jr. |
| 2012/0121316 A1 | 5/2012 | Brown et al. |
| 2012/0121669 A1 | 5/2012 | Fontana et al. |
| 2012/0121674 A1 | 5/2012 | Pedoja |
| 2012/0237576 A1 | 9/2012 | Gordon |
| 2013/0017421 A1 | 1/2013 | Onnerud et al. |
| 2013/0053293 A1 | 2/2013 | Dituro et al. |
| 2013/0142852 A1 | 6/2013 | Tojo et al. |
| 2013/0167305 A1 | 7/2013 | Weisman et al. |
| 2013/0171421 A1 | 7/2013 | Weisman |
| 2013/0172226 A1 | 7/2013 | Dreher et al. |
| 2013/0216789 A1 | 8/2013 | Kraus et al. |
| 2013/0256182 A1 | 10/2013 | Petrovicova et al. |
| 2013/0259918 A1 | 10/2013 | Lehrke |
| 2013/0273277 A1 | 10/2013 | Lee |
| 2013/0292273 A1 | 11/2013 | Sekiba |
| 2013/0302566 A1 | 11/2013 | Barnholtz et al. |
| 2014/0086965 A1 | 3/2014 | Dihora |
| 2014/0228194 A1 | 8/2014 | Kepinski et al. |
| 2014/0238889 A1 | 8/2014 | Sunder et al. |
| 2014/0271848 A1 | 9/2014 | Guido et al. |
| 2014/0336029 A1 | 11/2014 | Mirle et al. |
| 2014/0356521 A1 | 12/2014 | Oku et al. |
| 2014/0371411 A1 | 12/2014 | Dipietro |
| 2015/0004197 A1 | 1/2015 | Doerr et al. |
| 2015/0071572 A1 | 3/2015 | Dreher |
| 2015/0125574 A1 | 5/2015 | Arent et al. |
| 2015/0136636 A1 | 5/2015 | Sunder et al. |
| 2015/0136637 A1 | 5/2015 | Meier et al. |
| 2015/0158645 A1 | 6/2015 | Meier |
| 2015/0159082 A1 | 6/2015 | Lee et al. |

(56) References Cited

U.S. PATENT DOCUMENTS

| | | |
|---|---|---|
| 2015/0190543 A1 | 7/2015 | Marshall et al. |
| 2016/0101026 A1 | 4/2016 | Pratt et al. |
| 2016/0101204 A1 | 4/2016 | Lynch et al. |
| 2016/0251131 A1 | 9/2016 | Edwards |
| 2016/0251148 A1 | 9/2016 | Edwards |
| 2016/0258083 A1 | 9/2016 | Weisman et al. |
| 2016/0355950 A1 | 12/2016 | Young et al. |
| 2016/0374906 A1 | 12/2016 | Sivik |
| 2017/0233175 A1 | 8/2017 | Keuleers et al. |
| 2017/0275563 A1 | 9/2017 | Federle |
| 2017/0362124 A1 | 12/2017 | Sang et al. |
| 2018/0216285 A1 | 8/2018 | Pratt et al. |
| 2018/0216286 A1 | 8/2018 | Glassmeyer |
| 2018/0216287 A1 | 8/2018 | Weisman |
| 2018/0216288 A1 | 8/2018 | Weisman et al. |
| 2018/0362905 A1 | 12/2018 | Catlin et al. |
| 2019/0233781 A1 | 8/2019 | Huang et al. |
| 2019/0233970 A1 | 8/2019 | Reed |
| 2019/0233974 A1 | 8/2019 | Reed |
| 2020/0102524 A1 | 4/2020 | Dreher et al. |
| 2020/0115833 A1 | 4/2020 | Joseph et al. |
| 2020/0190446 A1 | 6/2020 | Sivik et al. |
| 2023/0058562 A1 | 2/2023 | Weisman et al. |
| 2024/0167197 A1 | 5/2024 | Reed |

FOREIGN PATENT DOCUMENTS

| | | |
|---|---|---|
| CN | 104039945 A | 9/2014 |
| DE | 202008007644 U1 | 10/2008 |
| DE | 202009017112 U1 | 4/2010 |
| EP | 0095335 A1 | 11/1983 |
| EP | 0178029 A2 | 4/1986 |
| EP | 0293139 A2 | 11/1988 |
| EP | 0904933 A2 | 3/1999 |
| EP | 1543763 A1 | 6/2005 |
| EP | 2003239 A1 | 12/2008 |
| EP | 2088187 A1 | 8/2009 |
| EP | 3549758 A1 | 10/2019 |
| GB | 1473147 A | 5/1977 |
| GB | 2254857 A | 10/1992 |
| JP | S61231210 A | 10/1986 |
| JP | S6339640 B2 | 8/1988 |
| JP | H01292185 A | 11/1989 |
| JP | H0453900 A | 2/1992 |
| JP | H06228876 A | 8/1994 |
| JP | H07329983 A | 12/1995 |
| JP | H0940023 A | 2/1997 |
| JP | H09216809 A | 8/1997 |
| JP | H108098 A | 1/1998 |
| JP | H1072600 A | 3/1998 |
| JP | H11206661 A | 8/1999 |
| JP | H11335303 A | 12/1999 |
| JP | 2000248466 A | 9/2000 |
| JP | 2000290899 A | 10/2000 |
| JP | 2001146629 A | 5/2001 |
| JP | 2004075672 A | 3/2004 |
| JP | 2006109984 A | 4/2006 |
| JP | 2008155566 A | 7/2008 |
| JP | 2010280679 A | 12/2010 |
| JP | 2012082568 A | 4/2012 |
| JP | 2012112052 A | 6/2012 |
| JP | 2017149695 A | 8/2017 |
| KR | 20100089367 A | 8/2010 |
| KR | 20110017263 A | 2/2011 |
| WO | 9220594 A1 | 11/1992 |
| WO | 9315701 A1 | 8/1993 |
| WO | 9516470 A1 | 6/1995 |
| WO | 9720098 A1 | 6/1997 |
| WO | 0010539 A1 | 3/2000 |
| WO | 0022218 A1 | 4/2000 |
| WO | 02056728 A1 | 7/2002 |
| WO | 03044153 A1 | 5/2003 |
| WO | 03084836 A1 | 10/2003 |
| WO | 2005035857 A3 | 11/2005 |
| WO | 2006136771 A1 | 12/2006 |
| WO | 2007090818 A1 | 8/2007 |
| WO | 2008020246 A2 | 2/2008 |
| WO | 2010065683 A1 | 6/2010 |
| WO | 2010065684 A1 | 6/2010 |
| WO | 2011053677 A1 | 5/2011 |
| WO | 2011153023 A1 | 12/2011 |
| WO | 2012003316 A1 | 1/2012 |
| WO | 2012003351 A2 | 1/2012 |
| WO | 2012003360 A2 | 1/2012 |
| WO | 2012003365 A1 | 1/2012 |
| WO | 2013103626 A1 | 7/2013 |
| WO | 2013103629 A1 | 7/2013 |
| WO | 2013103630 A1 | 7/2013 |
| WO | 2013126531 A1 | 8/2013 |
| WO | 2016057353 A1 | 4/2016 |
| WO | 2016057376 A1 | 4/2016 |
| WO | 2018140432 A1 | 8/2018 |
| WO | 2018140472 A1 | 8/2018 |
| WO | 2018140669 A1 | 8/2018 |
| WO | 2019147523 A1 | 8/2019 |
| WO | 2020123888 A1 | 6/2020 |

OTHER PUBLICATIONS

14709D EP Search Report and Written Opinion for 21206986.8 dated Apr. 5, 2022, 8 pages.
All Office Actions; U.S. Appl. No. 15/877,585, filed Jan. 23, 2018.
All Office Actions; U.S. Appl. No. 15/877,593, filed Jan. 23, 2018.
All Office Actions; U.S. Appl. No. 15/877,602, filed Jan. 23, 2018.
All Office Actions; U.S. Appl. No. 15/877,611, filed Jan. 23, 2018.
All Office Actions; U.S. Appl. No. 17/392,327, filed Aug. 3, 2021.
All Office Actions; U.S. Appl. No. 18/203,871, filed May 31, 2023.
All Office Actions; U.S. Appl. No. 18/203,895, filed May 31, 2023.
Collins Dictionary (https://www.collinsdictionary.com/dictionary/english/ply), page visited on Oct. 4, 2021 ). (Year: 2021).
https://www.merriam-webster.com/dictionary/handle; dated 2020; 2 pages.
International Search Report and Written Opinion; Application Ser. No. PCT/US2018/014948; dated Apr. 19, 2018; 15 pages.
Unpublished U.S. Appl. No. 18/203,871, filed May 31, 2023, to Michael Sean Pratt et. al.
Unpublished U.S. Appl. No. 18/203,895, filed May 31, 2023, to Paul Thomas Weisman et. al.
All Office Actions; U.S. Appl. No. 16/713,130, filed Dec. 13, 2019.
Anonymous, "Aversive-flacored Inkjet and laserjet printing fabric(s) to prevent injury to children", Research Disclosure, Mason Publications, Hamshire, GB, vol. 434, No. 35, dated Jun. 1, 2000, 2 pages.
Database WPI Week 199002, Thomson Scientific, London, GB;AN 1990-011767, XP002757711, 2 pages.
Database WPI Week 199437 Thomson Scientific , London, GB; AN 1994-300331, XP002757712, 2 pages.
Database WPI Week 200067, Thomson Scientific , London, GB;AN 2000-682013, XPO02757716 ; 3 pages.
Database WPI Week 200148, Thomson Scientific, London, GB;AN 2001-446066, XP002757710; 2 pages.
Database WPI Week 201079, Thomson Scientific , London, GB;AN 2O10-K40521, XP0O2757714; 2 pages.
Database WPI Week 201156 Thomson Scientific , London, GB;AN 2011-C10272, XPO02757713; 1 pages.
Database WPI Week 201242, Thomson Scientific , London, GB;AN 2012-G86009, XP002757715; 2 pages.
Lewis K, An assessment of four solvents for the recovery of 2-chlorobenzylidenemalononitrile and capsaicins from "CS" and "Pepper" type lachrymator sprays, and an examination of their persistence on cotton fabric. J Forensic Sci 2001 ; vol. 46, No. 2, pp. 352-355.
VaporTec, "Advantages of Continuous Flow Production", dated 2016; pp. 1-5.
All Office Actions; U.S. Appl. No. 18/430,852, filed Feb. 2, 2024.
All Office Actions; U.S. Appl. No. 16/702,663, filed Dec. 4, 2019.
All Office Actions; U.S. Appl. No. 18/751,747, filed Jun. 24, 2024.
All Office Actions; U.S. Appl. No. 18/751,784, filed Jun. 24, 2024.
All Office Actions; U.S. Appl. No. 18/751,942, filed Jun. 24, 2024.

(56) References Cited

OTHER PUBLICATIONS

U.S. Appl. No. 18/751,747, filed Jun. 24, 2024, to Stephen Robert Glassmeyer et al.
U.S. Appl. No. 18/751,784, filed Jun. 24, 2024, to Paul Thomas Weisman et al.
U.S. Appl. No. 18/751,942, filed Jun. 24, 2024, to Michael Sean Pratt et al.

ACTIVE AGENT-CONTAINING ARTICLES THAT EXHIBIT CONSUMER ACCEPTABLE ARTICLE IN-USE PROPERTIES

CROSS-REFERENCE TO RELATED APPLICATIONS

This application is a continuation of, and claims priority under 35 U.S.C. § 120 to, U.S. patent application Ser. No. 15/877,593, filed on Jan. 23, 2019, which claims the benefit, under 35 USC 119(e), to U.S. Provisional Patent Application No. 62/451,085, filed on Jan. 27, 2017; each of which are herein incorporated by reference in their entirety.

TECHNICAL FIELD

The present disclosure relates to active agent-containing articles, for example fibrous structures, more particularly to fibrous structures comprising one or more, for example, a plurality of fibrous elements comprising one or more active agents that are releasable from at least one of the fibrous elements, for example filaments and/or fibers, wherein the articles exhibit consumer acceptable article in-use properties, such as article peel strength, flexibility, dissolvability, and/or article dimensions, and methods for making same.

BACKGROUND

Articles, for example fibrous structures comprising one or more fibrous elements, such as filaments comprising one or more active agents that are releasable from at least one of the filaments, are known in the art. However, formulators of such articles have been unable to achieve consumer acceptable article in-use properties. For example, consumers desire that the articles exhibit sufficient structural integrity such that they do not prematurely fall apart or separate, especially for articles comprising two or more fibrous structure plies, during manufacturing, distribution in a package, upon dispensing by a consumer from a package, or in the consumer's hands prior to and/or during use by the consumer. In addition, consumers desire that the articles exhibit sufficient flexibility during use such that the articles are not too stiff, but not too flexible either, alone or in combination with one or more other consumer acceptable article in-use properties described herein. Further, consumers desire that the articles exhibit sufficient dissolution during use, whether it is in-hand dissolution for personal cleansing articles, such as shampoos, hair conditioners, body wash and/or hand soap, or in-machine dissolution for laundry and/or dishwashing articles, alone or in combination with one or more other consumer acceptable article in-use properties described herein.

In one example, the consumers desire that the article remains intact, doesn't separate or fall apart, especially if the article comprises two or more plies of fibrous structures comprising one or more fibrous elements comprising one or more active agents, and optionally including one or more particles, and thus exhibits sufficient intra-ply bond or inter-ply bond strength as measured according to the article's peel strengths alone or in combination with sufficient flexibility as measured according to the article's modified circular bend properties and/or sufficient dissolution as measured according to the article's hand dissolution value. In such a case, the consumer desires that the article exhibit sufficient peel strength and/or lap shear strength to mitigate and/or inhibit the article from prematurely (before desired by the consumer) coming apart during manufacturing, distribution in a package, upon dispensing by a consumer from a package, or in the consumer's hands prior to and/or during use. This desired peel strength and/or lap shear strength must be delivered without negatively impacting other consumer acceptable article in-use properties, for example the flexibility and/or the dissolution of the article.

One problem associated with current articles comprising one or more fibrous elements comprising one or more active agents present within the fibrous elements, especially articles comprising two or more plies comprising such fibrous elements is achieving sufficient plybond strength such that the article resists prematurely falling apart during manufacturing, upon adding a coating to the outer surface of one of the inner plies of the article, distribution in a package, upon dispensing by a consumer from a package, or in the consumer's hands prior to and/or during use a by a consumer without negatively impacting flexibility and/or dissolvability. Accordingly, there is a need for articles, for example articles comprising multi-ply fibrous structures comprising one or more fibrous elements, for example a plurality of fibrous elements, such as filaments comprising one or more active agents releasable from at least one of the filaments that exhibit consumer acceptable article in-use properties. Furthermore, with respect to use in the consumer's hands, there is a need for articles that exhibit consumer-preferred properties, such as article flexibility, ply bond strength, article dimensions, and overall consumer-preferred performance, such as creation of a smooth, silky, lathery solution in the consumer's hand before application to the surface and containment in the consumer's hand prior to and during initial dissolution.

SUMMARY

The present disclosure fulfills the need described above by providing an article, especially an article comprising two or more fibrous structure plies associated with one another such as by an adhesive and/or mechanical entanglement and/or thermal bonding and/or water moisture bonding having one or more fibrous elements comprising one or more active agents releasable from at least one of the fibrous elements wherein the article exhibits consumer acceptable article in-use properties, such as one or more dimensional requirements.

One solution to the problem identified above is to provide an article having one or more fibrous elements including one or more active agents present with the fibrous elements, especially articles including two or more plies having such fibrous elements is associating the fibrous elements and/or fibrous structure plies such that the article exhibits inter-ply, intra-ply, and/or whole 180° peel and lap shear properties as described herein while still providing acceptable in-use consumer-preferred properties, such as article dimensions, flexibility, and dissolvability, as described herein.

In one example of the present disclosure, an article having one or more fibrous elements wherein at least one of the fibrous elements includes one or more filament-forming materials and one or more active agents releasable from the fibrous elements, wherein the article exhibits an Average Inter-Ply Peak Peel Force of greater than 0.03 N as measured according to the Inter-Ply, Intra-Ply, and Whole 180° Peel Test Method, wherein the article has one or more of a width from about 1 cm to about 11 cm; a length from about 1 cm to about 20 cm; a height from about 0.01 mm to about 50.0 mm; a mass from about 0.25 g to about 50 g; a volume from about 0.25 cc to about 60 cc; and a density from about 0.05 g/cc to about 0.8 g/cc, is provided.

In another example of the present disclosure, an article having one or more fibrous elements wherein at least one of the fibrous elements includes one or more filament-forming materials and one or more active agents releasable from the fibrous elements, wherein the article exhibits an Average Intra-Ply Peak Peel Force of greater than 0.10 N as measured according to the Inter-Ply, Intra-Ply, and Whole 180° Peel Test Method, wherein the article has one or more of a width from about 1 cm to about 11 cm; a length from about 1 cm to about 20 cm; a height from about 0.01 mm to about 50.0 mm; a mass from about 0.25 g to about 50 g; a volume from about 0.25 cc to about 60 cc; and a density from about 0.05 g/cc to about 0.8 g/cc, is provided.

In another example of the present disclosure, an article having one or more fibrous elements wherein at least one of the fibrous elements includes one or more filament-forming materials and one or more active agents releasable from the fibrous elements, wherein the article exhibits an Average Whole 180° Peak Peel Force of greater than 0.03 N as measured according to the Inter-Ply, Intra-Ply, and Whole 180° Peel Test Method, wherein the article has one or more of a width from about 1 cm to about 11 cm; a length from about 1 cm to about 20 cm; a height from about 0.01 mm to about 50.0 mm; a mass from about 0.25 g to about 50 g; a volume from about 0.25 cc to about 60 cc; and a density from about 0.05 g/cc to about 0.8 g/cc, is provided.

In another example of the present disclosure, a multi-ply article having a first ply and a second ply, wherein at least one of the first and second plies includes an article including one or more filaments wherein at least one of the filaments includes one or more filament-forming materials and one or more active agents releasable from the filament, wherein the article exhibits an Average Inter-Ply Peak Peel Force of greater than 0.03 N as measured according to the Inter-Ply, Intra-Ply, and Whole 180° Peel Test Method, wherein the article has one or more of a width from about 1 cm to about 11 cm; a length from about 1 cm to about 20 cm; a height from about 0.01 mm to about 50.0 mm; a mass from about 0.25 g to about 50 g; a volume from about 0.25 cc to about 60 cc; and a density from about 0.05 g/cc to about 0.8 g/cc, is provided.

In another example of the present disclosure, a multi-ply article having a first ply and a second ply, wherein at least one of the first and second plies includes an article including one or more filaments wherein at least one of the filaments includes one or more filament-forming materials and one or more active agents releasable from the filament, wherein the article exhibits an Average Intra-Ply Peak Peel Force of greater than 0.10 N as measured according to the Inter-Ply, Intra-Ply, and Whole 180° Peel Test Method, wherein the article has one or more of a width from about 1 cm to about 11 cm; a length from about 1 cm to about 20 cm; a height from about 0.01 mm to about 50.0 mm; a mass from about 0.25 g to about 50 g; a volume from about 0.25 cc to about 60 cc; and a density from about 0.05 g/cc to about 0.8 g/cc, is provided.

In another example of the present disclosure, a multi-ply article having a first ply and a second ply, wherein at least one of the first and second plies includes an article including one or more filaments wherein at least one of the filaments includes one or more filament-forming materials and one or more active agents releasable from the filament, wherein the article exhibits an Average Whole 180° Peak Peel Force of greater than 0.03 N as measured according to the Inter-Ply, Intra-Ply, and Whole 180° Peel Test Method, wherein the article has one or more of a width from about 1 cm to about 11 cm; a length from about 1 cm to about 20 cm; a height from about 0.01 mm to about 50.0 mm; a mass from about 0.25 g to about 50 g; a volume from about 0.25 cc to about 60 cc; and a density from about 0.05 g/cc to about 0.8 g/cc, is provided.

The present disclosure provides an article including one or more filaments wherein at least one of the filaments includes one or more filament-forming materials and one or more article agents releasable from the filament, wherein the article exhibits a combination of superior plybond, flexibility/bending, lap shear, and/or hand dissolution properties compared to known articles.

DETAILED DESCRIPTION

Definitions

Figure 1:
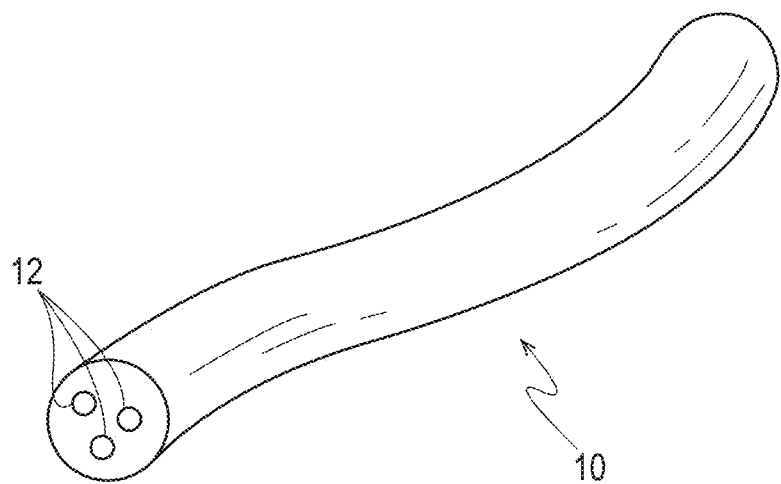
FIG. 1 is a schematic representation of an example of a fibrous element, in this case a filament, according to the present disclosure.

"Fibrous structure" as used herein means a structure that comprises one or more fibrous elements and optionally, one or more particles. In one example, a fibrous structure according to the present disclosure means an association of fibrous elements and optionally, particles that together form a structure, such as a unitary structure, capable of performing a function.

The fibrous structures of the present disclosure may be homogeneous or may be layered. If layered, the fibrous structures may comprise at least two and/or at least three and/or at least four and/or at least five layers, for example one or more fibrous element layers, one or more particle layers and/or one or more fibrous element/particle mixture layers. A layer may comprise a particle layer within the fibrous structure or between fibrous element layers within a fibrous structure. A layer comprising fibrous elements may sometimes be referred to as a ply. A ply may be a fibrous structure which may be homogeneous or layered as described herein.

In one example, a single-ply fibrous structure according to the present disclosure or a multi-ply fibrous structure comprising one or more fibrous structure plies according to the present disclosure may exhibit a basis weight of less than 5000 g/m$^2$ as measured according to the Basis Weight Test Method described herein. In one example, the single- or multi-ply fibrous structure according to the present disclosure may exhibit a basis weight of greater than 10 g/m$^2$ to about 5000 g/m$^2$ and/or greater than 10 g/m$^2$ to about 3000 g/m$^2$ and/or greater than 10 g/m$^2$ to about 2000 g/m$^2$ and/or greater than 10 g/m$^2$ to about 1000 g/m$^2$ and/or greater than 20 g/m$^2$ to about 800 g/m$^2$ and/or greater than 30 g/m$^2$ to about 600 g/m$^2$ and/or greater than 50 g/m$^2$ to about 500 g/m$^2$ and/or greater than 300 g/m$^2$ to about 3000 g/m$^2$ and/or greater than 500 g/m$^2$ to about 2000 g/m$^2$ as measured according to the Basis Weight Test Method.

In one example, the fibrous structure of the present disclosure is a "unitary fibrous structure."

"Unitary fibrous structure" as used herein is an arrangement comprising a plurality of two or more and/or three or more fibrous elements that are inter-entangled or otherwise associated with one another to form a fibrous structure and/or fibrous structure plies. A unitary fibrous structure of the present disclosure may be one or more plies within a multi-ply fibrous structure. In one example, a unitary fibrous structure of the present disclosure may comprise three or more different fibrous elements. In another example, a unitary fibrous structure of the present disclosure may comprise two or more different fibrous elements.

"Article" as used herein refers to a consumer use unit, a consumer unit dose unit, a consumer use saleable unit, a single dose unit, or other use form comprising a unitary fibrous structure and/or comprising one or more fibrous structures of the present disclosure.

"Fibrous element" as used herein means an elongate particulate having a length greatly exceeding its average diameter, i.e., a length to average diameter ratio of at least about 10. A fibrous element may be a filament or a fiber. In one example, the fibrous element is a single fibrous element rather than a yarn comprising a plurality of fibrous elements.

The fibrous elements of the present disclosure may be spun from a filament-forming compositions also referred to as fibrous element-forming compositions via suitable spinning process operations, such as meltblowing, spunbonding, electro-spinning, and/or rotary spinning.

The fibrous elements of the present disclosure may be monocomponent (single, unitary solid piece rather than two different parts, like a core/sheath bicomponent) and/or multicomponent. For example, the fibrous elements may comprise bicomponent fibers and/or filaments. The bicomponent fibers and/or filaments may be in any form, such as side-by-side, core and sheath, islands-in-the-sea and the like.

"Filament" as used herein means an elongate particulate as described above that exhibits a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.).

Filaments are typically considered continuous or substantially continuous in nature. Filaments are relatively longer than fibers. Non-limiting examples of filaments include meltblown and/or spunbond filaments. Non-limiting examples of polymers that can be spun into filaments include natural polymers, such as starch, starch derivatives, cellulose, such as rayon and/or lyocell, and cellulose derivatives, hemicellulose, hemicellulose derivatives, and synthetic polymers including, but not limited to polyvinyl alcohol and also thermoplastic polymer filaments, such as polyesters, nylons, polyolefins such as polypropylene filaments, polyethylene filaments, and biodegradable thermoplastic fibers such as polylactic acid filaments, polyhydroxyalkanoate filaments, polyesteramide filaments and polycaprolactone filaments.

"Fiber" as used herein means an elongate particulate as described above that exhibits a length of less than 5.08 cm (2 in.) and/or less than 3.81 cm (1.5 in.) and/or less than 2.54 cm (1 in.).

Fibers are typically considered discontinuous in nature. Non-limiting examples of fibers include staple fibers produced by spinning a filament or filament tow of the present disclosure and then cutting the filament or filament tow into segments of less than 5.08 cm (2 in.) thus producing fibers.

In one example, one or more fibers may be formed from a filament of the present disclosure, such as when the filaments are cut to shorter lengths (such as less than 5.08 cm in length). Thus, in one example, the present disclosure also includes a fiber made from a filament of the present disclosure, such as a fiber comprising one or more filament-forming materials and one or more additives, such as active agents. Therefore, references to filament and/or filaments of the present disclosure herein also include fibers made from such filament and/or filaments unless otherwise noted. Fibers are typically considered discontinuous in nature relative to filaments, which are considered continuous in nature.

"Filament-forming composition" and/or "fibrous element-forming composition" as used herein means a composition that is suitable for making a fibrous element of the present disclosure such as by meltblowing and/or spunbonding. The filament-forming composition comprises one or more filament-forming materials that exhibit properties that make them suitable for spinning into a fibrous element. In one example, the filament-forming material comprises a polymer. In addition to one or more filament-forming materials, the filament-forming composition may comprise one or more additives, for example one or more active agents. In addition, the filament-forming composition may comprise one or more polar solvents, such as water, into which one or more, for example all, of the filament-forming materials and/or one or more, for example all, of the active agents are dissolved and/or dispersed prior to spinning a fibrous element, such as a filament from the filament-forming composition.

In one example as shown in FIG. 1, a fibrous element, for example a filament 10 of the present disclosure made from a fibrous element-forming composition of the present disclosure is such that one or more additives 12, for example one or more active agents, may be present in the filament rather than on the filament, such as a coating composition comprising one or more active agents, which may be the same or different from the active agents in the fibrous elements and/or particles. The total level of fibrous element-forming materials and total level of active agents present in the fibrous element-forming composition may be any suitable amount so long as the fibrous elements of the present disclosure are produced therefrom.

In one example, one or more additives, such as active agents, may be present in the fibrous element and one or more additional additives, such as active agents, may be present on a surface of the fibrous element. In another example, a fibrous element of the present disclosure may comprise one or more additives, such as active agents, that are present in the fibrous element when originally made, but then bloom to a surface of the fibrous element prior to and/or when exposed to conditions of intended use of the fibrous element.

"Filament-forming material" and/or "fibrous element-forming material" as used herein means a material, such as a polymer or monomers capable of producing a polymer that exhibits properties suitable for making a fibrous element. In one example, the filament-forming material comprises one or more substituted polymers such as an anionic, cationic, zwitterionic, and/or nonionic polymer. In another example, the polymer may comprise a hydroxyl polymer, such as a polyvinyl alcohol ("PVOH"), a partially hydrolyzed polyvinyl acetate and/or a polysaccharide, such as starch and/or a starch derivative, such as an ethoxylated starch and/or acid-thinned starch, carboxymethylcellulose, hydroxypropyl cellulose, hydroxyethyl cellulose. In another example, the polymer may comprise polyethylenes and/or terephthalates. In yet another example, the filament-forming material is a polar solvent-soluble material.

"Particle" as used herein means a solid additive, such as a powder, granule, encapsulate, microcapsule, and/or prill.

In one example, the particle exhibits a median particle size of 2000 µm or less as measured according to the Median Particle Size Test Method described herein. In another example, the particle exhibits a median particle size of from about 1 µm to about 2000 µm and/or from about 1 µm to about 1600 µm and/or from about 1 µm to about 800 µm and/or from about 5 µm to about 500 µm and/or from about 10 µm to about 300 µm and/or from about 10 µm to about 100 µm and/or from about 10 µm to about 50 µm and/or from about 10 µm to about 30 µm as measured according to the Median Particle Size Test Method described herein. The shape of the particle can be in the form of spheres, rods, plates, tubes, squares, rectangles, discs, stars, fibers or have regular or irregular random forms.

"Active agent-containing particle" as used herein means a solid additive comprising one or more active agents. In one example, the active agent-containing particle is an active agent in the form of a particle (in other words, the particle comprises 100% active agent(s)). The active agent-containing particle may exhibit a median particle size of 2000 µm or less as measured according to the Median Particle Size Test Method described herein. In another example, the active agent-containing particle exhibits a median particle size of from about 1 µm to about 2000 µm and/or from about 1 µm to about 800 µm and/or from about 5 µm to about 500 µm and/or from about 10 µm to about 300 µm and/or from about 10 µm to about 100 µm and/or from about 10 µm to about 50 µm and/or from about 10 µm to about 30 µm as measured according to the Median Particle Size Test Method described herein. In one example, one or more of the active agents is in the form of a particle that exhibits a median particle size of 20 µm or less as measured according to the Median Particle Size Test Method described herein.

In one example of the present disclosure, the fibrous structure comprises a plurality of particles, for example active agent-containing particles, and a plurality of fibrous elements in a weight ratio of particles, for example active agent-containing particles to fibrous elements of 1:100 or greater and/or 1:50 or greater and/or 1:10 or greater and/or 1:3 or greater and/or 1:2 or greater and/or 1:1 or greater and/or 2:1 or greater and/or 3:1 or greater and/or 4:1 or greater and/or 5:1 or greater and/or 7:1 or greater and/or 8:1 or greater and/or 10:1 or greater and/or from about 10:1 to about 1:100 and/or from about 8:1 to about 1:50 and/or from about 7:1 to about 1:10 and/or from about 7:1 to about 1:3 and/or from about 6:1 to 1:2 and/or from about 5:1 to about 1:1 and/or from about 4:1 to about 1:1 and/or from about 3:1 to about 1.5:1.

In another example of the present disclosure, the fibrous structure comprises a plurality of particles, for example active agent-containing particles, and a plurality of fibrous elements in a weight ratio of particles, for example active agent-containing particles, to fibrous elements of from about 10:1 to about 1:1 and/or from about 8:1 to about 1.5:1 and/or from about 7:1 to about 2:1 and/or from about 6:1 to about 2.5:1.

In yet another example of the present disclosure, the fibrous structure comprises a plurality of particles, for example active agent-containing particles, and a plurality of fibrous elements in a weight ratio of particles, for example active agent-containing particles, to fibrous elements of from about 1:1 to about 1:100 and/or from about 1:15 to about 1:80, and/or from about 1:2 to about 1:60 and/or from about 1:3 to about 1:50 and/or from about 1:3 to about 1:40.

In another example, the fibrous structure of the present disclosure comprises a plurality of particles, for example active agent-containing particles, at a basis weight of greater than 1 g/m² and/or greater than 10 g/m² and/or greater than 20 g/m² and/or greater than 30 g/m² and/or greater than 40 g/m² and/or from about 1 g/m² to about 5000 g/m² and/or to about 3500 g/m² and/or to about 2000 g/m² and/or from about 1 g/m² to about 2000 g/m² and/or from about 10 g/m² to about 1000 g/m² and/or from about 10 g/m² to about 500 g/m² and/or from about 20 g/m² to about 400 g/m² and/or from about 30 g/m² to about 300 g/m² and/or from about 40 g/m² to about 200 g/m² as measured by the Basis Weight Test Method described herein. In one example, the fibrous structure comprises two or more layers of particles, for example active agent-containing particles, for example wherein each layer of particles is present at a basis weight of from about 1 g/m² to about 500 g/m². In one example, a plurality of particles is present in an article in two or more plies within a multi-ply article. In one example, a plurality of particles is present in an article in between two or more plies within a multi-ply article. In another example, a plurality of particles is present in an article as a particle layer within the article between two or more plies within a multi-ply article.

In another example, the fibrous structure of the present disclosure comprises a plurality of fibrous elements at a basis weight of greater than 1 g/m² and/or greater than 10 g/m² and/or greater than 20 g/m² and/or greater than 30 g/m² and/or greater than 40 g/m² and/or from about 1 g/m² to about 5000 g/m² and/or from about 1 g/m² to about 3000 g/m² and/or from about 10 g/m² to about 5000 g/m² and/or to about 3000 g/m² and/or to about 2000 g/m² and/or from about 20 g/m² to about 2000 g/m² and/or from about 30 g/m² to about 1000 g/m² and/or from about 30 g/m² to about 500 g/m² and/or from about 30 g/m² to about 300 g/m² and/or from about 40 g/m² to about 100 g/m² and/or from about 40 g/m² to about 80 g/m² as measured by the Basis Weight Test Method described herein. In one example, the fibrous structure comprises two or more layers wherein fibrous elements are present in at least one of the layers at a basis weight of from about 1 g/m² to about 500 g/m². In one example, a plurality of fibrous elements is present in an article in two or more plies within a multi-ply article.

"Additive" as used herein means any material present in the fibrous element of the present disclosure that is not a filament-forming material. In one example, an additive comprises an active agent. In another example, an additive comprises a processing aid. In still another example, an additive comprises a filler. In one example, an additive comprises any material present in the fibrous element that its absence from the fibrous element would not result in the fibrous element losing its fibrous element structure, in other words, its absence does not result in the fibrous element losing its solid form. In another example, an additive, for example an active agent, comprises a non-polymer material.

In another example, an additive may comprise a plasticizer for the fibrous element. Non-limiting examples of suitable plasticizers for the present disclosure include polyols, copolyols, polycarboxylic acids, polyesters and dimethicone copolyols. Examples of useful polyols include, but are not limited to, glycerin, diglycerin, propylene glycol, ethylene glycol, butylene glycol, pentylene glycol, cyclohexane dimethanol, hexanediol, 2,2,4-trimethylpentane-1,3-diol, polyethylene glycol (200-600), pentaerythritol, sugar alcohols such as sorbitol, manitol, lactitol and other mono- and polyhydric low molecular weight alcohols (e.g., C2-C8 alcohols); mono di- and oligo-saccharides such as fructose, glucose, sucrose, maltose, lactose, high fructose corn syrup solids, and dextrins, and ascorbic acid.

In one example, the plasticizer includes glycerin and/or propylene glycol and/or glycerol derivatives such as propoxylated glycerol. In still another example, the plasticizer is selected from the group consisting of glycerin, ethylene glycol, polyethylene glycol, propylene glycol, glycidol, urea, sorbitol, xylitol, maltitol, sugars, ethylene bisformamide, amino acids, and mixtures thereof In another example, an additive may comprise a rheology modifier, such as a shear modifier and/or an extensional modifier. Non-limiting examples of rheology modifiers include but not limited to polyacrylamide, polyurethanes and polyacrylates that may be used in the fibrous elements of the present disclosure. Non-limiting examples of rheology modifiers are commercially available from The Dow Chemical Company (Midland, MI).

In yet another example, an additive may comprise one or more colors and/or dyes that are incorporated into the fibrous elements of the present disclosure to provide a visual signal when the fibrous elements are exposed to conditions of intended use and/or when an active agent is released from the fibrous elements and/or when the fibrous element's morphology changes.

In still yet another example, an additive may comprise one or more release agents and/or lubricants. Non-limiting examples of suitable release agents and/or lubricants include fatty acids, fatty acid salts, fatty alcohols, fatty esters, sulfonated fatty acid esters, fatty amine acetates, fatty amide, silicones, aminosilicones, fluoropolymers, and mixtures thereof. In one example, the release agents and/or lubricants may be applied to the fibrous element, in other words, after the fibrous element is formed. In one example, one or more release agents/lubricants may be applied to the fibrous element prior to collecting the fibrous elements on a collection device to form a fibrous structure. In another example, one or more release agents/lubricants may be applied to a fibrous structure formed from the fibrous elements of the present disclosure prior to contacting one or more fibrous structures, such as in a stack of fibrous structures. In yet another example, one or more release agents/lubricants may be applied to the fibrous element of the present disclosure and/or fibrous structure comprising the fibrous element prior to the fibrous element and/or fibrous structure contacting a surface, such as a surface of equipment used in a processing system so as to facilitate removal of the fibrous element and/or fibrous structure and/or to avoid layers of fibrous elements and/or plies of fibrous structures of the present disclosure sticking to one another, even inadvertently. In one example, the release agents/lubricants comprise particulates.

In even still yet another example, an additive may comprise one or more anti-blocking and/or detackifying agents. Non-limiting examples of suitable anti-blocking and/or detackifying agents include starches, starch derivatives, crosslinked polyvinylpyrrolidone, crosslinked cellulose, microcrystalline cellulose, silica, metallic oxides, calcium carbonate, talc, mica, and mixtures thereof.

"Conditions of intended use" as used herein means the temperature, physical, chemical, and/or mechanical conditions that a fibrous element and/or particle and/or fibrous structure of the present disclosure is exposed to when the fibrous element and/or particle and/or fibrous structure is used for one or more of its designed purposes. For example, if a fibrous element and/or a particle and/or a fibrous structure comprising a fibrous element is designed to be used in a washing machine for laundry care purposes, the conditions of intended use will include those temperature, chemical, physical and/or mechanical conditions present in a washing machine, including any wash water, during a laundry washing operation. In another example, if a fibrous element and/or a particle and/or a fibrous structure comprising a fibrous element is designed to be used by a human as a shampoo for hair care purposes, the conditions of intended use will include those temperature, chemical, physical and/or mechanical conditions present during the shampooing of the human's hair. Likewise, if a fibrous element and/or a particle and/or a fibrous structure comprising a fibrous element is designed to be used in a dishwashing operation, by hand or by a dishwashing machine, the conditions of intended use will include the temperature, chemical, physical and/or mechanical conditions present in a dishwashing water and/or dishwashing machine, during the dishwashing operation.

"Active agent" as used herein means an additive that produces an intended effect in an environment external to a fibrous element and/or a particle and/or a fibrous structure comprising a fibrous element of the present disclosure, such as when the fibrous element and/or a particle and/or fibrous structure is exposed to conditions of intended use of the fibrous element and/or a particle and/or a fibrous structure comprising a fibrous element. In one example, an active agent comprises an additive that treats a surface, such as a hard surface (i.e., kitchen countertops, bath tubs, toilets, toilet bowls, sinks, floors, walls, teeth, cars, windows, mirrors, dishes) and/or a soft surface (i.e., fabric, hair, skin, carpet, crops, plants). In another example, an active agent comprises an additive that creates a chemical reaction (i.e., foaming, fizzing, effervescing, coloring, warming, cooling, lathering, disinfecting and/or clarifying and/or chlorinating, such as in clarifying water and/or disinfecting water and/or chlorinating water). In yet another example, an active agent comprises an additive that treats an environment (i.e., deodorizes, purifies, perfumes air). In one example, the active agent is formed in situ, such as during the formation of the fibrous element and/or particle containing the active agent, for example the fibrous element and/or particle may comprise a water-soluble polymer (e.g., starch) and a surfactant (e.g., anionic surfactant), which may create a polymer complex or coacervate that functions as the active agent used to treat fabric surfaces.

"Treats" as used herein with respect to treating a surface means that the active agent provides a benefit to a surface or environment. Treats includes regulating and/or immediately improving a surface's or environment's appearance, cleanliness, smell, purity and/or feel. In one example treating in reference to treating a keratinous tissue (for example skin and/or hair) surface means regulating and/or immediately improving the keratinous tissue's cosmetic appearance and/or feel. For instance, "regulating skin, hair, or nail (keratinous tissue) condition" includes: thickening of skin, hair, or nails (e.g., building the epidermis and/or dermis and/or sub-dermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair. Treats may include providing a benefit to fabrics like during a cleaning or softening in a laundry machine, providing a benefit to hair like during shampooing, conditioning, or coloring of hair, or providing a benefit to environments like a toilet bowl by cleaning or disinfecting it.

In another example, treating means removing stains and/or odors from fabric articles, such as clothes, towels, linens, and/or hard surfaces, such as countertops and/or dishware including pots and pans.

"Fabric care active agent" as used herein means an active agent that when applied to a fabric provides a benefit and/or improvement to the fabric. Non-limiting examples of benefits and/or improvements to a fabric include cleaning (for example by surfactants), stain removal, stain reduction, wrinkle removal, color restoration, static control, wrinkle resistance, permanent press, wear reduction, wear resistance, pill removal, pill resistance, soil removal, soil resistance (including soil release), shape retention, shrinkage reduction, softness, fragrance, anti-bacterial, anti-viral, odor resistance, and odor removal.

"Dishwashing active agent" as used herein means an active agent that when applied to dishware, glassware, pots, pans, utensils, and/or cooking sheets provides a benefit and/or improvement to the dishware, glassware, plastic items, pots, pans and/or cooking sheets. Non-limiting examples of benefits and/or improvements to the dishware, glassware, plastic items, pots, pans, utensils, and/or cooking sheets include food and/or soil removal, cleaning (for example by surfactants) stain removal, stain reduction, grease removal, water spot removal and/or water spot prevention, glass and metal care, sanitization, shining, and polishing.

"Hard surface active agent" as used herein means an active agent when applied to floors, countertops, sinks, windows, mirrors, showers, baths, and/or toilets provides a benefit and/or improvement to the floors, countertops, sinks, windows, mirrors, showers, baths, and/or toilets. Non-limiting examples of benefits and/or improvements to the floors, countertops, sinks, windows, mirrors, showers, baths, and/or toilets include food and/or soil removal, cleaning (for example by surfactants), stain removal, stain reduction, grease removal, water spot removal and/or water spot prevention, limescale removal, disinfection, shining, polishing, and freshening.

"Keratinous tissue active agent" as used herein means an active agent that may be useful for treating keratinous tissue (e.g., hair, skin, or nails) condition. For a hair care active agent, "treating" or "treatment" or "treat" includes regulating and/or immediately improving keratinous tissue cosmetic appearance and/or feel. For instance, "regulating skin, hair, or nail condition" includes: thickening of skin, hair, or nails (e.g., building the epidermis and/or dermis and/or sub-dermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair. Another example of keratinous tissue active agent may be an active agent used in the shampooing, conditioning, or dyeing of hair.

"Weight ratio" as used herein means the ratio between two materials on their dry basis. For example, the weight ratio of filament-forming materials to active agents within a fibrous element is the ratio of the weight of filament-forming material on a dry weight basis (g or %) in the fibrous element to the weight of additive, such as active agent(s) on a dry weight basis (g or %—same units as the filament-forming material weight) in the fibrous element. In another example, the weight ratio of particles to fibrous elements within a fibrous structure is the ratio of the weight of particles on a dry weight basis (g or %) in the fibrous structure to the weight of fibrous elements on a dry weight basis (g or %—same units as the particle weight) in the fibrous structure.

"Water-soluble material" as used herein means a material that is miscible in water. In other words, a material that is capable of forming a stable (does not separate for greater than 5 minutes after forming the homogeneous solution) homogeneous solution with water at ambient conditions.

"Ambient conditions" as used herein means 23° C.±1.0° C. and a relative humidity of 50%±2%.

"Weight average molecular weight" as used herein means the weight average molecular weight as determined using gel permeation chromatography according to the protocol found in Colloids and Surfaces A. Physico Chemical & Engineering Aspects, Vol. 162, 2000, pg. 107-121.

"Article dimensions," as used herein, refers to the length, width, height, mass, volume, density, and the like, of an article.

"Length," as used herein with respect to a fibrous element, means the length along the longest axis of the fibrous element from one terminus to the other terminus. If a fibrous element has a kink, curl or curves in it, then the length is the length along the entire path of the fibrous element from one terminus to the other terminus. With respect to dimensions of an article, "length" may be defined differently. For example, with respect to articles of irregular shape, the length refers to the maximum feret or caliper diameter, which is the longest distance between two parallel planes tangential to the boundary of the article. For a rectilinear-shaped article, for example, the length refers to the distance from one edge to an opposite edge. In one example, an average length can be provided by measuring ten substantially similar replicate articles, compiling an average of the ten individual article length measurements, and reporting the value to the nearest 0.01 cm, where the individual article length measurements can be taken by any appropriate instrument that is calibrated, NIST traceable, and capable of a measurements to the nearest 0.01 cm.

"Diameter" as used herein, with respect to a fibrous element, is measured according to the Diameter Test Method described herein. In one example, a fibrous element of the present disclosure exhibits a diameter of less than 100 µm and/or less than 75 µm and/or less than 50 µm and/or less than 25 µm and/or less than 20 µm and/or less than 15 µm and/or less than 10 µm and/or less than 6 µm and/or greater than 1 µm and/or greater than 3 µm.

"Width," as used herein with respect to dimensions of an article, may refer to the measurement according to its conventional definition. For a rectilinear-shaped article, for example, the width refers to the distance from one edge to an opposite edge. However, with respect to articles of irregular shape, the width refers to the maximum feret or caliper diameter, which is the longest distance between two parallel planes tangential to the boundary of the article. In one example, an average width can be provided by measuring ten substantially similar replicate articles, compiling an average of the ten individual article width measurements, and reporting the value to the nearest 0.01 cm, where the individual article width measurements can be taken by any appropriate instrument that is calibrated, NIST traceable, and capable of a measurements to the nearest 0.01 cm.

"Height," as used herein with respect to dimensions of an article, may refer to the measurement according to its conventional definition. The height, or thickness, of an article, for example, can be measured by the Thickness Test Method described herein.

"Volume," as used herein with respect to dimensions of an article, may refer to the measurement according to its conventional definition. For example, the volume of an article can be calculated by measuring a projected area of the article, as viewed orthogonally to a plane of the length and width of the article, and multiplying the area by the height of the article. In one example, an average volume can be provided by measuring ten substantially similar replicate articles, compiling an average of the ten individual article volume measurements, and reporting the value to the nearest 0.01 cc.

"Mass," as used herein with respect to an article, may refer to the measurement according to its conventional definition. For example, the mass of an article can be measured using a top loading analytical balance with a resolution of ±0.01 g, where the balance is protected from air drafts and other disturbances by a draft shield. After conditioning the article, the mass of the article can be measured to the nearest 0.01 g. In one example, an average mass can be provided by measuring ten substantially similar replicate articles, compiling an average of the ten individual article mass measurements, and reporting the value to the nearest 0.01 g.

"Density," as used herein with respect to an article, may refer to the measurement according to its conventional definition, such that the density may be calculated by dividing the mass of the article by its volume. In one example, the density can be reported to the nearest 0.01 g/cc.

"Triggering condition" as used herein in one example means anything, as an act or event, that serves as a stimulus and initiates or precipitates a change in the fibrous element and/or particle and/or fibrous structure of the present disclosure, such as a loss or altering of the fibrous element's and/or fibrous structure's physical structure and/or a release of an additive, such as an active agent therefrom. In another example, the triggering condition may be present in an environment, such as water, when a fibrous element and/or particle and/or fibrous structure of the present disclosure is added to the water. In other words, nothing changes in the water except for the fact that the fibrous element and/or fibrous structure of the present disclosure is added to the water.

"Morphology changes" as used herein with respect to a fibrous element's and/or particle's morphology changing means that the fibrous element experiences a change in its physical structure. Non-limiting examples of morphology changes for a fibrous element and/or particle of the present disclosure include dissolution, melting, swelling, shrinking, breaking into pieces, exploding, lengthening, shortening, and combinations thereof. The fibrous elements and/or particles of the present disclosure may completely or substantially lose their fibrous element or particle physical structure or they may have their morphology changed or they may retain or substantially retain their fibrous element or particle physical structure as they are exposed to conditions of intended use.

"By weight on a dry fibrous element basis" and/or "by weight on a dry particle basis" and/or "by weight on a dry fibrous structure basis" means the weight of the fibrous element and/or particle and/or fibrous structure, respectively, measured immediately after the fibrous element and/or particle and/or fibrous structure, respectively, has been conditioned in a conditioned room at a temperature of 23° C.±1.0° C. and a relative humidity of 50%±10% for 2 hours. In one example, by weight on a dry fibrous element basis and/or dry particle basis and/or dry fibrous structure basis means that the fibrous element and/or particle and/or fibrous structure comprises less than 20% and/or less than 15% and/or less than 10% and/or less than 7% and/or less than 5% and/or less than 3% and/or to 0% and/or to greater than 0% based on the dry weight of the fibrous element and/or particle and/or fibrous structure of moisture, such as water, for example free water, as measured according to the Water Content Test Method described herein.

"Total level" as used herein, for example with respect to the total level of one or more active agents present in the fibrous element and/or particle and/or fibrous structure, means the sum of the weights or weight percent of all of the subject materials, for example active agents. In other words, a fibrous element and/or particle and/or fibrous structure may comprise 25% by weight on a dry fibrous element basis and/or dry particle basis and/or dry fibrous structure basis of an anionic surfactant, 15% by weight on a dry fibrous element basis and/or dry particle basis and/or dry fibrous structure basis of a nonionic surfactant, 10% by weight of a chelant on a dry fibrous element basis and/or dry particle basis and/or dry fibrous structure basis, and 5% by weight of a perfume a dry fibrous element basis and/or dry particle basis and/or dry fibrous structure basis so that the total level of active agents present in the fibrous element and/or particle and/or fibrous structure is greater than 50%; namely 55% by weight on a dry fibrous element basis and/or dry particle basis and/or dry fibrous structure basis.

"Fibrous structure product" as used herein means a solid form, for example a rectangular solid, sometimes referred to as a sheet, that comprises one or more active agents, for example a fabric care active agent, a dishwashing active agent, a hard surface active agent, and mixtures thereof. In one example, a fibrous structure product of the present disclosure comprises one or more surfactants, one or more enzymes (such as in the form of an enzyme prill), one or more perfumes and/or one or more suds suppressors. In another example, a fibrous structure product of the present disclosure comprises a builder and/or a chelating agent. In another example, a fibrous structure product of the present disclosure comprises a bleaching agent (such as an encapsulated bleaching agent).

"Different from" or "different" as used herein means, with respect to a material, such as a fibrous element as a whole and/or a filament-forming material within a fibrous element and/or an active agent within a fibrous element, that one material, such as a fibrous element and/or a filament-forming material and/or an active agent, is chemically, physically and/or structurally different from another material, such as a fibrous element and/or a filament-forming material and/or an active agent. For example, a filament-forming material in the form of a filament is different from the same filament-forming material in the form of a fiber. Likewise, a starch polymer is different from a cellulose polymer. However, different molecular weights of the same material, such as different molecular weights of a starch, are not different materials from one another for purposes of the present disclosure.

"Random mixture of polymers" as used herein means that two or more different filament-forming materials are randomly combined to form a fibrous element. Accordingly, two or more different filament-forming materials that are orderly combined to form a fibrous element, such as a core and sheath bicomponent fibrous element, is not a random mixture of different filament-forming materials for purposes of the present disclosure.

"Associate," "Associated," "Association," and/or "Associating" as used herein with respect to fibrous elements and/or particle means combining, either in direct contact or in indirect contact, fibrous elements and/or particles such that a fibrous structure is formed. In one example, the associated fibrous elements and/or particles may be bonded together for example by adhesives and/or thermal bonds. In another example, the fibrous elements and/or particles may be associated with one another by being deposited onto the same fibrous structure making belt and/or patterned belt.

In one example, two or more fibrous structure plies may be bonded together by a chemical bonding agent, for example an adhesive, such as a water-containing adhesive. In another example, two or more fibrous structure plies may be bonded together by mechanical entanglement of fibrous elements, for example filaments, from one fibrous structure ply into an adjacent fibrous structure ply of a multi-ply fibrous structure, for example a multi-ply article. In another example, two or more fibrous structure plies may be bonded together by pressure bonds formed between two adjacent fibrous structure plies of a multi-ply fibrous structure, for example multi-ply article.

"Machine Direction" or "MD" as used herein means the direction parallel to the flow of the fibrous structure through the fibrous structure making machine and/or fibrous structure product manufacturing equipment.

"Cross Machine Direction" or "CD" as used herein means the direction perpendicular to the machine direction in the same plane of the fibrous structure and/or fibrous structure product comprising the fibrous structure.

"Ply" or "Plies" as used herein means an individual fibrous structure optionally to be disposed in a substantially contiguous, face-to-face relationship with other plies, forming a multiple ply fibrous structure. It is also contemplated that a single fibrous structure can effectively form two "plies" or multiple "plies", for example, by being folded on itself. A ply may comprise layers of filaments, filament/particle blends, and/or particles. In another example, there may be a layer of filaments or particles between plies.

As used herein, the articles "a" and "an" when used herein, for example, "an anionic surfactant" or "a fiber" is understood to mean one or more of the material that is claimed or described.

All percentages and ratios are calculated by weight unless otherwise indicated. All percentages and ratios are calculated based on the total composition unless otherwise indicated.

Unless otherwise noted, all component or composition levels are in reference to the active level of that component or composition, and are exclusive of impurities, for example, residual solvents or by-products, which may be present in commercially available sources.

Article Comprising a Fibrous Structure

The fibrous structures of the present disclosure comprise a plurality of fibrous elements, for example a plurality of filaments, such as a plurality of active agent-containing filaments, and optionally, one or more particles, for example one or more active agent-containing particles, such as water-soluble, active agent-containing particles and/or water-insoluble particles, such as zeolites, porous zeolites, perfume-loaded zeolites, active-loaded zeolites, silicas, perfume-loaded silicas, active-loaded zeolites, perfume microcapsules, clays, and mixtures thereof.

Without wishing to be bound by theory, it is believed that article dimensions can contribute to achieving the most consumer-preferred combination of performance factors of the article, prior to dissolution in a consumer's hands, with such factors including consumer-preferred article flexibility, ply bond strength, and containment or positioning in the palm of the consumer's hand just prior to and during initial dissolution. Furthermore, it is believed that article dimensions can contribute to achieving the most consumer-preferred performance, such as the creation of a smooth, silky, and lathery solution fitting in the palm of a consumer's hand before application to a surface to be treated. It is further believed that a superior combination of article performance in the dry state, as measured by flexibility, ply bond strength, and dispensing, during initial dissolving, as measured by Hand Dissolution Test Method, ability to fit within the palm of a consumer's hand just prior to and during initial dissolution, and performance upon application to the surface to be treated can be provided.

In certain examples, the article can have a length of from about 1 cm to about 20 cm; from about 2 cm to about 20 cm; from about 2 cm to about 18 cm; from about 3 cm to about 15 cm; from about 3 cm to about 12 cm; from about 4 cm to about 8 cm; from about 4 cm to about 6 cm; or from about 5 cm to about 6 cm. In certain examples, the article can have a length of from about 1 cm to about 10 cm; from about 2 cm to about 10 cm; or from about 7 cm to about 9 cm.

In certain examples, the article can have a width of from about 1 cm to about 11 cm; from about 2 cm to about 11 cm; from about 2 cm to about 10 cm; from about 3 cm to about 9 cm; from about 4 cm to about 8 cm; or from about 4 cm to about 6 cm. In certain examples, the article can have a width of from about 1 cm to about 6 cm; from about 2 cm to about 6 cm; from about 3 cm to about 5 cm; or from about 3.5 cm to about 4.5 cm. In other examples, the article can have a width of from about 6 cm to about 8 cm.

In certain examples, a ratio of a length of an article to its width can be from about 3:1 to about 0.5:1; from about 5:2 to about 0.5:1; or from about 2:1 to about 1:1.

The article can have a height, or thickness, of about 0.01 mm or greater; about 0.05 mm or greater; about 0.1 mm or greater; about 0.5 or greater; about 1 mm or greater; about 2 mm or greater; about 3 mm or greater; or about 4 mm or greater. In certain examples, the article can have a height, or thickness, of about 50 mm or less; about 20 mm or less; about 10 mm or less; about 8 mm or less; about 6 mm or less; about 5 mm or less; about 4 mm or less; about 3 mm or less; about 2 mm or less; about 1 mm or less; about 0.5 mm or less; or about 0.3 mm Thus, in certain examples, the article can have a height from about 0.01 mm to about 50 mm; from about 0.01 mm to about 44 mm; from about 0.1 mm to about 50 mm; from about 0.1 mm to about 44 mm; from about 1 mm to about 20 mm; or from about 1 mm to about 5 mm. In certain examples, the article can have a height, or thickness, of from about 3 mm to about 12 mm; or from about 4 mm to about 10 mm Height, or thickness, measurements are taken in accordance with the Thickness Test Method described herein.

The article can have a volume of from about 0.25 cubic centimeters (cc) to about 60 cc; from about 0.5 cc to about 60 cc; from about 0.5 cc to about 50 cc; from about 1 cc to about 40 cc; from about 1 cc to about 30 cc; from about 2 cc to about 20 cc; from about 3 cc to about 20 cc; from about 4 cc to about 15 cc; or from about 4 cc to about 10 cc. In certain examples, the article can have a volume of from about 3 cc to about 6 cc. In other examples, the article can have a volume of from about 20 cc to about 35 cc; or from about 24 cc to about 30 cc.

The article can have a mass of about 50 g or less; about 40 g or less; about 30 g or less; about 25 g or less; about 20 g or less; about 15 g or less; about 10 g or less; about 7.5 g or less; about 5 g or less; about 4 g or less; about 3 g or less; about 2 g or less; about 1.5 g or less; about 1.25 g or less; about 1 g or less; about 0.75 g or less; or about 0.5 g or less. In certain examples, the article can have a mass of from about 0.25 g to about 50 g; from about 0.25 g to about 40 g; from about 0.25 g to about 30 g; from about 0.25 g to about 25 g; from about 0.25 g to about 20 g; from about 0.5 g to about 15 g; from about 0.5 g to about 10 g; from about 0.5 to about 5 g; from about 0.5 g to about 4 g; from about 0.5 g to about 3 g; from about 0.5 g to about 2.5 g; or from about 1 g to about 2 g. In certain examples, the article can have a mass of from about 5 g to about 15 g; or from about 8 g to about 12 g.

The article can have a density of about 0.05 g/cc or greater; about 0.08 g/cc or greater; about 0.1 g/cc or greater; about 0.15 g/cc or greater; about 0.2 g/cc or greater; about 0.25 g/cc or greater; about 0.3 g/cc or greater; about 0.35 g/cc or greater; or about 0.4 g/cc or greater. In certain examples, the article can have a density of about 0.8 g/cc or less; about 0.6 g/cc or less; about 0.5 g/cc or less; about 0.4 g/cc or less; about 0.35 g/cc or less; about 0.3 g/cc or less; about 0.25 g/cc or less; about 0.2 g/cc or less; about 0.15 g/cc or less; about 0.12 g/cc or less; about 0.1 g/cc or less; about 0.08 g/cc or less; or about 0.05 g/cc or less. Thus, in certain examples, the article can have a density of from about 0.05 g/cc to about 0.8 g/cc; from about 0.08 g/cc to about 0.8 g/cc; from about 0.1 g/cc to about 0.8 g/cc; from about 0.2 g/cc to about 0.6 g/cc; or from about 0.2 g/cc to about 0.4 g/cc. In certain examples, the article can have a density of from about 0.3 g/cc to about 0.5 g/cc.

In certain examples, the article has one or more of the following dimensions: a width from about 1 cm to about 11 cm; a length from about 1 cm to about 20 cm; a height from about 0.01 mm to about 50 mm; a mass from about 0.25 g to about 40 g; a volume from about 0.25 cc to about 60 cc; and a density from about 0.05 g/cc to about 0.8 g/cc. In certain examples, the article has one or more of a width from about 1 cm to about 11 cm; a length from about 1 cm to about 20 cm; and a height from about 0.01 mm to about 50 mm. In certain examples, the article has one or more of a mass from about 0.25 g to about 40 g; a volume from about 0.25 cc to about 60 cc; and a density from about 0.05 g/cc to about 0.8 g/cc. In certain examples, the article has one or more of a width from about 1 cm to about 11 cm; a length from about 1 cm to about 20 cm; and a height from about 0.01 mm to about 50 mm; and one or more of a mass from about 0.25 g to about 40 g; a volume from about 0.25 cc to about 60 cc; and a density from about 0.05 g/cc to about 0.8 g/cc.

Additional ranges for the dimensions and properties of the article are described below in Table 3.

In addition to the article dimensions listed above, the articles, for examples dissolvable articles, such as polar solvent-soluble, for example water-soluble articles, for example fibrous structures of the present disclosure, may exhibit one or more of the following peel properties:
  a. an Average Inter-Ply Peak Peel Force of greater than 0.03 N and/or greater than 0.04 N and/or greater than 0.10 N and/or greater than 0.20 N and/or greater than 0.30 N and/or greater than 0.35 N and/or greater than 0.03 N to about 5.00 N and/or greater than 0.04 N to about 5.00 N and/or greater than 0.10 N to about 5.00 N and/or greater than 0.10 N to about 4.00 N and/or greater than 0.20 N to about 4.00 N and/or greater than 0.30 N to about 3.00 N as measured according to the Inter-Ply, Intra-Ply, and Whole 180° Peel Test Method described herein;

b. an Average Inter-ply Average Peel Force of greater than 0.02 N and/or greater than 0.04 N and/or greater than 0.05 N and/or greater than 0.10 N and/or greater than 0.15 N and/or greater than 0.20 N and/or greater than 0.25 N and/or greater than 0.02 N to about 5.00 N and/or greater than 0.04 N to about 5.00 N and/or greater than 0.05 N to about 5.00 N and/or greater than 0.10 N to about 4.00 N and/or greater than 0.15 N to about 4.00 N and/or greater than 0.20 N to about 3.00 N as measured according to the Inter-Ply, Intra-Ply, and Whole 180° Peel Test Method described herein;

c. an Average Intra-Ply Peak Peel Force of greater than 0.10 N and/or greater than 0.20 N and/or greater than 0.30 N and/or greater than 0.40 N and/or greater than 0.50 N and/or greater than 0.60 N and/or greater than 0.70 N and/or greater than 0.10 N to about 5.00 N and/or greater than 0.20 N to about 5.00 N and/or greater than 0.30 N to about 5.00 N and/or greater than 0.40 N to about 4.00 N and/or greater than 0.50 N to about 4.00 N and/or greater than 0.60 N to about 3.00 N as measured according to the Inter-Ply, Intra-Ply, and Whole 180° Peel Test Method described herein;

d. an Average Intra-Ply Average Peel Force of greater than 0.10 N and/or greater than 0.15 N and/or greater than 0.20 N and/or greater than 0.25 N and/or greater than 0.30 N and/or greater than 0.35 N and/or greater than 0.40 N and/or greater than 0.10 N to about 5.00 N and/or greater than 0.20 N to about 5.00 N and/or greater than 0.25 N to about 5.00 N and/or greater than 0.30 N to about 4.00 N and/or greater than 0.35 N to about 4.00 N and/or greater than 0.40 N to about 3.00 N as measured according to the Inter-Ply, Intra-Ply, and Whole 180° Peel Test Method described herein;

e. an Average Whole 180° Peak Peel Force of greater than 0.03 N and/or greater than 0.04 N and/or greater than 0.05 N and/or greater than 0.10 N and/or greater than 0.20 N and/or greater than 0.30 N and/or greater than 0.03 N to about 5.00 N and/or greater than 0.04 N to about 5.00 N and/or greater than 0.10 N to about 5.00 N and/or greater than 0.10 N to about 4.00 N and/or greater than 0.20 N to about 4.00 N and/or greater than 0.30 N to about 3.00 N as measured according to the Inter-Ply, Intra-Ply, and Whole 180° Peel Test Method described herein; and f. an Average Whole 180° Average Peel Force of greater than 0.02 N and/or greater than 0.04 N and/or greater than 0.05 N and/or greater than 0.10 N and/or greater than 0.15 N and/or greater than 0.20 N and/or greater than 0.02 N to about 5.00 N and/or greater than 0.04 N to about 5.00 N and/or greater than 0.05 N to about 5.00 N and/or greater than 0.10 N to about 4.00 N and/or greater than 0.15 N to about 4.00 N and/or greater than 0.20 N to about 3.00 N as measured according to the Inter-Ply, Intra-Ply, Whole 180° Peel Test Method described herein.

In addition to the article dimensions listed above, and optionally one or more of the peel properties described above, the articles, for example fibrous structures of the present disclosure, may exhibit one or more of the following properties:

a. an Average Maximum Peak Force of less than 20.00 N and/or less than 15.00 N and/or less than 10.00 N and/or less than 8.50 N and/or less than 7.50 N and/or less than 5.00 N and/or greater than 0 N and/or greater than 0 to less than 20.00 N as measured according to the Modified Circular Bend Test Method described herein;

b. an Average Bending Stiffness of less than 3000.0 N/m and/or less than 2500.0 N/m and/or less than 2200.0 N/m and/or less than 1900.0 N/m and/or less than 1600.0 N/m and/or less than 1200.0 N/m and/or less than 1000.0 N/m and/or less than 800.0 N/m and/or less than 500.0 N/m and/or greater than 100.0 N/m and/or less than 3000.0 N/m to greater than 100.0 N/m as measured according to the Modified Circular Bend Test Method described herein; and c. an Average Hand Dissolution of less than 30 Dissolution Strokes and/or less than 29 Dissolution Strokes and/or less than 25 Dissolution Strokes and/or less than 20 Dissolution Strokes and/or less than 15 Dissolution Strokes and/or less than 10 Dissolution Strokes and/or less than 5 Dissolution Strokes and/or less than 30 Dissolution Strokes to greater than 0 Dissolution Strokes and/or less than 25 Dissolution Strokes to at least 1 Dissolution Stroke as measured according to the Hand Dissolution Test Method described herein.

In addition to the article dimensions listed above, and optionally one or more of the peel properties, when the article comprises a multi-ply fibrous structure according to the present disclosure, the multi-ply fibrous structure may also exhibit one or more of the following Lap Shear properties:

a. an Average Lap Shear Peak Force of greater than 0.05 N and/or greater than 0.10 N and/or greater than 0.20 N and/or greater than 0.50 N and/or greater than 1.00 N and/or greater than 2.00 N and/or greater than 5.00 N and/or greater than 7.00 N and/or greater than 10.00 N and/or greater than 12.00 N and/or greater than 0.05 N to about 20.00 N and/or greater than 0.10 N to about 15.00 N and/or greater than 0.20 N to about 15.00 N and/or greater than 0.50 N to about 10.00 N and/or greater than 1.00 N to about 10.00 N as measured according to the Lap Shear Test Method described herein; and b. an Average Lap Shear Average Energy of greater than 0.10 N*mm and/or greater than 0.30 N*mm and/or greater than 0.50 N*mm and/or greater than 1.00 N*mm and/or greater than 5.00 N*mm and/or greater than 10.00 N*mm and/or greater than 15.00 N*mm and/or greater than 20.00 N*mm and/or greater than 25.00 N*mm and/or greater than 30.00 N*mm and/or greater than 35.00 N*mm and/or greater than 0.10 N*mm to about 100.00 N*mm and/or greater than 0.30 N*mm to about 75.00 N*mm and/or greater than 1.00 N*mm to about 75.00 N*mm and/or greater than 5.00 N*mm to about 50.00 N*mm and/or greater than 10.00 N*mm to about 50.00 N*mm as measured according to the Lap Shear Test Method described herein.

In one example, one more plies of a fibrous structure according to the present disclosure may be associated with one or more other plies of fibrous structure, for example another fibrous structure ply according to the present disclosure, by bonding the plies together, such as by glue, adhesive, water, thermal bonding, pressure bonding, entanglement of fibers from one ply into another ply, needle punching of fibers from one ply into another ply, temporary bonding of plies, ply bonding of only discontinuous or discrete zones/areas between plies, combinations of ply bonding approaches mentioned herein, or other suitable means of bonding the plies together such that the multi-ply fibrous structure exhibits peel properties as described herein. In another example, the two or more of the fibrous structure plies may be bonded together by mechanical entanglement of filaments from one fibrous structure ply into an adjacent fibrous structure ply such that the multi-ply fibrous structure exhibits peel properties as described herein.

The articles, for example fibrous structures according to the present disclosure may exhibit an Average Hand Dissolution Value of less than 30 Dissolution Strokes and/or less than 29 Dissolution Strokes and/or less than 25 Dissolution Strokes and/or less than 20 Dissolution Strokes and/or less than 15 Dissolution Strokes and/or less than 10 Dissolution Strokes and/or less than 5 Dissolution Strokes as measured according to the Hand Dissolution Test Method described herein.

In one example, the article, for example fibrous structure of the present disclosure may exhibit an average disintegration time of less than 360 seconds (s) and/or less than 200 s and/or less than 100 s and/or less than 60 s and/or less than 30 s, and/or less than 10 s and/or less than 5 s and/or less than 2.0 s and/or less than 1.5 s and/or about 0 s and/or greater than 0 s as measured according to the Dissolution Test Method described herein.

In one example, the article, for example fibrous structure of the present disclosure may exhibit an average dissolution time of less than 3600 seconds (s) and/or less than 3000 s and/or less than 2400 s and/or less than 1800 s and/or less than 1200 s and/or less than 600 s and/or less than 400 s and/or less than 300 s and/or less than 200 s and/or less than 175 s and/or less than 100 s and/or less than 50 s and/or greater than 1 s as measured according to the Dissolution Test Method described herein.

In another example, the article, for example fibrous structure of the present disclosure exhibits an average dissolution time of less than 24 hours and/or less than 12 hours and/or less than 6 hours and/or less than 1 hour (3600 seconds) and/or less than 30 minutes and/or less than 25 minutes and/or less than 20 minutes and/or less than 15 minutes and/or less than 10 minutes and/or less than 5 minutes and/or greater than 1 second and/or greater than 5 seconds and/or greater than seconds and/or greater than 30 seconds and/or greater than 1 minute as measured according to the Dissolution Test Method described herein.

In one example, the article, for example fibrous structure of the present disclosure may exhibit an average disintegration time per gsm of sample of about 1.0 second/gsm (s/gsm) or less, and/or about 0.5 s/gsm or less, and/or about 0.2 s/gsm or less, and/or about 0.1 s/gsm or less, and/or about 0.05 s/gsm or less, and/or about 0.03 s/gsm or less as measured according to the Dissolution Test Method described herein.

In one example, the article, for example fibrous structure of the present disclosure may exhibit an average dissolution time per gsm of sample of about 10 seconds/gsm (s/gsm) or less, and/or about 5.0 s/gsm or less, and/or about 3.0 s/gsm or less, and/or about 2.0 s/gsm or less, and/or about 1.8 s/gsm or less, and/or about 1.5 s/gsm or less as measured according to the Dissolution Test Method described herein.

In one example, the fibrous elements and/or particles may be arranged within the fibrous structure to provide the fibrous structure with two or more regions or layers that comprise different active agents. For example, one region of the fibrous structure may comprise bleaching agents and/or surfactants and another region of the fibrous structure may comprise softening agents.

Figure 2:
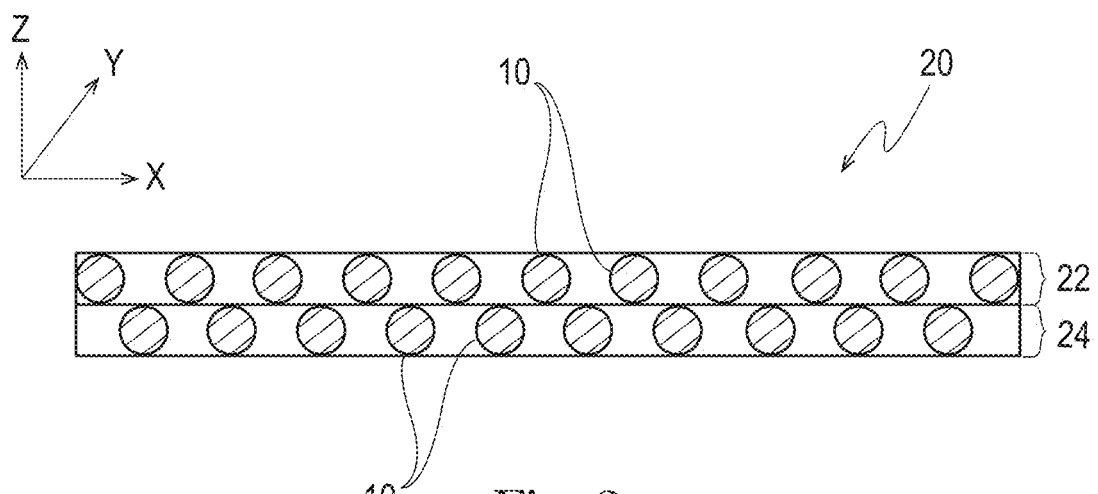
FIG. 2 is a schematic representation of an example of a fibrous structure comprising a plurality of filaments according to the present disclosure.
Figure 3:
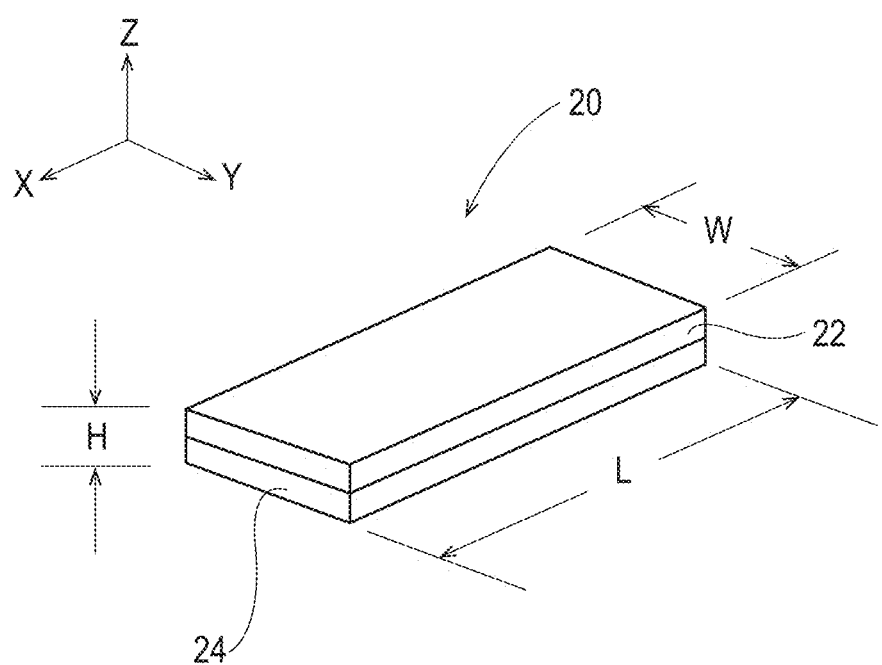
FIG. 3 is another schematic representation of the article of FIG. 2, depicting article dimensions.

As shown in FIG. 2, an example of an article 20 of the present disclosure, for example a multi-ply fibrous structure according to the present disclosure may comprise two or more different fibrous structure layers or plies 22, 24 (in the z-direction of the article 20 of filaments 10 of the present disclosure that form the fibrous structures of the article 20. The filaments 10 in layer 22 may be the same as or different from the filaments 10 in layer 24. Each layer or ply 22, 24 may comprise a plurality of identical or substantially identical or different filaments. For example, filaments that may release their active agents at a faster rate than others within the article 20 and/or one or more fibrous structure layers or plies 22, 24 of the article 20 may be positioned as an external surface of the article 20. The layers or plies 22 and 24 may be associated with each other by mechanical entanglement at their interface between the two layers or plies and/or by thermal or adhesive bonding and/or by depositing one of the layers or plies onto the other existing layer or ply, for example spinning the fibrous elements of layer or ply 22 onto the surface of the layer or ply 24. FIG. 3 shows another view of the article 20, with plies 22 and 24. With respect to the article dimensions described above, the length (L), width (W), and height (H) of the article are shown in FIG. 3 to correspond to measurements in the x-, y-, and z-directions, respectively.

Figure 4:
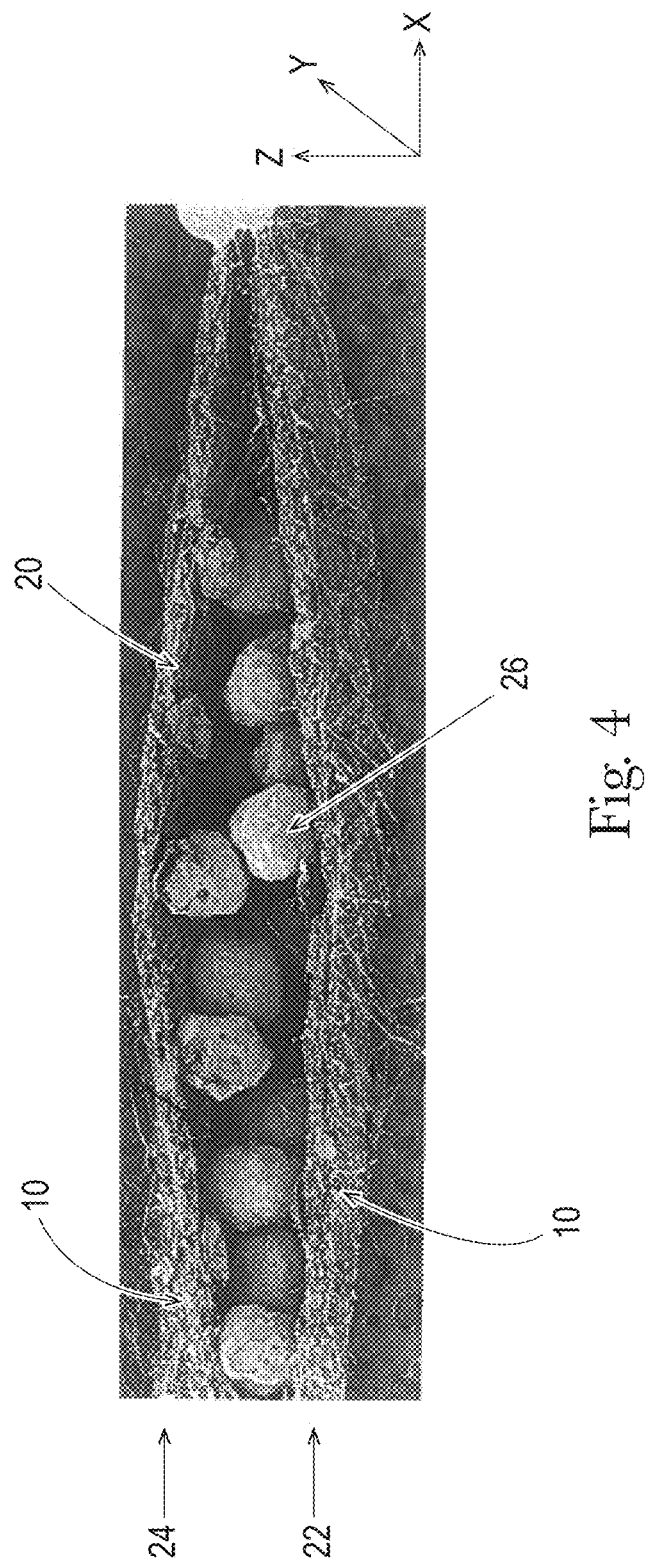
FIG. 4 is a scanning electron microscope photograph of a cross-sectional view of an example of a fibrous structure according to the present disclosure.

As shown in FIG. 4, another example of an article 20, for example a fibrous structure according to the present disclosure comprises a first fibrous structure layer or ply 22 comprising a plurality of fibrous elements, for example filaments 10, a second fibrous structure layer 24 comprising a plurality of fibrous elements, for example filaments 10, and a plurality of particles or a particle layer 26 positioned between the first and second fibrous structure layers 22 and 24. A similar fibrous structure can be formed by depositing a plurality of particles on a surface of a first ply of fibrous structure comprising a plurality of fibrous elements and then associating a second ply of fibrous structure comprising a plurality of fibrous elements such that the particles or a particle layer are positioned between the first and second fibrous structure plies.

Figure 5:
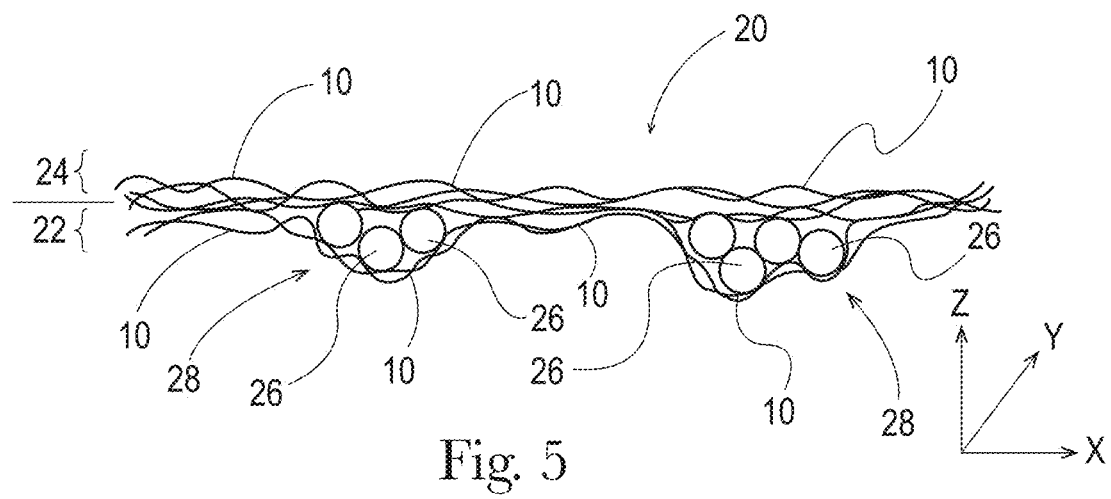
FIG. 5 is a schematic representation of a cross-sectional view of another example of a fibrous structure according to the present disclosure.

As shown in FIG. 5, another example of an article 20, for example a fibrous structure of the present disclosure comprises a first fibrous structure layer 22 comprising a plurality of fibrous elements, for example filaments 10, wherein the first fibrous structure layer 22 comprises one or more pockets 28 (also referred to as recesses, unfilled domes, or deflected zones), which may be in an irregular pattern or a non-random, repeating pattern. One or more of the pockets 28 may contain one or more particles 26. The article 20 in this example further comprises a second fibrous structure layer 24 that is associated with the first fibrous structure layer 22 such that the particles 26 are entrapped in the pockets 28. Like above, a similar article can be formed by depositing a plurality of particles in pockets of a first ply of fibrous structure comprising a plurality of fibrous elements and then associating a second ply of fibrous structure comprising a plurality of fibrous elements such that the particles are entrapped within the pockets of the first ply. In one example, the pockets may be separated from the fibrous structure to produce discrete pockets.

Figure 6:
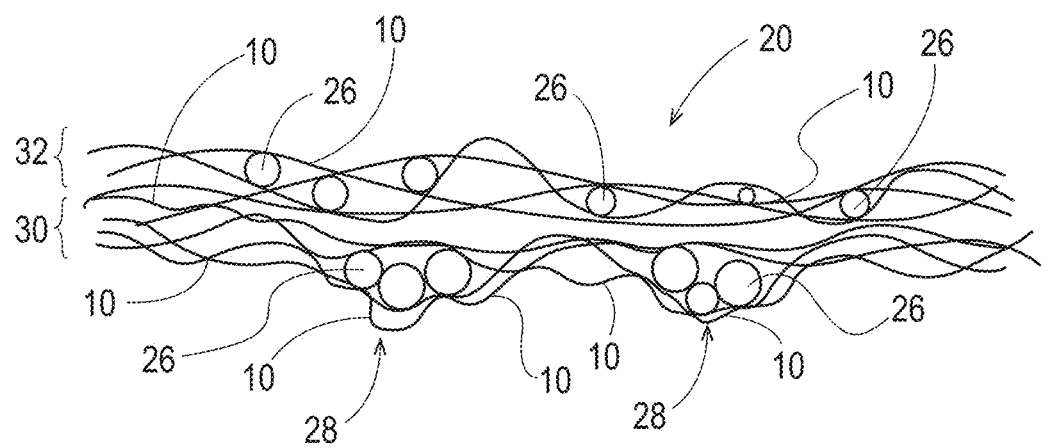
FIG. 6 is a schematic representation of a cross-sectional view of another example of a fibrous structure according to the present disclosure.

As shown in FIG. 6, another example of an article 20, for example a multi-ply fibrous structure of the present disclosure comprises a first ply 30 of a fibrous structure according to FIG. above and a second ply 32 of fibrous structure associated with the first ply 30, wherein the second ply 32 comprises a plurality of fibrous elements, for example filaments 10, and a plurality of particles 26 dispersed, in this case randomly, in the x, y, and z axes, throughout the article 20.

Figure 7:
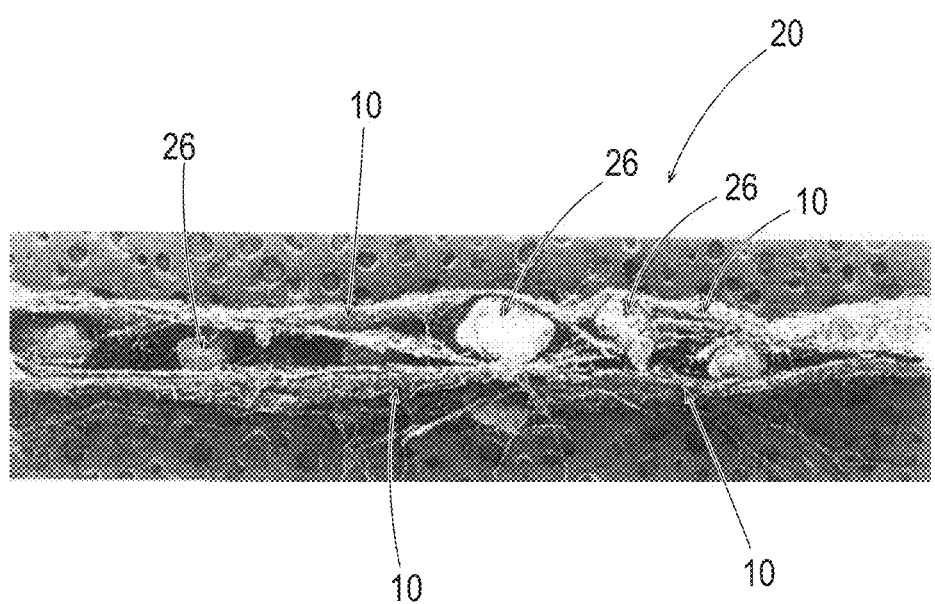
FIG. 7 is a scanning electron microscope photograph of a cross-sectional view of another example of a fibrous structure according to the present disclosure.

As shown in FIG. 7, another example of an article 20, for example a fibrous structure of the present disclosure comprises a plurality of fibrous elements, for example filaments 10, such as active agent-containing filaments, and a plurality of particles 26, for example active agent-containing particles, dispersed, in this case randomly, in the x, y, and z axes, throughout the fibrous structure of the article 20.

Figure 8:
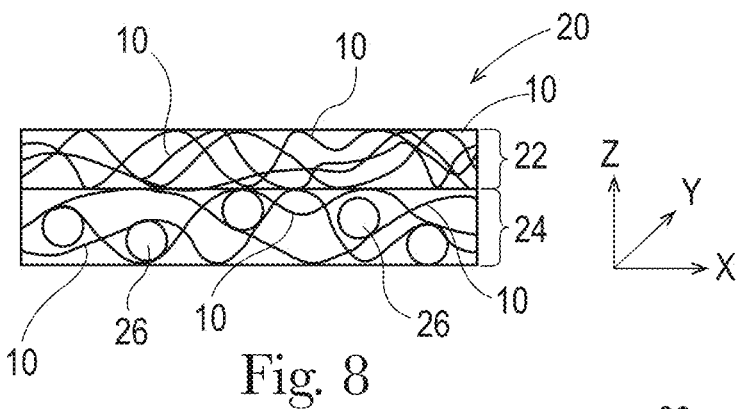
FIG. 8 is a schematic representation of a cross-sectional view of another example of a fibrous structure according to the present disclosure.

As shown in FIG. 8, another example of an article 20, for example a fibrous structure of the present disclosure comprises a first fibrous structure layer 22 comprising a plurality of fibrous elements, for example filaments 10, and a second fibrous structure layer 24 comprising a plurality of fibrous elements, for example filaments 10, for example active agent-containing filaments, and a plurality of particles 26, for example active agent-containing particles, dispersed, in this case randomly, in the x, y, and z axes, throughout the second fibrous structure layer 24. Alternatively, in another example, the plurality of particles 26, for example active agent-containing particles, may be dispersed in an irregular pattern or a non-random, repeating pattern within the second fibrous structure layer 24. Like above, a similar article comprising two plies of fibrous structure comprising a first fibrous structure ply 22 comprising a plurality of fibrous elements, for example filaments 10, and a second fibrous structure ply 24 comprising a plurality of fibrous elements, for example filaments 10, for example active agent-containing filaments, and a plurality of particles 26, for example active agent-containing particles, dispersed, in this case randomly, in the x, y, and z axes, throughout the second fibrous structure ply 24. Alternatively, in another example, the plurality of particles 26, for example active agent-containing particles, may be dispersed in an irregular pattern or a non-random, repeating pattern within the second fibrous structure ply 24.

Figure 9:
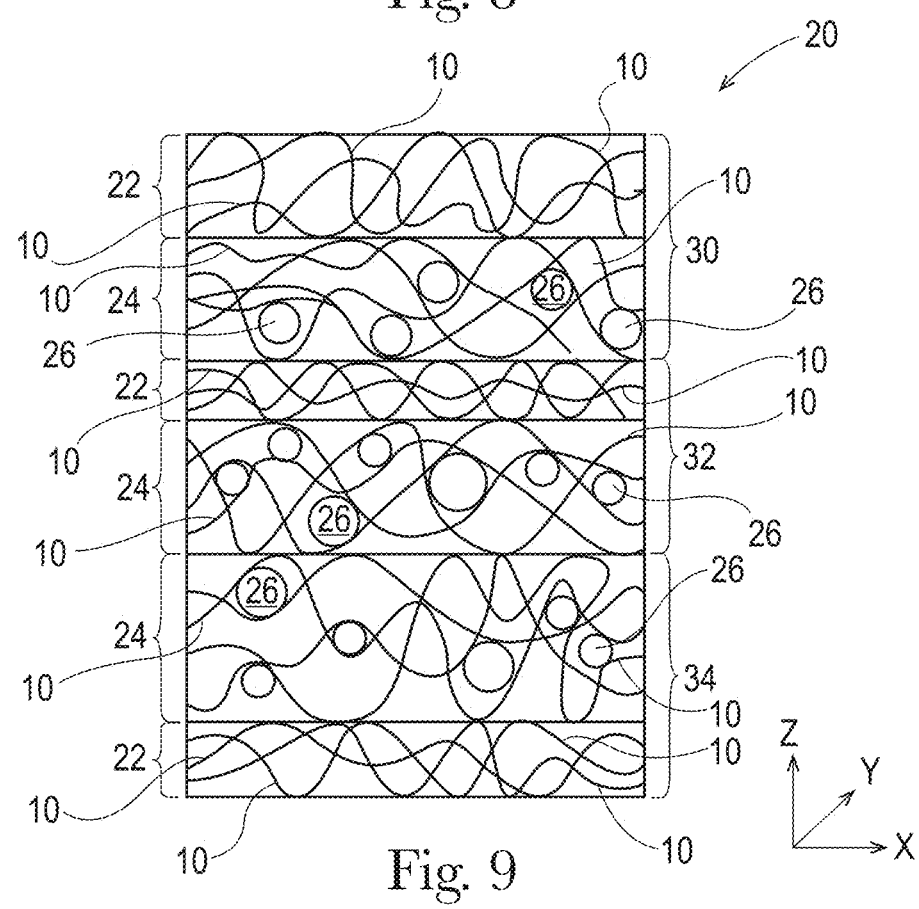
FIG. 9 is a schematic representation of a cross-sectional view of another example of a fibrous structure according to the present disclosure.

FIG. 9 shows another example of an article 20, for example a multi-ply fibrous structure of the present disclosure comprising a first ply 30 of a fibrous structure as shown in FIG. 8 comprising a first fibrous structure layer 22 comprising a plurality of fibrous elements, for example filaments 10, and a second fibrous structure layer 24 comprising a plurality of fibrous elements, for example filaments 10, for example active agent-containing filaments, and a plurality of particles 26, for example active agent-containing particles, dispersed, in this case randomly, in the x, y, and z axes, throughout the second fibrous structure layer 24, a second ply 32 of a fibrous structure associated with the first ply 30, wherein the second ply 32 comprises a first fibrous structure layer 22 comprising a plurality of fibrous elements, for example filaments 10, and a second layer 24 comprising a plurality of fibrous elements, for example filaments 10, for example active agent-containing filaments, and a plurality of particles 26, for example active agent-containing particles, dispersed, in this case randomly, in the x, y, and z axes, throughout the second fibrous structure layer 24, and a third ply 34 of a fibrous structure associated with the second ply 32, wherein the third ply 34 comprises a first fibrous structure layer 22 comprising a plurality of fibrous elements, for example filaments 10, and a second fibrous structure layer 24 comprising a plurality of fibrous elements, for example filaments 10, for example active agent-containing filaments, and a plurality of particles 26, for example active agent-containing particles, dispersed, in this case randomly, in the x, y, and z axes, throughout the second fibrous structure layer 24.

Figure 10:
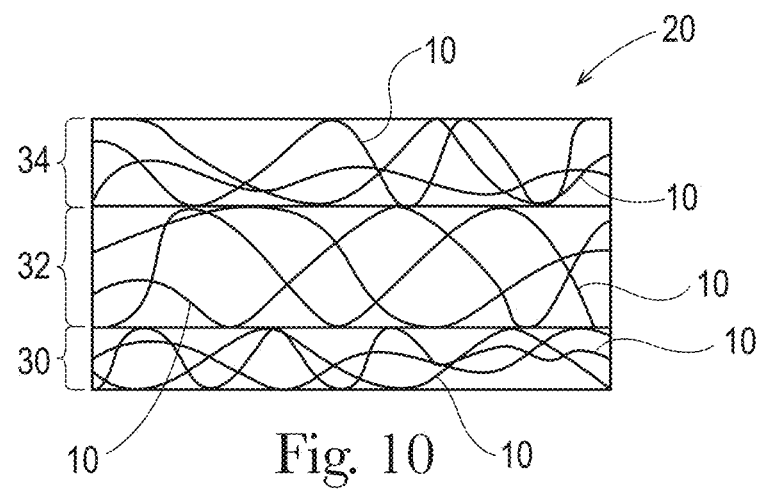
FIG. 10 is a schematic representation of a cross-sectional view of another example of a fibrous structure according to the present disclosure.

As shown in FIG. 10, another example of an article 20, for example a multi-ply fibrous structure of the present disclosure comprises a first ply 30 of a fibrous structure comprising a plurality of fibrous elements, for example filaments 10, a second ply 32 of a fibrous structure associated with the first ply 30, wherein the second ply 32 comprises a plurality of fibrous elements, for example filaments 10, and a third ply 34 of a fibrous structure associated with the second ply 32, wherein the third ply 34 comprises a plurality of fibrous elements, for example filaments 10. In one example of FIG. 10, each ply's filaments 10 may comprise active agent-containing filaments.

Figure 11:
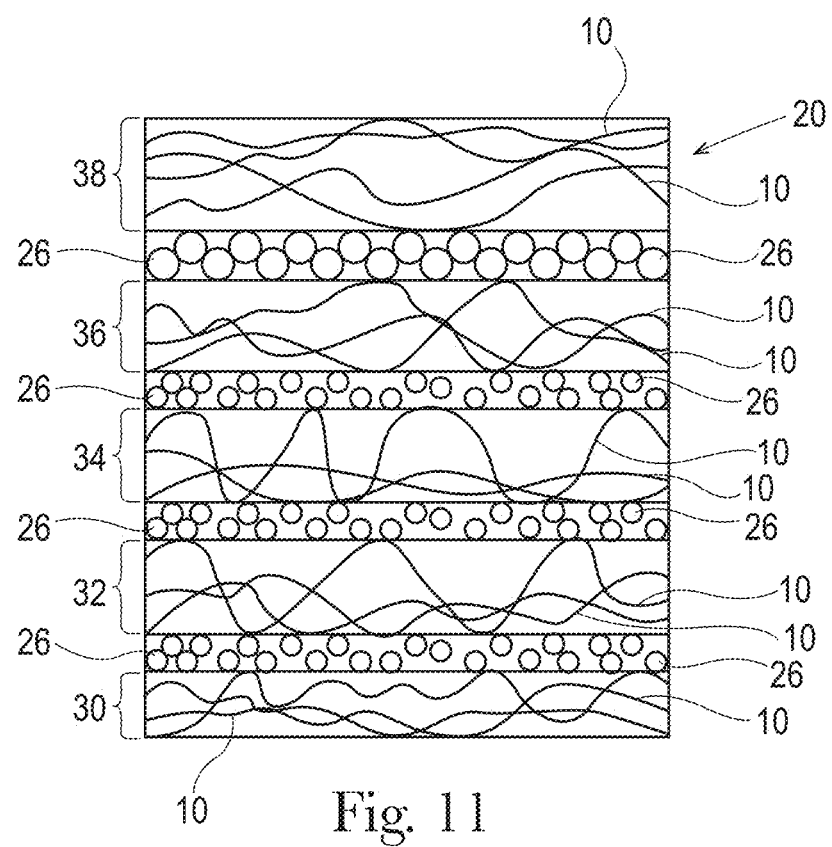
FIG. 11 is a schematic representation of a cross-sectional view of another example of a fibrous structure according to the present disclosure.

FIG. 11 shows another example of an article 20 multi-ply fibrous structure 20 of the present disclosure comprising a first ply 30 of a fibrous structure comprising a plurality of fibrous elements, for example filaments 10, a second ply 32 of fibrous structure comprising a plurality of fibrous elements, for example filaments 10, a third ply 34 of a fibrous structure comprising a plurality of fibrous elements, for example filaments 10, a fourth ply 36 of fibrous structure comprising a plurality of fibrous elements, for example filaments 10, and a fifth ply 38 of a fibrous structure comprising a plurality of fibrous elements, for example filaments 10. In this example, the article further comprises one or more particles or particle layers 26 positioned between at least two adjacent fibrous structure plies, for example plies 30 and 32 or plies 32 and 34 or plies 34 and 36 or plies 36 and 38. The plies 30, 32, 34, 36, and 38 are associated with one or more other plies to form a unitary structure and to minimize particles 26, if any are present within the article 20, from becoming disassociated from the article 20. In another example, the one or more particles or particle layers 26 positioned between at least two adjacent fibrous structure plies are present in an irregular pattern, a non-random, repeating pattern, or only in select zones between the plies.

Even though the fibrous element and/or fibrous structure of the present disclosure are in solid form, the filament-forming composition used to make the fibrous elements of the present disclosure may be in the form of a liquid.

In one example, the fibrous structure comprises a plurality of identical or substantially identical from a compositional perspective of fibrous elements according to the present disclosure. In another example, the fibrous structure may comprise two or more different fibrous elements according to the present disclosure. Non-limiting examples of differences in the fibrous elements may be physical differences such as differences in diameter, length, texture, shape, rigidness, elasticity, and the like; chemical differences such as crosslinking level, solubility, melting point, Tg, active agent, filament-forming material, color, level of active agent, basis weight, level of filament-forming material, presence of any coating on fibrous element, biodegradable or not, hydrophobic or not, contact angle, and the like; differences in whether the fibrous element loses its physical structure when the fibrous element is exposed to conditions of intended use; differences in whether the fibrous element's morphology changes when the fibrous element is exposed to conditions of intended use; and differences in rate at which the fibrous element releases one or more of its active agents when the fibrous element is exposed to conditions of intended use. In one example, two or more fibrous elements and/or particles within the fibrous structure may comprise different active agents. This may be the case where the different active agents may be incompatible with one another, for example an anionic surfactant (such as a shampoo active agent) and a cationic surfactant (such as a hair conditioner active agent).

In one example, at least one of the one or more active agents present within the fibrous element comprises a first surfactant and the active agent-containing particle comprises a second surfactant, for example wherein the first surfactant is different from the second surfactant.

In another example, the fibrous structure may exhibit different regions, such as different regions of basis weight, density and/or caliper. In yet another example, the fibrous structure may comprise texture on one or more of its surfaces. A surface of the fibrous structure may comprise a pattern, such as a non-random, repeating pattern. The fibrous structure may be embossed with an emboss pattern. In another example, the fibrous structure may comprise apertures. The apertures may be arranged in a non-random, repeating pattern.

In one example, the fibrous structure may comprise discrete regions of fibrous elements that differ from other parts of the fibrous structure.

Non-limiting examples of use of the fibrous structure of the present disclosure include, but are not limited to a laundry dryer substrate, washing machine substrate, washcloth, hard surface cleaning and/or polishing substrate, floor cleaning and/or polishing substrate, as a component in a battery, baby wipe, adult wipe, feminine hygiene wipe, bath tissue wipe, window cleaning substrate, oil containment and/or scavenging substrate, insect repellant substrate, swimming pool chemical substrate, food, breath freshener, deodorant, waste disposal bag, packaging film and/or wrap, wound dressing, medicine delivery, building insulation, crops and/or plant cover and/or bedding, glue substrate, skin care substrate, hair care substrate, air care substrate, water treatment substrate and/or filter, toilet bowl cleaning substrate, candy substrate, pet food, livestock bedding, teeth whitening substrates, carpet cleaning substrates, and other suitable uses of the active agents of the present disclosure.

The fibrous structure of the present disclosure may be used as is or may be coated with one or more active agents.

In one example, a fibrous structure can exhibit a thickness of greater than 0.01 mm and/or greater than 0.05 mm and/or greater than 0.1 mm and/or to about 50 mm and/or to about 20 mm and/or to about 10 mm and/or to about 5 mm and/or to about 2 mm and/or to about 0.5 mm and/or to about 0.3 mm as measured by the Thickness Test Method described herein.

Non-limiting examples of other fibrous structures suitable for the present disclosure are disclosed in U.S. Published Patent Application No. 2013/0171421 A1 and U.S. Pat. No. 9,139,802 are hereby incorporated by reference herein.
Particles The particles may be water-soluble or water-insoluble. In one example, one group of particles may be water-soluble and a different group of particles may be water-insoluble. The particles, water-soluble or water-insoluble, may themselves deliver a benefit to the consumer. In another example, the particles, water-soluble or water-insoluble, may comprise one or more active agents (in other words, the particles may comprises active agent-containing particles). In still another example, the particles may consist essentially of and/or consist of one or more active agents (in other words, the particles, water-soluble and/or water-insoluble, may comprise 100% or greater than about 100% by weight on a dry particle basis of one or more active agents). In still another example, the particles may comprise water-soluble particles. In yet another example, the particles may comprise water-soluble, active agent-containing particles. In one other example, the water-insoluble particles comprise zeolites, porous zeolites, perfume-loaded zeolites, active loaded zeolites, silicas, perfume-loaded silicas, active loaded silicas, perfume microcapsules, clays, and mixtures thereof.

In one example, the particle comprises a water-soluble particle, for example a water-soluble, active agent-containing particle comprising an active agent selected from the group consisting of: bleaching agents, builders, enzymes, antimicrobials, antibacterials, antifungals, perfume delivery systems, dye transfer inhibiting agents, brighteners, hueing dyes and mixtures thereof. In one example, the water-soluble, active agent-containing particle comprises an enzyme prill. In another example, the water-soluble, active agent-containing particles comprises an encapsulated bleaching agent. In another example, the water-soluble, active agent-containing particles comprises a perfume microcapsule.

In one example, at least one of the particles comprises a water-insoluble particle, for example a water-insoluble, active agent-containing particle.

In one example, one or more particles are present as discrete particles within the article.
Fibrous Elements The fibrous elements may be water-soluble or water-insoluble. In one example, the fibrous elements comprise one or more filament-forming materials. In another example, the fibrous elements comprise one or more active agents. In still another example, the fibrous elements comprise one or more filament-forming materials and one or more active agents. In another example, the fibrous elements may comprise water-soluble fibrous elements.

The fibrous element, such as a filament and/or fiber, of the present disclosure comprises one or more filament-forming materials. In addition to the filament-forming materials, the fibrous element may further comprise one or more active agents that are releasable from the fibrous element, such as when the fibrous element and/or fibrous structure comprising the fibrous element is exposed to conditions of intended use. In one example, the total level of the one or more filament-forming materials present in the fibrous element is less than 80% by weight on a dry fibrous element basis and/or dry fibrous structure basis and the total level of the one or more active agents present in the fibrous element is greater than 20% by weight on a dry fibrous element basis and/or dry fibrous structure basis.

In one example, the fibrous element of the present disclosure comprises about 100% and/or greater than 95% and/or greater than 90% and/or greater than 85% and/or greater than 75% and/or greater than 50% by weight on a dry fibrous element basis and/or dry fibrous structure basis of one or more filament-forming materials. For example, the filament-forming material may comprise polyvinyl alcohol, starch, carboxymethylcellulose, and other suitable polymers, especially hydroxyl polymers.

In another example, the fibrous element of the present disclosure comprises one or more filament-forming materials and one or more active agents wherein the total level of filament-forming materials present in the fibrous element is from about 5% to less than 80% by weight on a dry fibrous element basis and/or dry fibrous structure basis and the total level of active agents present in the fibrous element is greater than 20% to about 95% by weight on a dry fibrous element basis and/or dry fibrous structure basis.

In one example, the fibrous element of the present disclosure comprises at least 10% and/or at least 15% and/or at least 20% and/or less than less than 80% and/or less than 75% and/or less than 65% and/or less than 60% and/or less than 55% and/or less than 50% and/or less than 45% and/or less than 40% by weight on a dry fibrous element basis and/or dry fibrous structure basis of the filament-forming materials and greater than about 20% and/or at least about 30% and/or at least about 35% and/or at least about 40% and/or at least about 45% and/or at least about 50% and/or at least about 60% and/or less than about 95% and/or less than about 90% and/or less than about 85% and/or less than about 80% and/or less than about 75% by weight on a dry fibrous element basis and/or dry fibrous structure basis of active agents.

In one example, the fibrous element of the present disclosure comprises at least 5% and/or at least 10% and/or at least 15% and/or at least 20% and/or less than 50% and/or less than 45% and/or less than 40% and/or less than 35% and/or less than 30% and/or less than 25% by weight on a dry fibrous element basis and/or dry fibrous structure basis of the filament-forming materials and greater than about 30% and/or at least about 50% and/or at least about 55% and/or at least about 60% and/or at least about 65% and/or at least about 70% and/or less than about 95% and/or less than about 90% and/or less than about 85% and/or less than about 80% and/or less than about 75% by weight on a dry fibrous element basis and/or dry fibrous structure basis of active agents. In one example, the fibrous element of the present disclosure comprises greater than 80% by weight on a dry fibrous element basis and/or dry fibrous structure basis of active agents.

In another example, the one or more filament-forming materials and active agents are present in the fibrous element at a weight ratio of total level of filament-forming materials to active agents of 4.0 or less and/or 3.5 or less and/or 3.0 or less and/or 2.5 or less and/or 2.0 or less and/or 1.85 or less and/or less than 1.7 and/or less than 1.6 and/or less than 1.5 and/or less than 1.3 and/or less than 1.2 and/or less than 1 and/or less than 0.7 and/or less than 0.5 and/or less than 0.4 and/or less than 0.3 and/or greater than 0.1 and/or greater than 0.15 and/or greater than 0.2.

In still another example, the fibrous element of the present disclosure comprises from about 10% and/or from about 15% to less than 80% by weight on a dry fibrous element basis and/or dry fibrous structure basis of a filament-forming material, such as polyvinyl alcohol polymer, starch polymer, and/or carboxymethylcellulose polymer, and greater than 20% to about 90% and/or to about 85% by weight on a dry fibrous element basis and/or dry fibrous structure basis of an active agent. The fibrous element may further comprise a plasticizer, such as glycerin and/or pH adjusting agents, such as citric acid.

In yet another example, the fibrous element of the present disclosure comprises from about 10% and/or from about 15% to less than 80% by weight on a dry fibrous element basis and/or dry fibrous structure basis of a filament-forming material, such as polyvinyl alcohol polymer, starch polymer, and/or carboxymethylcellulose polymer, and greater than 20% to about 90% and/or to about 85% by weight on a dry fibrous element basis and/or dry fibrous structure basis of an active agent, wherein the weight ratio of filament-forming material to active agent is 4.0 or less. The fibrous element may further comprise a plasticizer, such as glycerin and/or pH adjusting agents, such as citric acid.

In even another example of the present disclosure, a fibrous element comprises one or more filament-forming materials and one or more active agents selected from the group consisting of: enzymes, bleaching agents, builder, chelants, sensates, dispersants, and mixtures thereof that are releasable and/or released when the fibrous element and/or fibrous structure comprising the fibrous element is exposed to conditions of intended use. In one example, the fibrous element comprises a total level of filament-forming materials of less than 95% and/or less than 90% and/or less than 80% and/or less than 50% and/or less than 35% and/or to about 5% and/or to about 10% and/or to about 20% by weight on a dry fibrous element basis and/or dry fibrous structure basis and a total level of active agents selected from the group consisting of: enzymes, bleaching agents, builder, chelants, perfumes, antimicrobials, antibacterials, antifungals, and mixtures thereof of greater than 5% and/or greater than 10% and/or greater than 20% and/or greater than 35% and/or greater than 50% and/or greater than 65% and/or to about 95% and/or to about 90% and/or to about 80% by weight on a dry fibrous element basis and/or dry fibrous structure basis. In one example, the active agent comprises one or more enzymes. In another example, the active agent comprises one or more bleaching agents. In yet another example, the active agent comprises one or more builders. In still another example, the active agent comprises one or more chelants. In still another example, the active agent comprises one or more perfumes. In even still another example, the active agent comprise one or more antimicrobials, antibacterials, and/or antifungals.

In yet another example of the present disclosure, the fibrous elements of the present disclosure may comprise active agents that may create health and/or safety concerns if they become airborne. For example, the fibrous element may be used to inhibit enzymes within the fibrous element from becoming airborne.

In one example, the fibrous elements of the present disclosure may be meltblown fibrous elements. In another example, the fibrous elements of the present disclosure may be spunbond fibrous elements. In another example, the fibrous elements may be hollow fibrous elements prior to and/or after release of one or more of its active agents.

The fibrous elements of the present disclosure may be hydrophilic or hydrophobic. The fibrous elements may be surface treated and/or internally treated to change the inherent hydrophilic or hydrophobic properties of the fibrous element.

In one example, the fibrous element exhibits a diameter of less than 100 µm and/or less than 75 µm and/or less than 50 µm and/or less than 25 µm and/or less than 10 µm and/or less than 5 µm and/or less than 1 µm as measured according to the Diameter Test Method described herein. In another example, the fibrous element of the present disclosure exhibits a diameter of greater than 1 µm as measured according to the Diameter Test Method described herein. The diameter of a fibrous element of the present disclosure may be used to control the rate of release of one or more active agents present in the fibrous element and/or the rate of loss and/or altering of the fibrous element's physical structure.

The fibrous element may comprise two or more different active agents. In one example, the fibrous element comprises two or more different active agents, wherein the two or more different active agents are compatible with one another. In another example, the fibrous element comprises two or more different active agents, wherein the two or more different active agents are incompatible with one another.

In one example, the fibrous element may comprise an active agent within the fibrous element and an active agent on an external surface of the fibrous element, such as an active agent coating on the fibrous element. The active agent on the external surface of the fibrous element may be the same or different from the active agent present in the fibrous element. If different, the active agents may be compatible or incompatible with one another.

In another example, the fibrous structure or article of the present disclosure may comprise a coating on the external fibrous elements or filaments on one of the surfaces of the plies of the article. The coating may be applied to a surface of a ply and the surface with the coating may be an outer surface of the overall article or may be a surface internal to the article. Placement of the coating depends upon the benefit or active agent desired to be delivered. For example, coatings on an outer surface ply of the article would be more readily visible to a consumer, as it is on a consumer viewable surface. A coating on internal surface ply of the article may be less visible, as it may be hidden from direct view by a consumer. Placement of the coating on an internal surface and/or an outer surface of the article will be achieved as part of the article making process. A coating on an internal surface ply may be different or the same as coatings on the outer surface of the article. In one example, an article may have coatings on outer surfaces and/or internal surfaces of the article. In another example, an article may have coatings on outer surfaces and/or internal surfaces of plies making up the article. In yet another example, an article may have a silicone active agent comprising a coating or an aminosilicone comprising a coating on outer surfaces and/or internal surfaces of plies making up the article.

In one example, one or more active agents may be uniformly distributed or substantially uniformly distributed throughout the fibrous element. In another example, one or more active agents may be distributed as discrete regions within the fibrous element. In still another example, at least one active agent is distributed uniformly or substantially uniformly throughout the fibrous element and at least one other active agent is distributed as one or more discrete regions within the fibrous element. In still yet another example, at least one active agent is distributed as one or more discrete regions within the fibrous element and at least one other active agent is distributed as one or more discrete regions different from the first discrete regions within the fibrous element.

Filament-Forming Material

The filament-forming material is any suitable material, such as a polymer or monomers capable of producing a polymer that exhibits properties suitable for making a filament, such as by a spinning process.

In one example, the filament-forming material may comprise a polar solvent-soluble material, such as an alcohol-soluble material and/or a water-soluble material.

In another example, the filament-forming material may comprise a non-polar solvent-soluble material.

In still another example, the filament-forming material may comprise a water-soluble material and be free (less than 5% and/or less than 3% and/or less than 1% and/or 0% by weight on a dry fibrous element basis and/or dry fibrous structure basis) of water-insoluble materials.

In yet another example, the filament-forming material may be a film-forming material. In still yet another example, the filament-forming material may be synthetic or of natural origin and it may be chemically, enzymatically, and/or physically modified.

In even another example of the present disclosure, the filament-forming material may comprise a polymer selected from the group consisting of: polymers derived from acrylic monomers such as the ethylenically unsaturated carboxylic monomers and ethylenically unsaturated monomers, polyvinyl alcohol, polyvinylformamide, polyvinylamine, polyacrylates, polymethacrylates, copolymers of acrylic acid and methyl acrylate, polyvinylpyrrolidones, polyalkylene oxides, starch and starch derivatives, pullulan, gelatin, and cellulose derivatives (for example, hydroxypropylmethyl celluloses, methyl celluloses, carboxymethy celluloses).

In still another example, the filament-forming material may comprises a polymer selected from the group consisting of: polyvinyl alcohol, polyvinyl alcohol derivatives, starch, starch derivatives, cellulose derivatives, hemicellulose, hemicellulose derivatives, proteins, sodium alginate, hydroxypropyl methylcellulose, chitosan, chitosan derivatives, polyethylene glycol, tetramethylene ether glycol, polyvinyl pyrrolidone, hydroxymethyl cellulose, hydroxyethyl cellulose, carboxymethyl cellulose, and mixtures thereof.

In another example, the filament-forming material comprises a polymer is selected from the group consisting of: pullulan, hydroxypropylmethyl cellulose, hydroxyethyl cellulose, hydroxypropyl cellulose, polyvinyl pyrrolidone, carboxymethylcellulose, sodium alginate, xanthan gum, tragacanth gum, guar gum, acacia gum, Arabic gum, polyacrylic acid, methylmethacrylate copolymer, carboxyvinyl polymer, dextrin, pectin, chitin, levan, elsinan, collagen, gelatin, zein, gluten, soy protein, casein, polyvinyl alcohol, carboxylated polyvinyl alcohol, sulfonated polyvinyl alcohol, starch, starch derivatives, hemicellulose, hemicellulose derivatives, proteins, chitosan, chitosan derivatives, polyethylene glycol, tetramethylene ether glycol, hydroxymethyl cellulose, and mixtures thereof.

Water-Soluble Materials

Non-limiting examples of water-soluble materials include water-soluble polymers. The water-soluble polymers may be synthetic or natural original and may be chemically and/or physically modified. In one example, the polar solvent-soluble polymers exhibit a weight average molecular weight of at least 10,000 g/mol and/or at least 20,000 g/mol and/or at least 40,000 g/mol and/or at least 80,000 g/mol and/or at least 100,000 g/mol and/or at least 1,000,000 g/mol and/or at least 3,000,000 g/mol and/or at least 10,000,000 g/mol and/or at least 20,000,000 g/mol and/or to about 40,000,000 g/mol and/or to about 30,000,000 g/mol.

Non-limiting examples of water-soluble polymers include water-soluble hydroxyl polymers, water-soluble thermoplastic polymers, water-soluble biodegradable polymers, water-soluble non-biodegradable polymers and mixtures thereof. In one example, the water-soluble polymer comprises polyvinyl alcohol. In another example, the water-soluble polymer comprises starch. In yet another example, the water-soluble polymer comprises polyvinyl alcohol and starch. In yet another example, the water-soluble polymer comprises carboxymethyl cellulose. An yet in another example, the polymer comprise carboxymethyl cellulose and polyvinyl alcohol.

a. Water-soluble Hydroxyl Polymers—Non-limiting examples of water-soluble hydroxyl polymers in accordance with the present disclosure include polyols, such as polyvinyl alcohol, polyvinyl alcohol derivatives, polyvinyl alcohol copolymers, starch, starch derivatives, starch copolymers, chitosan, chitosan derivatives, chitosan copolymers, cellulose derivatives such as cellulose ether and ester derivatives, cellulose copolymers, hemicellulose, hemicellulose derivatives, hemicellulose copolymers, gums, arabinans, galactans, proteins, carboxymethylcellulose, and various other polysaccharides and mixtures thereof.

In one example, a water-soluble hydroxyl polymer of the present disclosure comprises a polysaccharide.

"Polysaccharides" as used herein means natural polysaccharides and polysaccharide derivatives and/or modified polysaccharides. Suitable water-soluble polysaccharides include, but are not limited to, starches, starch derivatives, chitosan, chitosan derivatives, cellulose derivatives, hemicellulose, hemicellulose derivatives, gums, arabinans, galactans and mixtures thereof. The water-soluble polysaccharide may exhibit a weight average molecular weight of from about 10,000 to about 40,000,000 g/mol and/or greater than 100,000 g/mol and/or greater than 1,000,000 g/mol and/or greater than 3,000,000 g/mol and/or greater than 3,000,000 to about 40,000,000 g/mol.

The water-soluble polysaccharides may comprise non-cellulose and/or non-cellulose derivative and/or non-cellulose copolymer water-soluble polysaccharides. Such non-cellulose water-soluble polysaccharides may be selected from the group consisting of: starches, starch derivatives, chitosan, chitosan derivatives, hemicellulose, hemicellulose derivatives, gums, arabinans, galactans and mixtures thereof.

In another example, a water-soluble hydroxyl polymer of the present disclosure comprises a non-thermoplastic polymer.

The water-soluble hydroxyl polymer may have a weight average molecular weight of from about 10,000 g/mol to about 40,000,000 g/mol and/or greater than 100,000 g/mol and/or greater than 1,000,000 g/mol and/or greater than 3,000,000 g/mol and/or greater than 3,000,000 g/mol to about 40,000,000 g/mol. Higher and lower molecular weight water-soluble hydroxyl polymers may be used in combination with hydroxyl polymers having a certain desired weight average molecular weight.

Well known modifications of water-soluble hydroxyl polymers, such as natural starches, include chemical modifications and/or enzymatic modifications. For example, natural starch can be acid-thinned, hydroxy-ethylated, hydroxy-propylated, and/or oxidized. In addition, the water-soluble hydroxyl polymer may comprise dent corn starch.

Naturally occurring starch is generally a mixture of linear amylose and branched amylopectin polymer of D-glucose units. The amylose is a substantially linear polymer of D-glucose units joined by $(1,4)$-α-D links. The amylopectin is a highly branched polymer of D-glucose units joined by $(1,4)$-α-D links and $(1,6)$-α-D links at the branch points. Naturally occurring starch typically contains relatively high levels of amylopectin, for example, corn starch (64-80% amylopectin), waxy maize (93-100% amylopectin), rice (83-84% amylopectin), potato (about 78% amylopectin), and wheat (73-83% amylopectin). Though all starches are potentially useful herein, the present disclosure is most commonly practiced with high amylopectin natural starches derived from agricultural sources, which offer the advantages of being abundant in supply, easily replenishable and inexpensive.

As used herein, "starch" includes any naturally occurring unmodified starches, modified starches, synthetic starches and mixtures thereof, as well as mixtures of the amylose or amylopectin fractions; the starch may be modified by physical, chemical, or biological processes, or combinations thereof. The choice of unmodified or modified starch for the present disclosure may depend on the end product desired. In one example of the present disclosure, the starch or starch mixture useful in the present disclosure has an amylopectin content from about 20% to about 100%, more typically from about 40% to about 90%, even more typically from about 60% to about 85% by weight of the starch or mixtures thereof.

Suitable naturally occurring starches can include, but are not limited to, corn starch, potato starch, sweet potato starch, wheat starch, sago palm starch, tapioca starch, rice starch, soybean starch, arrow root starch, amioca starch, bracken starch, lotus starch, waxy maize starch, and high amylose corn starch. Naturally occurring starches particularly, corn starch and wheat starch, are the preferred starch polymers due to their economy and availability.

Polyvinyl alcohols herein can be grafted with other monomers to modify its properties. A wide range of monomers has been successfully grafted to polyvinyl alcohol. Non-limiting examples of such monomers include vinyl acetate, styrene, acrylamide, acrylic acid, 2-hydroxyethyl methacrylate, acrylonitrile, 1,3-butadiene, methyl methacrylate, methacrylic acid, maleic acid, itaconic acid, sodium vinylsulfonate, sodium allylsulfonate, sodium methylallyl sulfonate, sodium phenylallylether sulfonate, sodium phenylmethallylether sulfonate, 2-acrylamido-methyl propane sulfonic acid (AMPs), vinylidene chloride, vinyl chloride, vinyl amine and a variety of acrylate esters.

In one example, the water-soluble hydroxyl polymer is selected from the group consisting of: polyvinyl alcohols, hydroxymethylcelluloses, hydroxyethylcelluloses, hydroxypropylmethylcelluloses, carboxymethylcelluloses, and mixtures thereof. A non-limiting example of a suitable polyvinyl alcohol includes those commercially available from Sekisui Specialty Chemicals America, LLC (Dallas, TX) under the CELVOL® trade name. Another non-limiting example of a suitable polyvinyl alcohol includes G Polymer commercially available from Nippon Ghosei. A non-limiting example of a suitable hydroxypropylmethylcellulose includes those commercially available from the Dow Chemical Company (Midland, MI) under the METHOCEL® trade name including combinations with above mentioned polyvinyl alcohols.

b. Water-soluble Thermoplastic Polymers—Non-limiting examples of suitable water-soluble thermoplastic polymers include thermoplastic starch and/or starch derivatives, polylactic acid, polyhydroxyalkanoate, polycaprolactone, polyesteramides and certain polyesters, and mixtures thereof.

The water-soluble thermoplastic polymers of the present disclosure may be hydrophilic or hydrophobic. The water-soluble thermoplastic polymers may be surface treated and/or internally treated to change the inherent hydrophilic or hydrophobic properties of the thermoplastic polymer.

The water-soluble thermoplastic polymers may comprise biodegradable polymers.

Any suitable weight average molecular weight for the thermoplastic polymers may be used. For example, the weight average molecular weight for a thermoplastic polymer in accordance with the present disclosure is greater than about 10,000 g/mol and/or greater than about 40,000 g/mol and/or greater than about 50,000 g/mol and/or less than about 500,000 g/mol and/or less than about 400,000 g/mol and/or less than about 200,000 g/mol.

Active Agents

Active agents are a class of additives that are designed and intended to provide a benefit to something other than the fibrous element and/or particle and/or fibrous structure itself, such as providing a benefit to an environment external to the fibrous element and/or particle and/or fibrous structure. Active agents may be any suitable additive that produces an intended effect under intended use conditions of the fibrous element. For example, the active agent may be selected from the group consisting of: personal cleansing and/or conditioning agents such as hair care agents such as shampoo agents and/or hair colorant agents, hair conditioning agents, skin care agents, sunscreen agents, and skin conditioning agents; laundry care and/or conditioning agents such as fabric care agents, fabric conditioning agents, fabric softening agents, fabric anti-wrinkling agents, fabric care anti-static agents, fabric care stain removal agents, soil release agents, dispersing agents, suds suppressing agents, suds boosting agents, anti-foam agents, and fabric refreshing agents; liquid and/or powder dishwashing agents (for hand dishwashing and/or automatic dishwashing machine applications), hard surface care agents, and/or conditioning agents and/or polishing agents; other cleaning and/or conditioning agents such as antimicrobial agents, antibacterial agents, antifungal agents, fabric hueing agents, perfume, bleaching agents (such as oxygen bleaching agents, hydrogen peroxide, percarbonate bleaching agents, perborate bleaching agents, chlorine bleaching agents), bleach activating agents, chelating agents, builders, lotions, brightening agents, air care agents, carpet care agents, dye transfer-inhibiting agents, clay soil removing agents, anti-redeposition agents, polymeric soil release agents, polymeric dispersing agents, alkoxylated polyamine polymers, alkoxylated polycarboxylate polymers, amphilic graft copolymers, dissolution aids, buffering systems, water-softening agents, water-hardening agents, pH adjusting agents, enzymes, flocculating agents, effervescent agents, preservatives, cosmetic agents, make-up removal agents, lathering agents, deposition aid agents, coacervate-forming agents, clays, thickening agents, latexes, silicas, drying agents, odor control agents, antiperspirant agents, cooling agents, warming agents, absorbent gel agents, anti-inflammatory agents, dyes, pigments, acids, and bases; liquid treatment active agents; agricultural active agents; industrial active agents; ingestible active agents such as medicinal agents, teeth whitening agents, tooth care agents, mouthwash agents, periodontal gum care agents, edible agents, dietary agents, vitamins, minerals; water-treatment agents such as water clarifying and/or water disinfecting agents, and mixtures thereof.

Non-limiting examples of suitable cosmetic agents, skin care agents, skin conditioning agents, hair care agents, and hair conditioning agents are described in CTFA Cosmetic Ingredient Handbook, Second Edition, The Cosmetic, Toiletries, and Fragrance Association, Inc. 1988, 1992.

One or more classes of chemicals may be useful for one or more of the active agents listed above. For example, surfactants may be used for any number of the active agents described above. Likewise, bleaching agents may be used for fabric care, hard surface cleaning, dishwashing and even teeth whitening. Therefore, one of ordinary skill in the art will appreciate that the active agents will be selected based upon the desired intended use of the fibrous element and/or particle and/or fibrous structure made therefrom.

For example, if the fibrous element and/or particle and/or fibrous structure made therefrom is to be used for hair care and/or conditioning then one or more suitable surfactants, such as a lathering surfactant could be selected to provide the desired benefit to a consumer when exposed to conditions of intended use of the fibrous element and/or particle and/or fibrous structure incorporating the fibrous element and/or particle.

In one example, if the fibrous element and/or particle and/or fibrous structure made therefrom is designed or intended to be used for laundering clothes in a laundry operation, then one or more suitable surfactants and/or enzymes and/or builders and/or perfumes and/or suds suppressors and/or bleaching agents could be selected to provide the desired benefit to a consumer when exposed to conditions of intended use of the fibrous element and/or particle and/or fibrous structure incorporating the fibrous element and/or particle. In another example, if the fibrous element and/or particle and/or fibrous structure made therefrom is designed to be used for laundering clothes in a laundry operation and/or cleaning dishes in a dishwashing operation, then the fibrous element and/or particle and/or fibrous structure may comprise a laundry detergent composition or dishwashing detergent composition or active agents used in such compositions.

In one example, the active agent comprises a non-perfume active agent. In another example, the active agent comprises a non-surfactant active agent. In still another example, the active agent comprises a non-ingestible active agent, in other words an active agent other than an ingestible active agent.

Surfactants

Non-limiting examples of suitable surfactants include anionic surfactants, cationic surfactants, nonionic surfactants, zwitterionic surfactants, amphoteric surfactants, and mixtures thereof. Co-surfactants may also be included in the fibrous elements and/or particles. For fibrous elements and/or particles designed for use as laundry detergents and/or dishwashing detergents, the total level of surfactants should be sufficient to provide cleaning including stain and/or odor removal, and generally ranges from about 0.5% to about 95%. Further, surfactant systems comprising two or more surfactants that are designed for use in fibrous elements and/or particles for laundry detergents and/or dishwashing detergents may include all-anionic surfactant systems, mixed-type surfactant systems comprising anionic-nonionic surfactant mixtures, or nonionic-cationic surfactant mixtures or low-foaming nonionic surfactants. In certain examples, surfactants included in the fibrous elements (e.g., filaments) can be different from surfactants included in the particles.

The surfactants herein can be linear or branched. In one example, suitable linear surfactants include those derived from agrochemical oils such as coconut oil, palm kernel oil, soybean oil, or other vegetable-based oils.

a. Anionic Surfactants

Non-limiting examples of suitable anionic surfactants include alkyl sulfates, alkyl ether sulfates, branched alkyl sulfates, branched alkyl alkoxylates, branched alkyl alkoxylate sulfates, mid-chain branched alkyl aryl sulfonates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, sodium lauroyl glutamate, and combinations thereof.

Alkyl sulfates and alkyl ether sulfates suitable for use herein include materials with the respective formula $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium and triethanolamine. Other suitable anionic surfactants are described in McCutcheon's Detergents and Emulsifiers, North American Edition (1986), Allured Publishing Corp. and McCutcheon's, Functional Materials, North American Edition (1992), Allured Publishing Corp.

In one example, anionic surfactants useful in the fibrous elements and/or particles of the present disclosure include $C_9$-$C_{15}$ alkyl benzene sulfonates (LAS), $C_8$-$C_{20}$ alkyl ether sulfates, for example alkyl poly(ethoxy) sulfates, $C_8$-$C_{20}$ alkyl sulfates, and mixtures thereof. Other anionic surfactants include methyl ester sulfonates (MES), secondary alkane sulfonates, methyl ester ethoxylates (MEE), sulfonated estolides, and mixtures thereof.

In another example, the anionic surfactant is selected from the group consisting of: $C_{11}$-$C_{18}$ alkyl benzene sulfonates ("LAS") and primary, branched-chain and random $C_{10}$-$C_{20}$ alkyl sulfates ("AS"), $C_{10}$-$C_{18}$ secondary (2,3) alkyl sulfates of the formula $CH_3(CH_2)_x(CHOSO_3^-M^+)$ $CH_3$ and $CH_3$ $(CH_2)_y(CHOSO_3^-M^+)$ $CH_2CH_3$ where x and (y+1) are integers of at least about 7, preferably at least about 9, and M is a water-solubilizing cation, especially sodium, unsaturated sulfates such as oleyl sulfate, the $C_{10}$-$C_{18}$ alpha-sulfonated fatty acid esters, the $C_{10}$-$C_{18}$ sulfated alkyl polyglycosides, the $C_{10}$-$C_{18}$ alkyl alkoxy sulfates ("$AE_xS$") wherein x is from 1-30, and $C_{10}$-$C_{18}$ alkyl alkoxy carboxylates, for example comprising 1-5 ethoxy units, mid-chain branched alkyl sulfates as discussed in U.S. Pat. Nos. 6,020,303 and 6,060,443; mid-chain branched alkyl alkoxy sulfates as discussed in U.S. Pat. Nos. 6,008,181 and 6,020,303; modified alkylbenzene sulfonate (MLAS) as discussed in WO 99/05243, WO 99/05242 and WO 99/05244; methyl ester sulfonate (MES); and alpha-olefin sulfonate (AOS).

b. Cationic Surfactants

Non-limiting examples of suitable cationic surfactants include, but are not limited to, those having the formula (I):

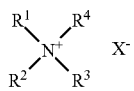

I in which $R^1$, $R^2$, $R^3$, and $R^4$ are each independently selected from (a) an aliphatic group of from 1 to 26 carbon atoms, or (b) an aromatic, alkoxy, polyoxyalkylene, alkylcarboxy, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate, nitrate, sulphate, and alkylsulphate radicals. In one example, the alkylsulphate radical is methosulfate and/or ethosulfate.

Suitable quaternary ammonium cationic surfactants of general formula (I) may include cetyltrimethylammonium chloride, behenyltrimethylammonium chloride (BTAC), stearyltrimethylammonium chloride, cetylpyridinium chloride, octadecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, didecyldimehtylammonium chloride, dioctadecyldimethylammonium chloride, distearyldimethylammonium chloride, tallowtrimethylammonium chloride, cocotrimethylammonium chloride, 2-ethylhexyl-stearyldimethylammonum chloride, dipalmitoylethyldimethylammonium chloride, ditallowoylethyldimethylammonium chloride, distearoylethyldimethylammonium methosulfate, PEG-2 oleylammonium chloride and salts of these, where the chloride is replaced by halogen, (e.g., bromide), acetate, citrate, lactate, glycolate, phosphate nitrate, sulphate, or alkylsulphate.

Non-limiting examples of suitable cationic surfactants are commercially available under the trade names ARQUAD® from Akzo Nobel Surfactants (Chicago, IL).

In one example, suitable cationic surfactants include quaternary ammonium surfactants, for example that have up to 26 carbon atoms include: alkoxylate quaternary ammonium (AQA) surfactants as discussed in U.S. Pat. No. 6,136,769; dimethyl hydroxyethyl quaternary ammonium as discussed in 6,004,922; dimethyl hydroxyethyl lauryl ammonium chloride; polyamine cationic surfactants as discussed in WO 98/35002, WO 98/35003, WO 98/35004, WO 98/35005, and WO 98/35006; cationic ester surfactants as discussed in U.S. Pat. Nos. 4,228,042, 4,239,660 4,260,529 and U.S. Pat. No. 6,022,844; and amino surfactants as discussed in U.S. Pat. No. 6,221,825 and WO 00/47708, for example amido propyldimethyl amine (APA).

In one example the cationic ester surfactants are hydrolyzable under the conditions of a laundry wash.

c. Nonionic Surfactants

Non-limiting examples of suitable nonionic surfactants include alkoxylated alcohols (AE's) and alkyl phenols, polyhydroxy fatty acid amides (PFAA's), alkyl polyglycosides (APG's), $C_{10}$-$C_{18}$ glycerol ethers, and the like.

In one example, non-limiting examples of nonionic surfactants useful in the present disclosure include: $C_{12}$-$C_{18}$ alkyl ethoxylates, such as, NEODOL® nonionic surfactants from Shell; $C_6$-$C_{12}$ alkyl phenol alkoxylates wherein the alkoxylate units are a mixture of ethyleneoxy and propyleneoxy units; $C_{12}$-Cis alcohol and $C_6$-$C_{12}$ alkyl phenol condensates with ethylene oxide/propylene oxide block alkyl polyamine ethoxylates such as PLURONIC® from BASF; $C_{14}$-$C_{22}$ mid-chain branched alcohols, BA, as discussed in U.S. Pat. No. 6,150,322; $C_{14}$-$C_{22}$ mid-chain branched alkyl alkoxylates, $BAE_x$, wherein x is from 1-30, as discussed in U.S. Pat. Nos. 6,153,577, 6,020,303 and 6,093,856; alkylpolysaccharides as discussed in U.S. Pat. No. 4,565,647 Llenado, issued Jan. 26, 1986; specifically alkylpolyglycosides as discussed in U.S. Pat. Nos. 4,483,780 and 4,483,779; polyhydroxy detergent acid amides as discussed in U.S. Pat. No. 5,332,528; and ether capped poly(oxyalkylated) alcohol surfactants as discussed in U.S. Pat. No. 6,482,994 and WO 01/42408.

Examples of commercially available nonionic surfactants suitable for the present disclosure include: Tergitol® 15-S-9 (the condensation product of $C_{11}$-$C_{15}$ linear alcohol with 9 moles ethylene oxide) and Tergitol® 24-L-6 NMW (the condensation product of $C_{12}$-$C_{14}$ primary alcohol with 6 moles ethylene oxide with a narrow molecular weight distribution), both marketed by Dow Chemical Company; Neodol® 45-9 (the condensation product of $C_{14}$-$C_{15}$ linear alcohol with 9 moles of ethylene oxide), Neodol® 23-3 (the condensation product of $C_{12}$-$C_{13}$ linear alcohol with 3 moles of ethylene oxide), Neodol® 45-7 (the condensation product of $C_{14}$-$C_{15}$ linear alcohol with 7 moles of ethylene oxide) and Neodol® 45-5 (the condensation product of $C_{14}$-$C_{15}$ linear alcohol with 5 moles of ethylene oxide) marketed by Shell Chemical Company; Kyro® EOB (the condensation product of $C_{13}$-$C_{15}$ alcohol with 9 moles ethylene oxide), marketed by The Procter & Gamble Company; and Genapol LA 030 or 050 (the condensation product of $C_{12}$-$C_{14}$ alcohol with 3 or 5 moles of ethylene oxide) marketed by Clariant. The nonionic surfactants may exhibit an HLB range of from about 8 to about 17 and/or from about 8 to about 14. Condensates with propylene oxide and/or butylene oxides may also be used.

Polyethylene, polypropylene, and polybutylene oxide condensates of alkyl phenols are also suitable for use as a nonionic surfactant in the present disclosure. These compounds include the condensation products of alkyl phenols having an alkyl group containing from about 6 to about 14 carbon atoms, in either a straight-chain or branched-chain configuration with the alkylene oxide. Commercially available nonionic surfactants of this type include Igepal®

CO-630, marketed by Solvay-Rhodia; and Triton® X-45, X-114, X-100 and X-102, all marketed by the Dow Chemical Company.

For automatic dishwashing applications, low foaming nonionic surfactants may be used. Suitable low foaming nonionic surfactants are disclosed in U.S. Pat. No. 7,271,138 col. 7, line 10 to col. 7, line 60.

Examples of other suitable nonionic surfactants are the commercially-available Pluronic® surfactants, marketed by BASF, the commercially available Tetronic® compounds, marketed by BASF, and the commercially available Plurafac® surfactants, marketed by BASF.

d. Zwitterionic Surfactants

Non-limiting examples of zwitterionic or ampholytic surfactants include: derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 at column 19, line 38 through column 22, line 48, for examples of zwitterionic surfactants; betaines, including alkyl dimethyl betaine and cocodimethyl amidopropyl betaine, $C_8$ to $C_{18}$ (for example from $C_{12}$ to $C_{18}$) amine oxides and sulfo and hydroxy betaines, such as N-alkyl-N,N-dimethylammino-1-propane sulfonate where the alkyl group can be $C_8$ to $C_{18}$ and in certain examples from $C_{10}$ to $C_{14}$.

e Amphoteric Surfactants

Non-limiting examples of amphoteric surfactants include: aliphatic derivatives of secondary or tertiary amines, or aliphatic derivatives of heterocyclic secondary and tertiary amines in which the aliphatic radical can be straight- or branched-chain and mixtures thereof. One of the aliphatic substituents may contain at least about 8 carbon atoms, for example from about 8 to about 18 carbon atoms, and at least one contains an anionic water-solubilizing group, e.g. carboxy, sulfonate, sulfate. See U.S. Pat. No. 3,929,678 at column 19, lines 18-35, for suitable examples of amphoteric surfactants.

Perfumes

One or more perfume and/or perfume raw materials such as accords and/or notes may be incorporated into one or more of the fibrous elements and/or particles of the present disclosure. The perfume may comprise a perfume ingredient selected from the group consisting of: aldehyde perfume ingredients, ketone perfume ingredients, and mixtures thereof.

One or more perfumes and/or perfumery ingredients may be included in the fibrous elements and/or particles of the present disclosure. A wide variety of natural and synthetic chemical ingredients useful as perfumes and/or perfumery ingredients include but not limited to aldehydes, ketones, esters, and mixtures thereof. Also included are various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. In one example, a finished perfume typically comprises from about 0.01% to about 10% and/or from about 0.01% to about 8% and/or from about 0.01% to about 6% and/or from about 0.01% to about 4% and/or from about 0.01% to about 2% and/or from about 0.05% to about 2% by weight on a dry fibrous element basis and/or a dry particle basis and/or dry fibrous structure basis.

Perfume Delivery Systems

Certain perfume delivery systems, methods of making certain perfume delivery systems and the uses of such perfume delivery systems are disclosed in USPA 2007/0275866 A1. Non-limiting examples of perfume delivery systems include the following:

I. Polymer Assisted Delivery (PAD): This perfume delivery technology uses polymeric materials to deliver perfume materials. Classical coacervation, water soluble or partly soluble to insoluble charged or neutral polymers, liquid crystals, hot melts, hydrogels, perfumed plastics, microcapsules, nano- and micro-latexes, polymeric film formers, and polymeric absorbents, polymeric adsorbents, etc. are some examples. PAD includes but is not limited to:

a.) Matrix Systems: The fragrance is dissolved or dispersed in a polymer matrix or particle. Perfumes, for example, may be 1) dispersed into the polymer prior to formulating into the product or 2) added separately from the polymer during or after formulation of the product. Diffusion of perfume from the polymer is a common trigger that allows or increases the rate of perfume release from a polymeric matrix system that is deposited or applied to the desired surface (situs), although many other triggers are know that may control perfume release. Absorption and/or adsorption into or onto polymeric particles, films, solutions, and the like are aspects of this technology. Nano- or microparticles composed of organic materials (e.g., latexes) are examples. Suitable particles include a wide range of materials including, but not limited to polyacetal, polyacrylate, polyacrylic, polyacrylonitrile, polyamide, polyaryletherketone, polybutadiene, polybutylene, polybutylene terephthalate, polychloroprene, polyethylene, polyethylene terephthalate, polycyclohexylene dimethylene terephthalate, polycarbonate, polychloroprene, polyhydroxyalkanoate, polyketone, polyester, polyethylene, polyetherimide, polyethersulfone, polyethylenechlorinates, polyimide, polyisoprene, polylactic acid, polymethylpentene, polyphenylene oxide, polyphenylene sulfide, polyphthalamide, polypropylene, polystyrene, polysulfone, polyvinyl acetate, polyvinyl chloride, as well as polymers or copolymers based on acrylonitrile-butadiene, cellulose acetate, ethylene-vinyl acetate, ethylene vinyl alcohol, styrene-butadiene, vinyl acetate-ethylene, and mixtures thereof.

"Standard" systems refer to those that are "pre-loaded" with the intent of keeping the pre-loaded perfume associated with the polymer until the moment or moments of perfume release. Such polymers may also suppress the neat product odor and provide a bloom and/or longevity benefit depending on the rate of perfume release. One challenge with such systems is to achieve the ideal balance between 1) in-product stability (keeping perfume inside carrier until you need it) and 2) timely release (during use or from dry situs). Achieving such stability is particularly important during in-product storage and product aging. This challenge is particularly apparent for aqueous-based, surfactant-containing products, such as heavy duty liquid laundry detergents. Many "Standard" matrix systems available effectively become "Equilibrium" systems when formulated into aqueous-based products. One may select an "Equilibrium" system or a Reservoir system, which has acceptable in-product diffusion stability and available triggers for release (e.g., friction). "Equilibrium" systems are those in which the perfume and polymer may be added separately to the product, and the equilibrium interaction between perfume and polymer leads to a benefit at one or more consumer touch points (versus a free perfume control that has no polymer-assisted delivery technology). The polymer may also be pre-loaded with perfume; however, part or all of the perfume may diffuse during in-product storage reaching an equilibrium that includes having desired perfume raw materials (PRMs) associated with the polymer. The polymer then carries the perfume to the surface, and release is typically via perfume diffusion. The use of such equilibrium system polymers has the potential to decrease the neat product odor intensity of the neat product (usually more so in the case of pre-loaded standard system). Deposition of such polymers may serve to "flatten" the release profile and provide increased longevity. As indicated above, such longevity would be achieved by suppressing the initial intensity and may enable the formulator to use more high impact or low odor detection threshold (ODT) or low Kovats Index (KI) PRMs to achieve initial product odor benefits without initial intensity that is too strong or distorted. It is important that perfume release occurs within the time frame of the application to impact the desired consumer touch point or touch points. Suitable micro-particles and micro-latexes as well as methods of making same may be found in USPA 2005/0003980 A1. Matrix systems also include hot melt adhesives and perfume plastics. In addition, hydrophobically modified polysaccharides may be formulated into the perfumed product to increase perfume deposition and/or modify perfume release. All such matrix systems, including for example polysaccharides and nanolatexes may be combined with other PDTs, including other PAD systems such as PAD reservoir systems in the form of a perfume microcapsule (PMC). Polymer Assisted Delivery (PAD) matrix systems may include those described in the following references: US Patent Applications 2004/0110648 A1; 2004/0092414 A1; 2004/0091445 A1 and 2004/0087476 A1; and U.S. Pat. Nos. 6,531,444; 6,024,943; 6,042,792; 6,051,540; 4,540,721 and 4,973,422.

Silicones are also examples of polymers that may be used as PDT, and can provide perfume benefits in a manner similar to the polymer-assisted delivery "matrix system". Such a PDT is referred to as silicone-assisted delivery (SAD). One may pre-load silicones with perfume, or use them as an equilibrium system as described for PAD. Suitable silicones as well as making same may be found in WO 2005/102261; USPA 20050124530A1; USPA 20050143282A1; and WO 2003/015736. Functionalized silicones may also be used as described in US 2006/003913 A1. Examples of silicones include polydimethylsiloxane and polyalkyldimethylsiloxanes. Other examples include those with amine functionality, which may be used to provide benefits associated with amine-assisted delivery (AAD) and/or polymer-assisted delivery (PAD) and/or amine-reaction products (ARP). Other such examples may be found in U.S. Pat. No. 4,911,852; USPA 2004/0058845 A1; USPA 2004/0092425 A1 and USPA 2005/0003980 A1.

b.) Reservoir Systems: Reservoir systems are also known as a core-shell type technology, or one in which the fragrance is surrounded by a perfume release controlling membrane, which may serve as a protective shell. The material inside the microcapsule is referred to as the core, internal phase, or fill, whereas the wall is sometimes called a shell, coating, or membrane. Microparticles or pressure sensitive capsules or microcapsules are examples of this technology. Microcapsules of the present disclosure are formed by a variety of procedures that include, but are not limited to, coating, extrusion, spray-drying, interfacial, in-situ and matrix polymerization. The possible shell materials vary widely in their stability toward water. Among the most stable are polyoxymethyleneurea (PMU)-based materials, which may hold certain PRMs for even long periods of time in aqueous solution (or product). Such systems include but are not limited to urea-formaldehyde and/or melamine-formaldehyde. Stable shell materials include polyacrylate-based materials obtained as reaction product of an oil soluble or dispersible amine with a multifunctional acrylate or methacrylate monomer or oligomer, an oil soluble acid and an initiator, in presence of an anionic emulsifier comprising a water soluble or water dispersible acrylic acid alkyl acid copolymer, an alkali or alkali salt. Gelatin-based microcapsules may be prepared so that they dissolve quickly or slowly in water, depending for example on the degree of cross-linking. Many other capsule wall materials are available and vary in the degree of perfume diffusion stability observed. Without wishing to be bound by theory, the rate of release of perfume from a capsule, for example, once deposited on a surface is typically in reverse order of in-product perfume diffusion stability. As such, urea-formaldehyde and melamine-formaldehyde microcapsules for example, typically require a release mechanism other than, or in addition to, diffusion for release, such as mechanical force (e.g., friction, pressure, shear stress) that serves to break the capsule and increase the rate of perfume (fragrance) release. Other triggers include melting, dissolution, hydrolysis or other chemical reaction, electromagnetic radiation, and the like. The use of pre-loaded microcapsules requires the proper ratio of in-product stability and in-use and/or on-surface (on-situs) release, as well as proper selection of PRMs. Microcapsules that are based on urea-formaldehyde and/or melamine-formaldehyde are relatively stable, especially in near neutral aqueous-based solutions. These materials may require a friction trigger which may not be applicable to all product applications. Other microcapsule materials (e.g., gelatin) may be unstable in aqueous-based products and may even provide reduced benefit (versus free perfume control) when in-product aged. Scratch and sniff technologies are yet another example of PAD. Perfume microcapsules (PMC) may include those described in the following references: US Patent Applications: 2003/0125222 A1; 2003/215417 A1; 2003/216488 A1; 2003/158344 A1; 2003/165692 A1; 2004/071742 A1; 2004/071746 A1; 2004/072719 A1; 2004/072720 A1; 2006/0039934 A1; 2003/203829 A1; 2003/195133 A1; 2004/087477 A1; 2004/0106536 A1; and U.S. Pat. Nos. 6,645,479 B1; 6,200,949 B1; 4,882,220; 4,917,920; 4,514,461; 6,106,875 and 4,234,627, 3,594,328 and US RE 32713, PCT Patent Application: WO 2009/134234 A1, WO 2006/127454 A2, WO 2010/079466 A2, WO 2010/079467 A2, WO 2010/079468 A2, WO 2010/084480 A2.

II. Molecule-Assisted Delivery (MAD): Non-polymer materials or molecules may also serve to improve the delivery of perfume. Without wishing to be bound by theory, perfume may non-covalently interact with organic materials, resulting in altered deposition and/or release. Non-limiting examples of such organic materials include but are not limited to hydrophobic materials such as organic oils, waxes, mineral oils, petrolatum, fatty acids or esters, sugars, surfactants, liposomes and even other perfume raw material (perfume oils), as well as natural oils, including body and/or other soils. Perfume fixatives are yet another example. In one aspect, non-polymeric materials or molecules have a CLogP greater than about 2. Molecule-Assisted Delivery (MAD) may also include those described in U.S. Pat. Nos. 7,119,060 and 5,506,201.

III. Fiber-Assisted Delivery (FAD): The choice or use of a situs itself may serve to improve the delivery of perfume. In fact, the situs itself may be a perfume delivery technology. For example, different fabric types such as cotton or polyester will have different properties with respect to ability to attract and/or retain and/or release perfume. The amount of perfume deposited on or in fibers may be altered by the choice of fiber, and also by the history or treatment of the fiber, as well as by any fiber coatings or treatments. Fibers may be woven and non-woven as well as natural or synthetic. Natural fibers include those produced by plants, animals, and geological processes, and include but are not limited to cellulose materials such as cotton, linen, hemp jute, flax, ramie, and sisal, and fibers used to manufacture paper and cloth. Fiber-Assisted Delivery may consist of the use of wood fiber, such as thermomechanical pulp and bleached or unbleached kraft or sulfite pulps. Animal fibers consist largely of particular proteins, such as silk, feathers, sinew, catgut and hair (including wool). Polymer fibers based on synthetic chemicals include but are not limited to polyamide nylon, PET or PBT polyester, phenol-formaldehyde (PF), polyvinyl alcohol fiber (PVOH), polyvinyl chloride fiber (PVC), polyolefins (PP and PE), and acrylic polymers. All such fibers may be pre-loaded with a perfume, and then added to a product that may or may not contain free perfume and/or one or more perfume delivery technologies. In one aspect, the fibers may be added to a product prior to being loaded with a perfume, and then loaded with a perfume by adding a perfume that may diffuse into the fiber, to the product. Without wishing to be bound by theory, the perfume may absorb onto or be adsorbed into the fiber, for example, during product storage, and then be released at one or more moments of truth or consumer touch points.

IV. Amine Assisted Delivery (AAD): The amine-assisted delivery technology approach utilizes materials that contain an amine group to increase perfume deposition or modify perfume release during product use. There is no requirement in this approach to pre-complex or pre-react the perfume raw material(s) and amine prior to addition to the product. In one aspect, amine-containing AAD materials suitable for use herein may be non-aromatic; for example, polyalkylimine, such as polyethyleneimine (PEI), or polyvinylamine (PVAm), or aromatic, for example, anthranilates. Such materials may also be polymeric or non-polymeric. In one aspect, such materials contain at least one primary amine. This technology will allow increased longevity and controlled release also of low ODT perfume notes (e.g., aldehydes, ketones, enones) via amine functionality, and delivery of other PRMs, without being bound by theory, via polymer-assisted delivery for polymeric amines Without technology, volatile top notes can be lost too quickly, leaving a higher ratio of middle and base notes to top notes. The use of a polymeric amine allows higher levels of top notes and other PRMS to be used to obtain freshness longevity without causing neat product odor to be more intense than desired, or allows top notes and other PRMs to be used more efficiently. In one aspect, AAD systems are effective at delivering PRMs at pH greater than about neutral. Without wishing to be bound by theory, conditions in which more of the amines of the AAD system are deprotonated may result in an increased affinity of the deprotonated amines for PRMs such as aldehydes and ketones, including unsaturated ketones and enones such as damascone. In another aspect, polymeric amines are effective at delivering PRMs at pH less than about neutral. Without wishing to be bound by theory, conditions in which more of the amines of the AAD system are protonated may result in a decreased affinity of the protonated amines for PRMs such as aldehydes and ketones, and a strong affinity of the polymer framework for a broad range of PRMs. In such an aspect, polymer-assisted delivery may be delivering more of the perfume benefit; such systems are a subspecies of AAD and may be referred to as Amine-Polymer-Assisted Delivery or APAD. In some cases when the APAD is employed in a composition that has a pH of less than seven, such APAD systems may also be considered Polymer-Assisted Delivery (PAD). In yet another aspect, AAD and PAD systems may interact with other materials, such as anionic surfactants or polymers to form coacervate and/or coacervates-like systems. In another aspect, a material that contains a heteroatom other than nitrogen, for example sulfur, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. Suitable AAD systems as well as methods of making same may be found in US Patent Applications 2005/0003980 A1; 2003/0199422 A1; 2003/0036489 A1; 2004/0220074 A1 and U.S. Pat. No. 6,103,678.

V. Cyclodextrin Delivery System (CD): This technology approach uses a cyclic oligosaccharide or cyclodextrin to improve the delivery of perfume. Typically a perfume and cyclodextrin (CD) complex is formed. Such complexes may be preformed, formed in-situ, or formed on or in the situs. Without wishing to be bound by theory, loss of water may serve to shift the equilibrium toward the CD-Perfume complex, especially if other adjunct ingredients (e.g., surfactant) are not present at high concentration to compete with the perfume for the cyclodextrin cavity. A bloom benefit may be achieved if water exposure or an increase in moisture content occurs at a later time point. In addition, cyclodextrin allows the perfume formulator increased flexibility in selection of PRMs. Cyclodextrin may be pre-loaded with perfume or added separately from perfume to obtain the desired perfume stability, deposition or release benefit. Suitable CDs as well as methods of making same may be found in USPA 2005/0003980 A1 and 2006/0263313 A1 and U.S. Pat. Nos. 5,552,378; 3,812,011; 4,317,881; 4,418,144 and 4,378,923.

VI. Starch Encapsulated Accord (SEA): The use of a starch encapsulated accord (SEA) technology allows one to modify the properties of the perfume, for example, by converting a liquid perfume into a solid by adding ingredients such as starch. The benefit includes increased perfume retention during product storage, especially under non-aqueous conditions. Upon exposure to moisture, a perfume bloom may be triggered. Benefits at other moments of truth may also be achieved because the starch allows the product formulator to select PRMs or PRM concentrations that normally cannot be used without the presence of SEA. Another technology example includes the use of other organic and inorganic materials, such as silica to convert perfume from liquid to solid. Suitable SEAs as well as methods of making same may be found in USPA 2005/0003980 A1 and U.S. Pat. No. 6,458,754 B1.

VII. Inorganic Carrier Delivery System (ZIC): This technology relates to the use of porous zeolites or other inorganic materials to deliver perfumes. Perfume-loaded zeolite may be used with or without adjunct ingredients used for example to coat the perfume-loaded zeolite (PLZ) to change its perfume release properties during product storage or during use or from the dry situs. Suitable zeolite and inorganic carriers as well as methods of making same may be found in USPA 2005/0003980 A1 and U.S. Pat. Nos. 5,858,959; 6,245,732 B1; 6,048,830 and 4,539,135. Silica is another form of ZIC. Another example of a suitable inorganic carrier includes inorganic tubules, where the perfume or other active material is contained within the lumen of the nano- or micro-tubules. In one aspect, the perfume-loaded inorganic tubule (or Perfume-Loaded Tubule or PLT) is a mineral nano- or micro-tubule, such as halloysite or mixtures of halloysite with other inorganic materials, including other clays. The PLT technology may also comprise additional ingredients on the inside and/or outside of the tubule for the purpose of improving in-product diffusion stability, deposition on the desired situs or for controlling the release rate of the loaded perfume. Monomeric and/or polymeric materials, including starch encapsulation, may be used to coat, plug, cap, or otherwise encapsulate the PLT. Suitable PLT systems as well as methods of making same may be found in U.S. Pat. No. 5,651,976.

VIII. Pro-Perfume (PP): This technology refers to perfume technologies that result from the reaction of perfume materials with other substrates or chemicals to form materials that have a covalent bond between one or more PRMs and one or more carriers. The PRM is converted into a new material called a pro-PRM (i.e., pro-perfume), which then may release the original PRM upon exposure to a trigger such as water or light. Pro-perfumes may provide enhanced perfume delivery properties such as increased perfume deposition, longevity, stability, retention, and the like. Pro-perfumes include those that are monomeric (non-polymeric) or polymeric, and may be pre-formed or may be formed in-situ under equilibrium conditions, such as those that may be present during in-product storage or on the wet or dry situs. Nonlimiting examples of pro-perfumes include Michael adducts (e.g., beta-amino ketones), aromatic or non-aromatic imines (Schiff bases), oxazolidines, beta-keto esters, and orthoesters. Another aspect includes compounds comprising one or more beta-oxy or beta-thio carbonyl moieties capable of releasing a PRM, for example, an alpha, beta-unsaturated ketone, aldehyde or carboxylic ester. The typical trigger for perfume release is exposure to water; although other triggers may include enzymes, heat, light, pH change, autoxidation, a shift of equilibrium, change in concentration or ionic strength and others. For aqueous-based products, light-triggered pro-perfumes are particularly suited. Such photo-pro-perfumes (PPPs) include but are not limited to those that release coumarin derivatives and perfumes and/or pro-perfumes upon being triggered. The released pro-perfume may release one or more PRMs by means of any of the above mentioned triggers. In one aspect, the photo-pro-perfume releases a nitrogen-based pro-perfume when exposed to a light and/or moisture trigger. In another aspect, the nitrogen-based pro-perfume, released from the photo-pro-perfume, releases one or more PRMs selected, for example, from aldehydes, ketones (including enones) and alcohols. In still another aspect, the PPP releases a dihydroxy coumarin derivative. The light-triggered pro-perfume may also be an ester that releases a coumarin derivative and a perfume alcohol. In one aspect the pro-perfume is a dimethoxybenzoin derivative as described in USPA 2006/0020459 A1. In another aspect the pro-perfume is a 3',5'-dimethoxybenzoin (DMB) derivative that releases an alcohol upon exposure to electromagnetic radiation. In yet another aspect, the pro-perfume releases one or more low ODT PRMs, including tertiary alcohols such as linalool, tetrahydrolinalool, or dihydromyrcenol. Suitable pro-perfumes and methods of making same can be found in U.S. Pat. Nos. 7,018,978 B2; 6,987,084 B2; 6,956,013 B2; 6,861,402 B1; 6,544,945 B1; U.S. Pat. Nos. 6,093,691; 6,277,796 B1; 6,165,953; 6,316,397 B1; 6,437,150 B1; 6,479,682 B1; 6,096,918; 6,218,355 B1; 6,133,228; 6,147,037; 7,109,153 B2; 7,071,151 B2; 6,987,084 B2; 6,610,646 B2 and 5,958,870, as well as can be found in USPA 2005/0003980 A1 and USPA 2006/0223726 A1.

a.) Amine Reaction Product (ARP): For purposes of the present application, ARP is a subclass or species of PP. One may also use "reactive" polymeric amines in which the amine functionality is pre-reacted with one or more PRMs to form an amine reaction product (ARP). Typically the reactive amines are primary and/or secondary amines, and may be part of a polymer or a monomer (non-polymer). Such ARPs may also be mixed with additional PRMs to provide benefits of polymer-assisted delivery and/or amine-assisted delivery. Nonlimiting examples of polymeric amines include polymers based on polyalkylimines, such as polyethyleneimine (PEI), or polyvinylamine (PVAm). Nonlimiting examples of monomeric (non-polymeric) amines include hydroxyl amines, such as 2-aminoethanol and its alkyl substituted derivatives, and aromatic amines such as anthranilates. The ARPs may be premixed with perfume or added separately in leave-on or rinse-off applications. In another aspect, a material that contains a heteroatom other than nitrogen, for example oxygen, sulfur, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. The benefit may include improved delivery of perfume as well as controlled perfume release. Suitable ARPs as well as methods of making same can be found in USPA 2005/0003980 A1 and U.S. Pat. No. 6,413,920 B1.

Antimicrobials, Antibacterials & Antifungals

In an example, pyridinethione particulates are suitable antimicrobial active agents for use in the present disclosure. In an example, the antimicrobial active agent is a 1-hydroxy-2-pyridinethione salt and is in particulate form. In an example, the concentration of pyridinethione particulate ranges from about 0.01 wt % to about 5 wt %, or from about 0.1 wt % to about 3 wt %, or from about 0.1 wt % to about 2 wt %, by weight of the dry fibrous element and/or dry particle and/or dry fibrous structure of the present disclosure. In an example, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"), commonly 1-hydroxy-2-pyridinethione salts in platelet particle form. In an example, the 1-hydroxy-2-pyridinethione salts in platelet particle form have an average particle size of up to about 20 microns, or up to about 5 microns, or up to about 2.5 microns as measured according to the Median Particle Size Test Method described herein. Salts formed from other cations, such as sodium, may also be suitable. Pyridinethione actives are described, for example, in U.S. Pat. Nos. 2,809,971; 3,236,733; 3,753,196; 3,761,418; 4,345,080; 4,323,683; 4,379,753; and 4,470,982.

In another example, the antibacterial is chosen from triclosan, triclocarban, chlorohexidine, metronitazole and mixtures thereof.

In an example, in addition to the antimicrobial active selected from polyvalent metal salts of pyrithione, the composition can further include one or more anti-fungal and/or anti-microbial actives. In an example, the anti-microbial active is selected from the group consisting of: coal tar, sulfur, azoles, selenium sulphide, particulate sulphur, keratolytic agents, charcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof.

Bleaching Agents

The fibrous elements and/or particles of the present disclosure may comprise one or more bleaching agents. Non-limiting examples of suitable bleaching agents include peroxyacids, perborate, percarbonate, chlorine bleaches, oxygen bleaches, hypohalite bleaches, bleach precursors, bleach activators, bleach catalysts, hydrogen peroxide, bleach boosters, photobleaches, bleaching enzymes, free radical initiators, peroxygen bleaches, and mixtures thereof.

One or more bleaching agents may be included in the fibrous elements and/or particles of the present disclosure may be included at a level from about 0.05% to about 30% and/or from about 1% to about 20% by weight on a dry fibrous element basis and/or dry particle basis and/or dry fibrous structure basis. If present, bleach activators may be present in the fibrous elements and/or particles of the present disclosure at a level from about 0.1% to about 60% and/or from about 0.5% to about 40% by weight on a dry fibrous element basis and/or dry particle basis and/or dry fibrous structure basis.

Non-limiting examples of bleaching agents include oxygen bleach, perborate bleach, percarboxylic acid bleach and salts thereof, peroxygen bleach, persulfate bleach, percarbonate bleach, and mixtures thereof. Further, non-limiting examples of bleaching agents are disclosed in U.S. Pat. No. 4,483,781, U.S. patent application Ser. No. 740,446, European Patent Application 0 133 354, U.S. Pat. Nos. 4,412,934, and 4,634,551.

Non-limiting examples of bleach activators (e.g., acyl lactam activators) are disclosed in U.S. Pat. Nos. 4,915,854; 4,412,934; 4,634,551; and 4,966,723.

In one example, the bleaching agent comprises a transition metal bleach catalyst, which may be encapsulated. The transition metal bleach catalyst typically comprises a transition metal ion, for example a transition metal ion from a transition metal selected from the group consisting of: Mn(II), Mn(III), Mn(IV), Mn(V), Fe(II), Fe(III), Fe(IV), Co(I), Co(II), Co(III), Ni(I), Ni(II), Ni(III), Cu(I), Cu(II), Cu(III), Cr(II), Cr(III), Cr(IV), Cr(V), Cr(VI), V(III), V(IV), V(V), Mo(IV), Mo(V), Mo(VI), W(IV), W(V), W(VI), Pd(II), Ru(II), Ru(III), and Ru(IV). In one example, the transition metal is selected from the group consisting of: Mn(II), Mn(III), Mn(IV), Fe(II), Fe(III), Cr(II), Cr(III), Cr(IV), Cr(V), and Cr(VI). The transition metal bleach catalyst typically comprises a ligand, for example a macropolycyclic ligand, such as a cross-bridged macropolycyclic ligand. The transition metal ion may be coordinated with the ligand. Further, the ligand may comprise at least four donor atoms, at least two of which are bridgehead donor atoms. Non-limiting examples of suitable transition metal bleach catalysts are described in U.S. Pat. Nos. 5,580,485, 4,430,243; 4,728,455; 5,246,621; 5,244,594; 5,284,944; 5,194,416; 5,246,612; U.S. 5,256,779; U.S. Pat. Nos. 5,280,117; 5,274,147; 5,153,161; 5,227,084; 5,114,606; 5,114,611, EP 549,271 A1; EP 544,490 A1; EP 549,272 A1; and EP 544,440 A2. In one example, a suitable transition metal bleach catalyst comprises a manganese-based catalyst, for example disclosed in U.S. Pat. No. 5,576,282. In another example, suitable cobalt bleach catalysts are described, in U.S. Pat. Nos. 5,597,936 and 5,595,967. Such cobalt catalysts are readily prepared by known procedures, such as taught for example in U.S. Pat. Nos. 5,597,936, and 5,595,967. In yet another, suitable transition metal bleach catalysts comprise a transition metal complex of ligand such as bispidones described in WO 05/042532 A1.

Non-limiting examples of bleach catalysts include a catalyst system comprising a transition metal cation of defined bleach catalytic activity, such as copper, iron, titanium, ruthenium tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243. Other types of bleach catalysts include the manganese-based complexes disclosed in U.S. Pat. Nos. 5,246,621 and 5,244,594. Preferred examples of theses catalysts include $Mn^{IV}_2(u-O)_3(1,4,7\text{-trimethyl-}1,4,7\text{-triazacyclononane})_2\text{-}(PF_6)_2$ ("MnTACN"), $Mn^{III}_2(u-O)_1(u-OAc)_2(1,4,7\text{-trimethyl-}1,4,7\text{-triazacyclononane})_2\text{-}(ClO_4)_2$, $Mn^{IV}_4(u-O)_6(1,4,7\text{-triazacyclononane})_4\text{-}(ClO_4)_2$, $Mn^{III} Mn^{IV}_4(u-O)_1(u-OAc)_2(1,4,7\text{-trimethyl-}1,4,7\text{-triazacyclononane})_2\text{-}(ClO_4)_3$, and mixtures thereof. See also European patent application publication no. 549,272. Other ligands suitable for use herein include 1,5,9-trimethyl-1,5,9-triazacyclododecane, 2-methyl-1,4,7-triazacyclononane, 2-methyl-1,4,7-triazacyclononane, and mixtures thereof. The bleach catalysts useful in automatic dishwashing compositions and concentrated powder detergent compositions may also be selected as appropriate for the present disclosure. For examples of suitable bleach catalysts see U.S. Pat. Nos. 4,246,612 and 5,227,084. See also U.S. Pat. No. 5,194,416 which teaches mononuclear manganese (IV) complexes such as $Mn(1,4,7\text{-trimethyl-}1,4,7\text{-triazacyclononane})$ $(OCH3)_3\text{-}(PF_6)$. Still another type of bleach catalyst, as disclosed in U.S. Pat. No. 5,114,606, is a water-soluble complex of manganese (II), (III), and/or (UV) with a ligand which is a non-carboxylate polyhydroxy compound having at least three consecutive C—OH groups. Preferred ligands include sorbitol, iditol, dulsitol, mannitol, xylitol, arabitol, adonitol, meso-erythritol, meso-inositol, lactose, and mixtures thereof. U.S. Pat. No. 5,114,611 teaches a bleach catalyst comprising a complex of transition metals, including Mn, Co, Fe, or Cu, with an non-(macro)-cyclic ligand. Non-limiting examples of ligands include pyridine, pyridazine, pyrimidine, pyrazine, imidazole, pyrazole, and triazole rings. In one example, the ligand is 2,2'-bispyridylamine. In one example, the bleach catalysts includes a Co, Cu, Mn, Fe,-bispyridylmethane and-bispyridylamine complex, such as $Co(2,2'\text{-bispyridylamine})Cl_2$, Di(isothiocyanato) bispyridylamine-cobalt (II), trisdipyridylamine-cobalt (II) perchlorate, $Co(2,2\text{-bispyridylamine})_2O_2ClO_4$, Bis-(2,2'-bispyridylamine) copper(II) perchlorate, tris(di-2-pyridylamine) iron (II) perchlorate, and mixtures thereof. Other examples of bleach catalysts include Mn gluconate, $Mn(CF_3SO_3)_2$, $Co(NH_3)_5Cl$, and the binuclear Mn complexed with tetra-N-dentate and bi-N-dentate ligands, including $N_4Mn(III)(u-O)_2 Mn(IV) N_4)^+$ and $[Bipy_2Mn(III)(u-O)_2Mn(IV) bipy_2]\text{-}(ClO_4)_3$.

The bleach catalysts may also be prepared by combining a water-soluble ligand with a water-soluble manganese salt in aqueous media and concentrating the resulting mixture by evaporation. Any convenient water-soluble salt of manganese can be used herein. Manganese (II), (III), (IV) and/or (V) is readily available on a commercial scale. In some instances, sufficient manganese may be present in the wash liquor, but, in general, it is preferred to detergent composition Mn cations in the compositions to ensure its presence in catalytically-effective amounts. Thus, the sodium salt of the ligand and a member selected from the group consisting of $MnSO_4$, $Mn(ClO_4)_2$ or $MnCl_2$ (least preferred) are dissolved in water at molar ratios of ligand: Mn salt in the range of about 1:4 to 4:1 at neutral or slightly alkaline pH. The water may first be de-oxygenated by boiling and cooled by spraying with nitrogen. The resulting solution is evaporated (under $N_2$, if desired) and the resulting solids are used in the bleaching and detergent compositions herein without further purification.

In an alternate mode, the water-soluble manganese source, such as $MnSO_4$, is added to the bleach/cleaning composition or to the aqueous bleaching/cleaning bath which comprises the ligand. Some type of complex is apparently formed in situ, and improved bleach performance is secured. In such an in situ process, it is convenient to use a considerable molar excess of the ligand over the manganese, and mole ratios of ligand:Mn typically are 3:1 to 15:1. The additional ligand also serves to scavenge vagrant metal ions such as iron and copper, thereby protecting the bleach from decomposition. One possible such system is described in European patent application, publication no. 549, 271.

While the structures of the bleach-catalyzing manganese complexes useful in the present disclosure have not been elucidated, it may be speculated that they comprise chelates or other hydrated coordination complexes which result from the interaction of the carboxyl and nitrogen atoms of the ligand with the manganese cation. Likewise, the oxidation state of the manganese cation during the catalytic process is not known with certainty, and may be the (+II), (+III), (+IV) or (+V) valence state. Due to the ligands' possible six points of attachment to the manganese cation, it may be reasonably speculated that multi-nuclear species and/or "cage" structures may exist in the aqueous bleaching media. Whatever the form of the active Mnâ€øligand species which actually exists, it functions in an apparently catalytic manner to provide improved bleaching performances on stubborn stains such as tea, ketchup, coffee, wine, juice, and the like.

Other bleach catalysts are described, for example, in European patent application, publication no. 408,131 (cobalt complex catalysts), European patent applications, publication nos. 384,503, and 306,089 (metallo-porphyrin catalysts), U.S. Pat. No. 4,728,455 (manganese/multidentate ligand catalyst), U.S. Pat. No. 4,711,748 and European patent application, publication no. 224,952, (absorbed manganese on aluminosilicate catalyst), U.S. Pat. No. 4,601,845 (aluminosilicate support with manganese and zinc or magnesium salt), U.S. Pat. No. 4,626,373 (manganese/ligand catalyst), U.S. Pat. No. 4,119,557 (ferric complex catalyst), German Pat. specification 2,054,019 (cobalt chelant catalyst) Canadian 866,191 (transition metal-containing salts), U.S. Pat. No. 4,430,243 (chelants with manganese cations and non-catalytic metal cations), and U.S. Pat. No. 4,728, 455 (manganese gluconate catalysts).

In one example, the bleach catalyst comprises a cobalt pentaamine chloride salts having the formula $[Co(NH_3)_5 Cl] Y_y$, and especially $[Co(NH_3)_5 Cl]Cl_2$. Other cobalt bleach catalysts useful herein are described for example along with their base hydrolysis rates, in M. L. Tobe, "Base Hydrolysis of Transition-Metal Complexes", Adv. Inorg. Bioinorg. Mech., (1983), 2, pages 1-94. For example, Table 1 at page 17, provides the base hydrolysis rates (designated therein as $k_{OH}$) for cobalt pentaamine catalysts complexed with oxalate ($k_{OH}=2.5\text{\AA}-10^{-4}$ $M^{-1}$ $s^{-1}$ (25° C.)), $NCS^-$-($k_{OH}=5. 0\text{\AA}-10^{-4}$ $M^{-1}$ $s^{-1}$ (25° C.)), formate ($k_{OH}=5. 8. \text{times}.10^{-4}$ $M^{-1}$ $s^{-1}$ (25° C.)), and acetate ($k_{OH}=9.6\text{\AA}-10^{-4}$ $M^{-1}$ $s^{-1}$ (25° C.)). The most preferred cobalt catalyst useful herein are cobalt pentaamine acetate salts having the formula $[Co(NH_3)_5 OAc]T_y$, wherein OAc represents an acetate moiety, and especially cobalt pentaamine acetate chloride, $[Co(NH_3)_5 OAc]Cl_2$; as well as $[Co(NH_3)_5 OAc](OAc)_2$; $[Co(NH_3)_5 OAc](PF_6)_2$; $[Co(NH_3)_5 OAc](SO_4)$; $[Co(NH_3)_5 OAc](BF_4)_2$; and $[Co(NH_3)_5 OAc](NO_3)_2$.

These bleach catalysts may be readily prepared by known procedures, such as taught for example in the Tobe article hereinbefore and the references cited therein, in U.S. Pat. No. 4,810,410, to Diakun et al, issued Mar. 7, 1989, J. Chem. Ed. (1989), 66 (12), 1043-45; The Synthesis and Characterization of Inorganic Compounds, W. L. Jolly (Prentice-Hall; 1970), pp. 461-3; Inorg. Chem., 18, 1497-1502 (1979); Inorg. Chem., 21, 2881-2885 (1982); Inorg. Chem., 18, 2023-2025 (1979); Inorg. Synthesis, 173-176 (1960); and Journal of Physical Chemistry 56, 22-25 (1952). These bleach catalysts may also be coprocessed with adjunct materials so as to reduce the color impact if desired for the aesthetics of the product, or to be included in enzyme-containing particles as exemplified hereinafter, or the compositions may be manufactured to contain catalyst "speckles".

Bleaching agents other than oxygen bleaching agents are also known in the art and can be utilized herein (e.g., photoactivated bleaching agents such as the sulfonated zinc and/or aluminum phthalocyanines (U.S. Pat. No. 4,033,718, incorporated herein by reference)), and/or pre-formed organic peracids, such as peroxycarboxylic acid or salt thereof, and/or peroxysulphonic acids or salts thereof. In one example, a suitable organic peracid comprises phthaloylimidoperoxycaproic acid or salt thereof. When present, the photoactivated bleaching agents, such as sulfonated zinc phthalocyanine, may be present in the fibrous elements and/or particles and/or fibrous structures of the present disclosure at a level from about 0.025% to about 1.25% by weight on a dry fibrous element basis and/or dry particle basis and/or dry fibrous structure basis.

Non-limiting examples of bleach activators are selected from the group consisting of tetraacetyl ethylene diamine (TAED), benzoylcaprolactam (BzCL), 4-nitrobenzoylcaprolactam, 3-chlorobenzoyl-caprolactam, benzoyloxybenzene-sulphonate (BOBS), nonanoyloxybenzene-sulphonate (NOBS), phenyl benzoate (PhBz), decanoyloxybenzenesulphonate ($C_{10}$-OBS), benzoylvalerolactam (BZVL), octanoyloxybenzenesulphonate ($C_8$-OBS), perhydrolyzable esters and mixtures thereof, most preferably benzoylcaprolactam and benzoylvalerolactam. Particularly preferred bleach activators in the pH range from about 8 to about 9.5 are those selected having an OBS or VL leaving group. Quaternary substituted bleach activators (a quaternary substituted bleach activator (QSBA) or a quaternary substituted peracid (QSP)) may also be included.

Non-limiting examples of organic peroxides, such as diacyl peroxides are extensively illustrated in Kirk Othmer, Encyclopedia of Chemical Technology, Vol. 17, John Wiley and Sons, 1982 at pages 27-90 and especially at pages 63-72, all incorporated wherein by reference. If a diacyl peroxide is used, it may be one which exerts minimal adverse impact on spotting/filming.

Dye Transfer Inhibiting Agents

The fibrous elements and/or particles of the present disclosure may include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. The dye transfer inhibiting agents may be present in the fibrous elements and/or particles and/or fibrous structure products of the present disclosure at levels from about 0.0001% to about 10%, from about 0.01% to about 5% or even from about 0.1% to about 3% by weight on a dry fibrous element basis and/or dry particle basis and/or dry fibrous structure basis.

Brighteners

The fibrous elements and/or particles of the present disclosure may contain active agents, such as brighteners, for example fluorescent brighteners. Such brighteners may tint articles being cleaned.

The fibrous elements and/or particles may comprise C.I. fluorescent brightener 260 in α-crystalline form having the following structure:

of stilbene, pyrazoline, coumarin, carboxylic acid, methinecyanines, dibenzothiophene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982). Specific nonlimiting examples of optical brighteners which are useful in the present compositions are those identified in U.S. Pat. Nos. 4,790,856 and 3,646,015.

A further suitable brightener has the structure below:

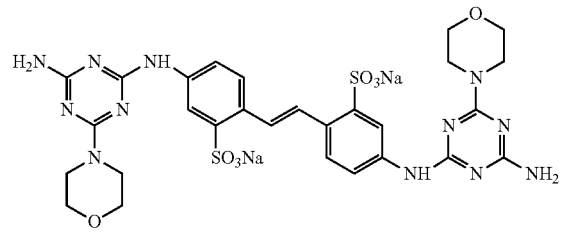

Suitable fluorescent brightener levels include lower levels of from about 0.01, from about 0.05, from about 0.1 or even from about 0.2 wt % to upper levels of 0.5 or even 0.75 wt %.

In one aspect the brightener may be loaded onto a clay to form a particle.

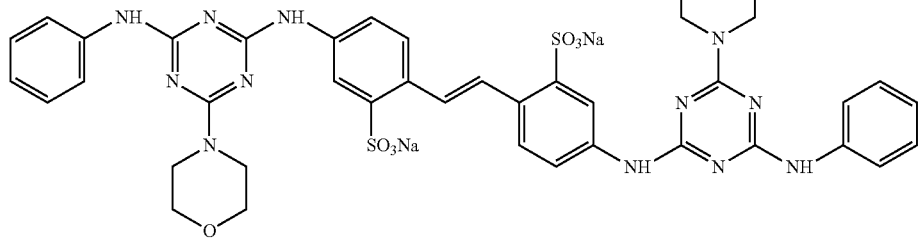

In one aspect, the brightener is a cold water-soluble brightener, such as the C.I. fluorescent brightener 260 in α-crystalline form.

In one aspect the brightener is predominantly in α-crystalline form, which means that typically at least 50 wt %, at least 75 wt %, at least 90 wt %, at least 99 wt %, or even substantially all, of the C.I. fluorescent brightener 260 is in α-crystalline form.

The brightener is typically in a micronized particulate form, having a weight average primary particle size of from 3 to 30 μm, from 3 to 20 μm, or from 3 to 10 μm as measured according to the Median Particle Size Test Method The composition may comprises C.I. fluorescent brightener 260 in β-crystalline form, and the weight ratio of: (i) C.I. fluorescent brightener 260 in α-crystalline form, to (ii) C.I. fluorescent brightener 260 in β-crystalline form may be at least 0.1, or at least 0.6.

BE680847 relates to a process for making C.I fluorescent brightener 260 in α-crystalline form.

Commercial optical brighteners which may be useful in the present disclosure can be classified into subgroups, which include, but are not necessarily limited to, derivatives Hueing Agents The composition may comprise a hueing agent. Suitable hueing agents include dyes, dye-clay conjugates, and pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof.

In another aspect, suitable small molecule dyes include small molecule dyes selected from the group consisting of Colour Index (Society of Dyers and Colourists, Bradford, UK) numbers Direct Violet 9, Direct Violet 35, Direct Violet 48, Direct Violet 51, Direct Violet 66, Direct Violet 99, Direct Blue 1, Direct Blue 71, Direct Blue 80, Direct Blue 279, Acid Red 17, Acid Red 73, Acid Red 88, Acid Red 150, Acid Violet 15, Acid Violet 17, Acid Violet 24, Acid Violet 43, Acid Red 52, Acid Violet 49, Acid Violet 50, Acid Blue 15, Acid Blue 17, Acid Blue 25, Acid Blue 29, Acid Blue 40, Acid Blue 45, Acid Blue 75, Acid Blue 80, Acid Blue 83, Acid Blue 90 and Acid Blue 113, Acid Black 1, Basic Violet 1, Basic Violet 3, Basic Violet 4, Basic Violet 10, Basic Violet 35, Basic Blue 3, Basic Blue 16, Basic Blue 22, Basic Blue 47, Basic Blue 66, Basic Blue 75, Basic Blue 159 and mixtures thereof. In another aspect, suitable small molecule dyes include small molecule dyes selected from the group consisting of Colour Index (Society of Dyers and Colourists, Bradford, UK) numbers Acid Violet 17, Acid Violet 43, Acid Red 52, Acid Red 73, Acid Red 88, Acid Red 150, Acid Blue 25, Acid Blue 29, Acid Blue 45, Acid Blue 113, Acid Black 1, Direct Blue 1, Direct Blue 71, Direct Violet 51 and mixtures thereof. In another aspect, suitable small molecule dyes include small molecule dyes selected from the group consisting of Colour Index (Society of Dyers and Colourists, Bradford, UK) numbers Acid Violet 17, Direct Blue 71, Direct Violet 51, Direct Blue 1, Acid Red 88, Acid Red 150, Acid Blue 29, Acid Blue 113 or mixtures thereof.

Suitable polymeric dyes include polymeric dyes selected from the group consisting of polymers containing conjugated chromogens (dye-polymer conjugates) and polymers with chromogens co-polymerized into the backbone of the polymer and mixtures thereof.

In another aspect, suitable polymeric dyes include polymeric dyes selected from the group consisting of surface-substantive colorants sold under the name of Liquitint® (Milliken, Spartanburg, South Carolina, USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® (Milliken, Spartanburg, South Carolina, USA) Violet CT, carboxymethyl cellulose (CMC) conjugated with a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Preferred hueing dyes include the whitening agents found in WO 08/87497 A1. These whitening agents may be characterized by the following structure (I):

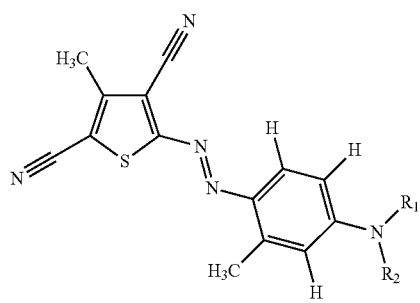

wherein $R_1$ and $R_2$ can independently be selected from:
a) $[(CH_2CR'HO)_x(CH_2CR''HO)_yH]$
wherein R' is selected from the group consisting of H, $CH_3$, $CH_2O(CH_2CH_2O)_zH$, and mixtures thereof; wherein R'' is selected from the group consisting of H, $CH_2O(CH_2CH_2O)_zH$, and mixtures thereof; wherein x+y≤5; wherein y≥1; and wherein z=0 to 5;
b) $R_1$=alkyl, aryl or aryl alkyl and $R_2$=$[(CH_2CR'HO)_x(CH_2CR''HO))_yH]$ wherein R' is selected from the group consisting of H, $CH_3$, $CH_2O(CH_2CH_2O)_zH$, and mixtures thereof; wherein R'' is selected from the group consisting of H, $CH_2O(CH_2CH_2O)_zH$, and mixtures thereof; wherein x+y≤10; wherein y≥1; and wherein z=0 to 5;

c) $R_1$=$[CH_2CH_2(OR_3)CH_2OR_4]$ and $R_2$=$[CH_2CH_2(OR^3)CH_2OR_4]$
wherein $R^3$ is selected from the group consisting of H, $(CH_2CH_2O)_zH$, and mixtures thereof; and wherein z=0 to 10;
wherein $R^4$ is selected from the group consisting of $(C_1-C_{16})$alkyl, aryl groups, and mixtures thereof; and d) wherein R1 and R2 can independently be selected from the amino addition product of styrene oxide, glycidyl methyl ether, isobutyl glycidyl ether, isopropylglycidyl ether, t-butyl glycidyl ether, 2-ethylhexylgycidyl ether, and glycidylhexadecyl ether, followed by the addition of from 1 to 10 alkylene oxide units.

A preferred whitening agent of the present disclosure may be characterized by the following structure (II):

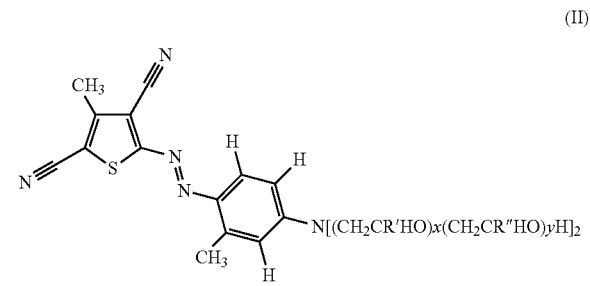

wherein R' is selected from the group consisting of H, $CH_3$, $CH_2O(CH_2CH_2O)_zH$, and mixtures thereof; wherein R'' is selected from the group consisting of H, $CH_2O(CH_2CH_2O)_zH$, and mixtures thereof; wherein x+y≤5; wherein y≥1; and wherein z=0 to 5.

A further preferred whitening agent of the present disclosure may be characterized by the following structure (III):

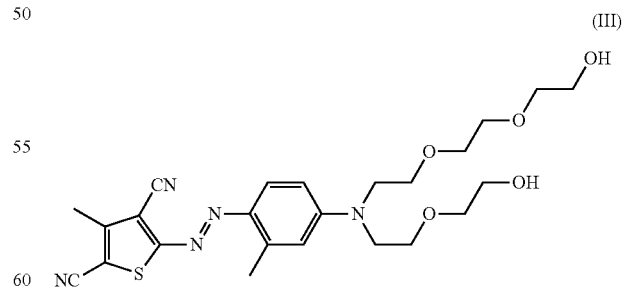

This whitening agent is commonly referred to as "Violet DD". Violet DD is typically a mixture having a total of 5 EO groups. This structure is arrived the following selection in Structure I of the following pendant groups in "part a" above:

|   | R1 | | | | R2 | | | |
|---|---|---|---|---|---|---|---|---|
|   | R' | R" | X | Y | R' | R" | x | y |
| a | H | H | 3 | 1 | H | H | 0 | 1 |
| b | H | H | 2 | 1 | H | H | 1 | 1 |
| c = b | H | H | 1 | 1 | H | H | 2 | 1 |
| d = a | H | H | 0 | 1 | H | H | 3 | 1 |

Further whitening agents of use include those described in USPN 2008 34511 A1 (Unilever). A preferred agent is "Violet 13".

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by C1-C3-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof.

In another aspect, suitable pigments include pigments selected from the group consisting of Ultramarine Blue (C.I. Pigment Blue 29), Ultramarine Violet (C.I. Pigment Violet 15) and mixtures thereof.

The aforementioned fabric hueing agents can be used in combination (any mixture of fabric hueing agents can be used). Suitable fabric hueing agents can be purchased from Aldrich, Milwaukee, Wisconsin, USA; Ciba Specialty Chemicals, Basel, Switzerland; BASF, Ludwigshafen, Germany; Dayglo Color Corporation, Mumbai, India; Organic Dyestuffs Corp., East Providence, Rhode Island, USA; Dystar, Frankfurt, Germany; Lanxess, Leverkusen, Germany; Megazyme, Wicklow, Ireland; Clariant, Muttenz, Switzerland; Avecia, Manchester, UK and/or made in accordance with the examples contained herein. Suitable hueing agents are described in more detail in U.S. Pat. No. 7,208,459 B2.

Enzymes

One or more enzymes may be present in the fibrous elements and/or particles of the present disclosure. Non-limiting examples of suitable enzymes include proteases, amylases, lipases, cellulases, carbohydrases including mannanases and endoglucanases, pectinases, hemicellulases, peroxidases, xylanases, phopholipases, esterases, cutinases, keratanases, reductases, oxidases, phenoloxidases, lipoxygenases, ligninases, pullulanases, tannases, penosanases, malanases, glucanases, arabinosidases, hyaluraonidases, chrondroitinases, laccases, and mixtures thereof.

Enzymes may be included in the fibrous elements and/or particles of the present disclosure for a variety of purposes, including but not limited to removal of protein-based, carbohydrate-based, or triglyceride-based stains from substrates, for the prevention of refugee dye transfer in fabric laundering, and for fabric restoration. In one example, the fibrous elements and/or particles of the present disclosure may include proteases, amylases, lipases, cellulases, peroxidases, and mixtures thereof of any suitable origin, such as vegetable, animal, bacterial, fungal and yeast origin. Selections of the enzymes utilized are influenced by factors such as pH-activity and/or stability optima, thermostability, and stability to other additives, such as active agents, for example builders, present within the fibrous elements and/or particles. In one example, the enzyme is selected from the group consisting of: bacterial enzymes (for example bacterial amylases and/or bacterial proteases), fungal enzymes (for example fungal cellulases), and mixtures thereof.

When present in the fibrous elements and/or particles of the present disclosure, the enzymes may be present at levels sufficient to provide a "cleaning-effective amount". The term "cleaning effective amount" refers to any amount capable of producing a cleaning, stain removal, soil removal, whitening, deodorizing, or freshness improving effect on substrates such as fabrics, dishware, flooring, porcelain and ceramics, metal surfaces and the like. In practical terms for current commercial preparations, typical amounts are up to about 5 mg by weight, more typically 0.01 mg to 3 mg, of active enzyme per gram of the fibrous element and/or particle of the present disclosure. Stated otherwise, the fibrous elements and/or particles of the present disclosure will typically comprise from about 0.001% to about 5% and/or from about 0.01% to about 3% and/or from about 0.01% to about 1% by weight on a dry fibrous element basis and/or dry particle basis and/or dry fibrous structure basis.

One or more enzymes may be applied to the fibrous element and/or particle after the fibrous element and/or particle is produced.

A range of enzyme materials and means for their incorporation into the filament-forming composition of the present disclosure, which may be a synthetic detergent composition, is also disclosed in WO 9307263 A; WO 9307260 A; WO 8908694 A; U.S. Pat. Nos. 3,553,139; 4,101,457; and 4,507,219.

Enzyme Stabilizing System

When enzymes are present in the fibrous elements and/or particles of the present disclosure, an enzyme stabilizing system may also be included in the fibrous elements and/or particles. Enzymes may be stabilized by various techniques.

Non-limiting examples of enzyme stabilization techniques are disclosed and exemplified in U.S. Pat. Nos. 3,600,319 and 3,519,570; EP 199,405, EP 200,586; and WO 9401532 A.

In one example, the enzyme stabilizing system may comprise calcium and/or magnesium ions.

The enzyme stabilizing system may be present in the fibrous elements and/or particles of the present disclosure at a level of from about 0.001% to about 10% and/or from about 0.005% to about 8% and/or from about 0.01% to about 6% by weight on a dry fibrous element basis and/or dry particle basis and/or dry fibrous structure basis. The enzyme stabilizing system can be any stabilizing system which is compatible with the enzymes present in the fibrous elements and/or particles. Such an enzyme stabilizing system may be inherently provided by other formulation actives, or be added separately, e.g., by the formulator or by a manufacturer of enzymes. Such enzyme stabilizing systems may, for example, comprise calcium ion, magnesium ion, boric acid, propylene glycol, short chain carboxylic acids, boronic acids, and mixtures thereof, and are designed to address different stabilization problems.

Heat Forming Agents

The fibrous elements and/or particles of the present disclosure may contain a heat forming agent. Heat forming agents are formulated to generate heat in the presence of water and/or oxygen (e.g., oxygen in the air, etc.) and to thereby accelerate the rate at which the fibrous structure degrades in the presence of water and/or oxygen, and/or to increase the effectiveness of one or more of the actives in the fibrous element. The heat forming agent can also or alternatively be used to accelerate the rate of release of one or more actives from the fibrous structure. The heat forming agent is formulated to undergo an exothermic reaction when exposed to oxygen (i.e., oxygen in the air, oxygen in the water, etc.) and/or water. Many different materials and combination of materials can be used as the heat forming agent. Non-limiting heat forming agents that can be used in the fibrous structure include electrolyte salts (e.g., aluminum chloride, calcium chloride, calcium sulfate, cupric chloride, cuprous chloride, ferric sulfate, magnesium chloride, magnesium sulfate, manganese chloride, manganese sulfate, potassium chloride, potassium sulfate, sodium acetate, sodium chloride, sodium carbonate, sodium sulfate, etc.), glycols (e.g., propylene glycol, dipropylenenglycol, etc.), lime (e.g., quick lime, slaked lime, etc.), metals (e.g., chromium, copper, iron, magnesium, manganese, etc.), metal oxides (e.g., aluminum oxide, iron oxide, etc.), polyalkyleneamine, polyalkyleneimine, polyvinyl amine, zeolites, gycerin, 1,3, propanediol, polysorbates esters (e.g., Tweens 20, 60, 85, 80), and/or poly glycerol esters (e.g., Noobe, Drewpol and Drewmulze from Stepan). The heat forming agent can be formed of one or more materials. For example, magnesium sulfate can singularly form the heat forming agent. In another non-limiting example, the combination of about 2-25 weight percent activated carbon, about 30-70 weight percent iron powder and about 1-10 weight percent metal salt can form the heat forming agent. As can be appreciated, other or additional materials can be used alone or in combination with other materials to form the heat forming agent. Non-limiting examples of materials that can be used to form the heat forming agent used in a fibrous structure are disclosed in U.S. Pat. Nos. 5,674,270 and 6,020,040; and in U.S. Patent Application Publication Nos. 2008/0132438 and 2011/0301070.

Degrading Accelerators

The fibrous elements and/or particles of the present disclosure may comprise or contain a degrading accelerators used to accelerate the rate at which a fibrous structure degrades in the presence of water and/or oxygen. The degrading accelerator, when used, is generally designed to release gas when exposed to water and/or oxygen, which in turn agitates the region about the fibrous structure so as to cause acceleration in the degradation or dissolution of the fibrous structure. The degrading accelerator, when used, can also or alternatively be used to accelerate the rate of release of one or more actives from the fibrous structure; however, this is not required. The degrading accelerator, when used, can also or alternatively be used to increase the effectivity of one or more of the actives in the fibrous structure; however, this is not required. The degrading accelerator can include one or more materials such as, but not limited to, alkali metal carbonates (e.g., sodium carbonate, potassium carbonate, etc.), alkali metal hydrogen carbonates (e.g., sodium hydrogen carbonate, potassium hydrogen carbonate, sodium bicarbonate, etc.), ammonium carbonate, etc. The fibrous structure may optionally include one or more activators that are used to activate or increase the rate of activation of the one or more degrading accelerators in the fibrous structure. As can be appreciated, one or more activators can be included in the fibrous structure even when no degrading accelerator exists in the fibrous structure; however, this is not required. For instance, the activator system may also comprise an acidic or basic compound, wherein such acidic or basic compound can be used as a supplement to one or more actives in the fibrous structure when a degrading accelerator is or is not included in the fibrous structure. Non-limiting examples of activators, when used, that can be included in the fibrous structure include organic acids (e.g., hydroxycarboxylic acids [citric acid, tartaric acid, malic acid, lactic acid, gluconic acid, etc.], saturated aliphatic carboxylic acids [acetic acid, succinic acid, etc.], unsaturated aliphatic carboxylic acids [e.g., fumaric acid, etc.]. Non-limiting examples of materials that can be used to form degrading accelerators and activators used in a fibrous structure are disclosed in U.S. Patent Application Publication No. 2011/0301070.

Effervescent Agents

The effervescent agents of the present disclosure comprise a composition that is capable of effervescence. The term "effervescent," as defined herein, means any product capable of forming bubbles in liquid environments and may also be considered any product capable of liberating carbon dioxide in or out of liquid environments. Likewise, "effervescence" means forming bubbles in liquid environments or liberating carbon dioxide in or out of liquid environments. Alternatively, "effervescence" means fizzing or foaming of an article upon encountering a liquid or aqueous environment. In certain examples, the presence of bubbles results from the formation of carbon dioxide. For instance, when added to a liquid, such as water, a mixture of at least one acid and at least one salt results in a chemical reaction that liberates carbon dioxide. In one aspect, both the acid and the salt may be in anhydrous form.

Examples of acids suitable for use in these illustrative examples include, but are not limited to, tartaric acid, citric acid, fumaric acid, adipic acid, malic acid, oxalic acid, or sulfamic acid, either alone or in combination. Typically, the effervescent of these examples is prepared from citric acid or a combination of citric acid and tartaric acid. Examples of salts suitable for use in illustrative examples include, but are not limited to, the alkali metal salts. Sodium carbonate, calcium carbonate, magnesium carbonate, ammonium carbonate, potassium carbonate, sodium bicarbonate, calcium bicarbonate, and combinations thereof may all be employed.

In other examples, the selection of specific acids and/or salts and their proportions depends, at least in part, upon the requirements for the amount of carbon dioxide release. In some examples, the acid may be added in an amount of about 10% to about 60% by weight of the effervescent components, while the alkali metal salt may also be added in an amount of about 10% to 60% by weight of the effervescent components.

In one example, the effervescent components may comprise from about 0.1% to about 50% and/or from about 1% to about 40% and/or from about 5% to about 30% by weight on a dry fibrous element basis and/or a dry particle basis and/or dry fibrous structure and/or dry article basis.

Cooling Agents

The purpose of the cooling agent is to provide the user with a perceptible sensation when a fluid insult is occurring and/or has occurred to the fibrous structure or the article. This sensation is the result of an actual temperature drop or a stimulating material that provides the perception of a temperature drop.

The cooling agent is desirably in the form of a solid which may include particles, flakes, fibers, agglomerates, granules, powders, spheres, pulverized materials, or the like, as well as combinations thereof. The solids may have any desired shape such as, for example, cubic, rod-like, polyhedral, spherical or semi-spherical, rounded or semi-rounded, angular, irregular, and the like. In one example, the cooling agent is provided in particulate form for ease of processing in the described aspects.

The amount of cooling agent can be expressed in terms of basis weight. Accordingly, the basis weight of the cooling active alone may range from about 5 gsm to about 100 gsm and/or from about 100 gsm to about 800 gsm and/or from about 200 gsm to about 600 gsm.

In one example, the solubility of such cooling agents when contacted with an aqueous liquid, for example water, may be from about 0.01 to about 6 grams of material per gram of water (g/g) and/or from about 0.1 g/g to about 3 g/g.

The cooling agent is responsive to contact with an aqueous, dissolving solution to provide a cooling effect. In one aspect, a mechanism by which this is accomplished is by dissolution of the cooling agent in the aqueous, dissolving solution. For example, the cooling agent may include particles that have a substantial energy difference between a dissolved state and a crystalline state so that energy in the form of heat is absorbed. In the alternative, cooling agent may include particles that provide the sensation of a substantial energy difference.

In one example, the fibrous structure and/or article may suitably provide a temperature change when insulted with an aqueous, dissolving liquid of at least about 2° C. and/or at least about 5° C. and/or at least about 10° C. and/or from about 3° C. to about 15° C.

Polyols such as xylitol particles may be selected as a cooling agent. A cooling sensation occurs because xylitol particles absorb heat when dissolved in an aqueous liquid. Alternatively, other polyols such as sorbitol or erythritol may be advantageously selected to provide a cooling sensation. In yet other examples, various combinations of the above cooling agents may be utilized. Suitable polyols can be obtained from Roquette America, Inc., a company having offices in Keokuk, Iowa, U.S.A., under the trade name of XYLISORB (xylitol) or NEOSORB (sorbitol). Such polyols can generally be obtained from the manufacturer in particular particle sizes, such as 90 microns, 300 microns, 500 microns, and the like for disposition in the fibrous web or article.

Other suitable cooling agents that absorb heat during dissolution include salt hydrates, such as sodium acetate ($H_2O$), sodium carbonate ($H_2O$), sodium sulfate ($H_2O$), sodium thiosulfate ($H_2O$), and sodium phosphate ($H_2O$); anhydrous salts such as ammonium nitrate, potassium nitrate, ammonium chloride, potassium chloride, and sodium nitrate; organic compounds such as urea and the like or combinations thereof.

In addition, as referenced above, in some aspects, the fibrous web or article desirably provides a surface temperature change when wet of from about 2° C. to about 15° C. To achieve this result, the temperature change substance and the amount used should be selected so that the possible total energy change is from about 1 to about 30 calories per square centimeter ($cal/cm^2$), which may represent either a possible total energy release of from about 1 to about 20 $cal/cm^2$ and/or a possible total energy absorption of from about 2 to about 15 $cal/cm^2$, or such as from about 3 to about 10 $cal/cm^2$.

Temperature change agents that absorb heat on contact with an aqueous solution desirably have a heat of solution, hydration, or reaction greater than about 5 cal/g and/or less than about −120 cal/g. The heat of solution, hydration, or reaction is suitably within the range of from about 30 to about 90 cal/g or from about −30 to about −90 cal/g, such as from about 30 to about 70 cal/g or from about −30 to about −70 cal/g, such as xylitol at −32 cal/g or urea at −60 cal/g.

In one example, the cooling agents may comprise from about 0.1% to about 50% and/or from about 1% to about 40% and/or from about 5% to about 30% by weight on a dry fibrous element basis and/or a dry particle basis and/or dry fibrous structure and/or dry article basis Other Active Agents Non-limiting examples of other active agents of the present invention, which in one example may be present as or in a coating composition present on an external surface of one or more fibrous elements and/or on one or more surfaces, for example an inner surface of a fibrous structure ply in a multi-ply fibrous structure and/or multi-ply article of the present invention and/or outer surface of a fibrous structure ply in a multi-ply fibrous structure and/or multi-ply article of the present invention.

In one example, the article comprises a coating composition present on an outer surface of the article. In another example, the article comprises a multi-ply fibrous structure comprising two or more fibrous structure plies wherein a coating composition is present on an inner surface of at least one of the two or more fibrous structure plies. In another example, the article comprises a multi-ply fibrous structure comprising two or more fibrous structure plies wherein a coating composition is present on an outer surface of at least one of the two or more fibrous structure plies.

Non-limiting examples of such other active agents, which may be water-insoluble active agents and/or non-volatile liquid active agents, include silicones, for example silicone oils, cationic silicones, silicone gums, high refractive silicones, functionalized silicones, silicone resins, and mixtures thereof, organic oils, for example hydrocarbon oils, polyolefins, fatty esters, metathesized unsaturated polyol esters, silane-modified oils, and mixtures thereof.

Silicone Active Agents

Non-limiting examples of suitable silicone active agents according to the present disclosure include volatile silicones, non-volatile silicones, and mixtures thereof. In one example, the silicone active agent is a non-volatile silicone active agent. If volatile silicone active agents are present, it will typically be incidental to their use as a solvent or carrier for commercially available forms of non-volatile silicone active agents, such as silicone gums and/or silicone resins. The silicone active agents may be in the form of particles, which may comprise a silicone fluid active agent and may also comprise other ingredients, such as a silicone resins to improve silicone fluid deposition efficiency and/or enhance glossiness of surfaces treated therewith, such as hair.

In one example, the silicone active agents are selected from the group consisting of siloxanes, silicone gums, aminosilicones, terminal aminosilicones, alkyl siloxane polymers, cationic organopolysiloxanes, and mixtures thereof.

In one example, the concentration of the silicone active agents on and/or in the fibrous elements and/or fibrous structures and/or articles of the present disclosure are from about 0.5% to about 30% and/or from about 1% to about 24% and/or from about 2% to about 16% and/or from about 3% to about 8%. Further non-limiting examples of suitable silicone active agents, and optional suspending agents for the silicone active agents, are described in U.S. Reissue Pat. No. 34,584, U.S. Pat. Nos. 5,104,646, and 5,106,609. The silicone active agents for use in the compositions of the present disclosure may exhibit a viscosity, as measured at 25° C., of from about 20 to about 2,000,000 centipoise ("cPs") and/or from about 1,000 to about 1,800,000 cPs and/or from about 50,000 to about 1,500,000 cPs and/or from about 100,000 to about 1,500,000 cPs.

Background material on silicones including sections discussing silicone fluids, silicone gums, and silicone resins, as well as the manufacture of silicones, is found in *Encyclopedia of Polymer Science and Engineering, vol.* 15, 2d ed., pp. 204-308, John Wiley & Sons, Inc. (1989).

The silicone active agents of the present disclosure may comprise one or more silicones including high molecular weight polyalkyl or polyaryl siloxanes and silicone gums; lower molecular weight polydimethyl siloxane fluids; and aminosilicones.

The high molecular weight polyalkyl or polyaryl siloxanes and silicone gums may exhibit a viscosity of from about 100,000 mPa·s to about 30,000,000 mPa·s at 25° C. and/or from about 200,000 mPa·s to about 30,000,000 mPa·s, and/or a weight average molecular weight of from about 100,000 to about 1,000,000 and/or from about 120,000 to about 1,000,000.

In one example, higher molecular weight silicone compounds useful herein include polyalkyl or polyaryl siloxanes with the following structure:

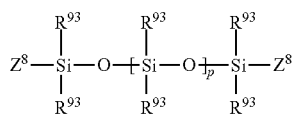

wherein $R^{93}$ is independently an alkyl group or aryl group, and p is an integer from about 1,300 to about 15,000, more preferably from about 1,600 to about 15,000. $Z^8$ is independently an alkyl group or aryl group and represents a group which blocks the ends of the silicone chains. In one example, the alkyl and/or aryl groups substituted on the siloxane chain ($R^{93}$) or at the ends of the siloxane chains $Z^8$ can have any structure as long as the resulting silicone remains fluid at 23° C., is dispersible, is neither irritating, toxic nor otherwise harmful, is compatible with the other components of the composition, is chemically stable under normal use and storage conditions, and is capable of being deposited onto surfaces being treated therewith. In one example, suitable $Z^8$ groups include hydroxy, methyl, methoxy, ethoxy, propoxy, and aryloxy. In one example, the two $R^{93}$ groups on the silicon atom may represent the same group or different groups. In one example, the two $R^{93}$ groups represent the same group. Non-limiting examples of suitable $R^{93}$ groups include methyl, ethyl, propyl, phenyl, methylphenyl and phenylmethyl. In one example the such silicone compounds are referred to as polydimethylsiloxanes, polydiethylsiloxanes, and/or polymethylphenylsiloxanes. In one example, the silicone compound is a polydimethylsiloxane, which is also known as a dimethicone. Commercially available silicone compounds useful herein include, for example, those available from the General Electric Company in their TSF451 series, and those available from Dow Corning in their Dow Corning SH200 series.

The silicone compounds that can be used herein can also include a silicone gum. The term "silicone gum", as used herein, means a polyorganosiloxane material having a viscosity at 25° C. of greater than or equal to 1,000,000 mPa·s. It is recognized that the silicone gums described herein can also have some overlap with the above-disclosed higher molecular weight silicone compounds. This overlap is not intended as a limitation on any of these materials. The "silicone gums" will typically have a mass molecular weight in excess of about 165,000, generally between about 165,000 and about 1,000,000. Non-limiting examples of such silicone gums include polydimethylsiloxanes, poly(dimethylsiloxane methylvinylsiloxane) copolymers, poly(dimethylsiloxane diphenylsiloxane methylvinylsiloxane) copolymers, and mixtures thereof. Commercially available silicone gums useful herein include, for example, TSE200A and CF330M available from the General Electric Company.

In one example, lower molecular weight silicones have a viscosity of from about 1 mPa·s to about 10,000 mPa·s at 25° C. and/or from about 5 mPa·s to about 5,000 mPa·s, and/or a weight average molecular weight of from about 400 to about 65,000 and/or from about 800 to about 50,000.

In one example, lower molecular weight silicone compounds useful herein include polyalkyl or polyaryl siloxanes with the following structure:

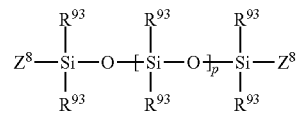

wherein $R^{93}$ is independently an alkyl group or aryl group, and p is an integer from about 7 to about 850, more preferably from about 7 to about 665. $Z^8$ is independently an alkyl group or aryl group and represents a group which blocks the ends of the silicone chains. The alkyl or aryl groups substituted on the siloxane chain ($R^{93}$) or at the ends of the siloxane chains $Z^8$ can have In one example, the alkyl and/or aryl groups substituted on the siloxane chain ($R^{93}$) or at the ends of the siloxane chains $Z^8$ can have any structure as long as the resulting silicone remains fluid at 23° C., is dispersible, is neither irritating, toxic nor otherwise harmful, is compatible with the other components of the composition, is chemically stable under normal use and storage conditions, and is capable of being deposited onto surfaces being treated therewith. In one example, suitable $Z^8$ groups include hydroxy, methyl, methoxy, ethoxy, propoxy, and aryloxy. In one example, the two $R^{93}$ groups on the silicon atom may represent the same group or different groups. In one example, the two $R^{93}$ groups represent the same group. Non-limiting examples of suitable $R^{93}$ groups include methyl, ethyl, propyl, phenyl, methylphenyl and phenylmethyl. In one example such silicone compounds are referred to as polydimethylsiloxanes, polydiethylsiloxanes, and/or polymethylphenylsiloxanes. In one example, the silicone compound is a polydimethylsiloxane, which is also known as a dimethicone. Commercially available silicone compounds useful herein include, for example, those available from the General Electric Company in their TSF451 series, and those available from Dow Corning in their Dow Corning SH200 series.

In one example, the silicone active agent of the present disclosure includes one or more aminosilicones Aminosilicones, as provided herein, are silicones containing at least one primary amine, secondary amine, tertiary amine, or a quaternary ammonium group. In one example, the aminosilicones of the present disclosure may have less than about 0.5% and/or less than about 0.2% and/or less than about 0.1% nitrogen by weight of the aminosilicone. In one example, the aminosilicones of the present disclosure have at least one silicone block with greater than 200 siloxane units.

In one example, the aminosilicone of the present disclosure exhibits a viscosity at 25° C. of from about 1,000 centipoise ("cPs") to about 100,000 cPs and/or from about 2,000 cPs to about 50,000 cPs and/or from about 4,000 cPs to about 40,000 cPs and/or from about 6,000 cPs to about 30,000 cPs.

In one example, the aminosilicones of the present disclosure are water-insoluble. "Water-insoluble aminosilicone" means that the aminosilicone has a solubility of 10 g or less per 100 g water and/or 5 g or less per 100 g water and/or 1 g or less per 100 g water at 25° C. In one example, "water-insoluble aminosilicone" means that the aminosilicone is substantially free of copolyol groups. If copolyol groups are present, they are present at a level of less than 10 wt % and/or less than 5% and/or less than 1 wt % and/or less than 0.1 wt % by weight of the aminosilicone.

In one example, the aminosilicone of the present disclosure, when present, may be present at a level by weight of from about 0.5% to about 30% and/or from about 1.0% to about 24% and/or from about 2.0% to about 16% and/or from about 3.0% to about 8%.

Non-limiting examples of suitable aminosilicones of the present disclosure include those aminiosilicones that conform to the general formula (I):

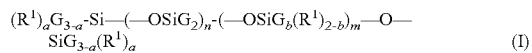

$(R^1)_a G_{3-a}\text{-Si}\text{---}(\text{---OSiG}_2)_n\text{-}(\text{---OSiG}_b(R^1)_{2-b})_m\text{---O---SiG}_{3-a}(R^1)_a$  (I)

wherein G is hydrogen, phenyl, hydroxy, or $C_1$-$C_8$ alkyl, such as methyl; a is 0 or an integer having a value from 1 to 3, such as 1; b is 0, 1, or 2, such as 1; wherein when a is 0, b is not 2; n is a number from 0 to 1,999; m is an integer from 0 to 1,999; the sum of n and m is a number from 1 to 2,000; a and m are not both 0; $R^1$ is a monovalent radical conforming to the general formula $C_qH_{2q}L$, wherein q is an integer having a value from 2 to 8 and L is selected from the following groups: —N($R_2$)CH$_2$—CH$_2$—N($R_2$)$_2$; —N($R_2$)$_2$; —N($R^2$)$^+_3$A$^-$; —N($R^2$)CH$_2$—CH$_2$—N $R^2H_2$A; wherein $R^2$ is hydrogen, phenyl, benzyl, or a saturated hydrocarbon radical, such as an alkyl radical from about $C_1$ to about $C_{20}$; A is a halide ion.

In one example, the aminosilicones correspond to formula (I) wherein m=0, a=1, q=3, G=methyl, n is from about 1500 to about 1700, such as about 1600; and L is —N(CH$_3$)$_2$ or —NH$_2$, such as —NH$_2$. Other aminosilicones can include those corresponding to formula (I) wherein m=0, a=1, q=3, G=methyl, n is from about 400 to about 600, such as about 500; and L is —N(CH$_3$)$_2$ or —NH$_2$, such as —NH$_2$. These aminosilicones can also be referred to as terminal aminosilicones, as one or both ends of the silicone chain are terminated by a nitrogen containing group.

An exemplary aminosilicone corresponding to formula (I) is the polymer known as "trimethylsilylamodimethicone", which is shown below in formula (II):

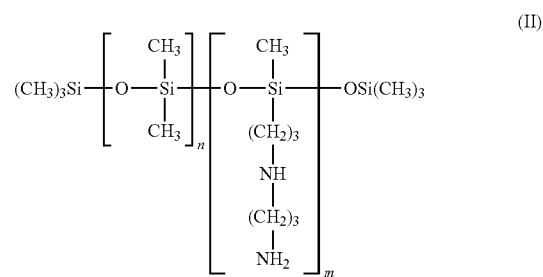

(II)

wherein n is a number from 1 to 1,999 and m is a number from 1 to 1,999.

The silicone may also be a terminal aminosilicone. "Terminal aminosilicone" as defined herein means a silicone polymer comprising one or more amino groups at one or both ends of the silicone backbone. In one example, the active agents of the present disclosure, for example a coating composition comprising active agents of the present disclosure, which may be a hydrophobic coating composition, may be free or substantially free of any silicone compound other than terminal aminosilicones.

In one example, the amino group of at least one terminus of the silicone backbone of the terminal aminosilicone is selected from the group consisting of: primary amines, secondary amines and tertiary amines. The terminal aminosilicone may conform to Formula III:

$(R_1)_a G_{3-a}\text{-Si}\text{---}(\text{---OSiG}_2)_n\text{-O---SiG}_{3-a}(R_1)_a$  III wherein G is hydrogen, phenyl, hydroxy, or $C_1$-$C_8$ alkyl, such as methyl; a is an integer having a value from 1 to 3, or is 1; b is 0, 1 or 2, or is 1; n is a number from 0 to 1,999; $R_1$ is a monovalent radical conforming to the general formula $C_qH_{2q}L$, wherein q is an integer having a value from 2 to 8 and L is selected from the following groups: —N($R_2$)CH$_2$—CH$_2$—N($R_2$)$_2$; —N($R_2$)$_2$; —N($R_2$)$_3$A; —N($R_2$)CH$_2$—CH$_2$—NR$_2$H$_2$A$^-$; wherein $R^2$ is hydrogen, phenyl, benzyl, or a saturated hydrocarbon radical; A is a halide ion. In an aspect, $R^2$ is an alkyl radical having from 1 to 20 carbon atoms, or from 2 to 18 carbon atoms, or from 4 to 12 carbon atoms.

In one example a suitable terminal aminosilicone corresponds to Formula III wherein a=1, q=3, G=methyl, n is from about 1000 to about 2500 and/or from about 1500 to about 1700; and L is —N(CH$_3$)$_2$. In another example, a suitable terminal aminosilicone corresponds to Formula III wherein a=0, G=methyl, n is from about 100 to about 1500 and/or from about 200 to about 1000, L is selected from the following groups: —N($R_2$)CH$_2$—CH$_2$—N($R_2$)$_2$; —N($R_2$)$_2$; —N($R_2$)$_3$A$^-$; —N($R_2$)CH$_2$—CH$_2$—NR$_2$H$_2$A$^-$, such as —NH$_2$; wherein $R^2$ is hydrogen, phenyl, benzyl, or a saturated hydrocarbon radical; A is a halide ion. In one example, $R^2$ is an alkyl radical having from 1 to 20 carbon atoms and/or from 2 to 18 carbon atoms and/or from 4 to 12 carbon atoms. In still another example, the terminal aminosilicone is selected from the group consisting of bis-aminomethyl dimethicone, bis-aminoethyl dimethicone, bis-aminopropyl dimethicone, bis-aminobutyl dimethicone, and mixtures thereof.

Non-limiting examples of suitable terminal aminosilicones include aminopropyl terminated polydimethylsiloxane (e.g. having a viscosity of 4,000-6,000 cSt (4-6 Pa·s); available under the tradename DMS-A35 from Gelest, Inc.), polydimethylsiloxane, trimethylsiloxy terminated (e.g. having a viscosity of 5,000 cSt (5 Pa·s); available under the tradename DMS-T35 from Gelest, Inc.), polydimethylsiloxane, trimethylsiloxy terminated (e.g. having a viscosity of 1,000 cSt (1 Pas); available under the tradename DMS-T31 from Gelest, Inc.), aminopropyl terminated polydimethylsiloxane (e.g. having a viscosity of 900-1,100 cSt (0.9-1.1 Pa·s); available under the tradename DMS-A31 from Gelest, Inc.), polydimethylsiloxane, trimethylsiloxy terminated (e.g. having a viscosity of 50 cSt (0.05 Pa·s); available under the tradename DMS-T15 from Gelest, Inc), aminopropyl terminated polydimethylsiloxane (e.g. having a viscosity of 50-60 cSt (0.05-0.06 Pa·s); available under the tradename DMS-A15 from Gelest, Inc.), bis-aminopropyl dimethicone (e.g. having a viscosity of 10,220 cSt (10.2 Pa·s); available from Momentive Performance Materials Inc.), and mixtures thereof.

Non-limiting examples of suitable alkyl siloxane polymers are described in US 2011/0243874 A1, US 2011/0243875 A1, US 2011/0240065 A1, US 2011/0243878A1, US 2011/0243871 A1, and US 2011/0243876 A1.

Non-limiting examples of suitable cationic organopolysiloxanes are described in US 2014/0030206 A1, WO 2014/018985 A1, WO 2014/018986 A1, WO 2014/018987 A1, WO 2014/018988 A1, and WO 2014/018989 A1.

Organic Oils

Non-limiting examples of organic oils of the present disclosure include hydrocarbon oils, polyolefins, fatty esters, metathesized unsaturated polyol esters, silane-modified oils, and mixtures thereof.

In one example, the concentration of the organic oil active agents on and/or in the fibrous elements and/or fibrous structures and/or articles of the present disclosure may be from about 0.5% to about 20% and/or from about 0.05% to about 10% and/or from about 0.05% to about 3% and/or from about 0.08% to about 1.5% and/or from about 0.1% to about 1%.

In one example, the organic oil active agent comprises an average carbon chain length of greater than 20 and/or greater than 30 and/or greater than 40.

Non-limiting examples of hydrocarbon oils include hydrocarbon oils having at least about carbon atoms, such as cyclic hydrocarbons, straight chain aliphatic hydrocarbons (saturated or unsaturated), and branched chain aliphatic hydrocarbons (saturated or unsaturated), including polymers, and mixtures thereof. In one example, the hydrocarbon oil is a straight chain hydrocarbon oil, such as having a carbon chain length of from about $C_{12}$ to about $C_{19}$. In another example, the hydrocarbon oil is a branched chain hydrocarbon oil, including hydrocarbon polymers, having a carbon chain length of greater than 19 carbon atoms.

Non-limiting examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polyisobutylene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, available from Permethyl Corporation. Hydrocarbon polymers such as polybutene and polydecene are also suitable as an organic oil active agent. In one example, a hydrocarbon polymer is polybutene, such as the copolymer of isobutylene and butene. A commercially available material of this type is L-14 polybutene from Amoco Chemical Corporation.

Non-limiting examples of suitable polyolefins include liquid polyolefins, such as liquid poly-α-olefins, for example hydrogenated liquid poly-α-olefins. In one example, the liquid polyolefins of the present disclosure may be prepared by polymerization of from about $C_4$ to about $C_{14}$ and/or from about $C_6$ to about $C_{12}$ olefenic monomers. Non-limiting examples of olefenic monomers for use in preparing the liquid polyolefins include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the liquid polyolefins are olefin-containing refinery feedstocks and/or effluents. In one example, the liquid polyolefin is a liquid poly-α-olefin, for example a hydrogenated liquid poly-α-olefin, such as 1-hexene to 1-hexadecenes, 1-octene to 1-tetradecene, and mixtures thereof.

Non-limiting examples of suitable fatty esters of the present disclosure include fatty esters having at least 10 carbon atoms. Non-limiting examples of such fatty esters include esters with hydrocarbyl chains derived from fatty acids or alcohols (e.g., mono-esters, polyhydric alcohol esters, and di- and tri-carboxylic acid esters). In one example, the hydrocarbyl radicals of the fatty esters hereof may include or have covalently bonded thereto other compatible functionalities, such as amides and alkoxy moieties (e.g., ethoxy or ether linkages, etc.).

Non-limiting examples of fatty esters of the present disclosure include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, oleyl adipate, and mixtures thereof.

In one example, the fatty esters of the present disclosure include mono-carboxylic acid esters of the general formula R'COOR, wherein R' and R are independently alkyl or alkenyl radicals, and the sum of carbon atoms in R' and R is at least 10 and/or at least 22. In another example, the fatty esters of the present disclosure include di- and tri-alkyl and alkenyl esters of carboxylic acids, such as esters of $C_4$ to $C_8$ dicarboxylic acids (e.g. $C_1$ to $C_{22}$ esters, preferably $C_1$ to $C_6$, of succinic acid, glutaric acid, and adipic acid). Non-limiting examples of such di- and tri-alkyl and alkenyl esters of carboxylic acids include isocetyl stearyol stearate, diisopropyl adipate, tristearyl citrate, and mixtures thereof.

In yet another example, the fatty esters of the present disclosure include polyhydric alcohol esters. Non-limiting examples of such polyhydric alcohol esters include alkylene glycol esters, such as ethylene glycol mono and di-fatty acids, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, polyoxy-ethylene sorbitan fatty acid esters, and mixtures thereof.

In still another example, the fatty esters of the present disclosure include glycerides, such as mono-, di-, and tri-glycerides, for example di- and tri-glycerides, such as tri-glycerides. Non-limiting examples of suitable glycerides include the mono-, di-, and tri-esters of glycerol and long chain carboxylic acids, such as $C_{10}$ to $C_{22}$ carboxylic acids. A variety of these types of glycerides can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

In another example, the fatty esters suitable of the present disclosure may include water insoluble synthetic fatty esters. Non-limiting example of such synthetic fatty esters correspond to the general Formula (IX):

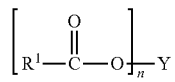

(IX)

wherein $R^1$ is independently a $C_7$ to $C_9$ alkyl, alkenyl, hydroxyalkyl or hydroxyalkenyl group, such as a saturated alkyl group, for example a saturated, linear, alkyl group; n is a positive integer having a value from 2 to 4, such as 3; and Y is an alkyl, alkenyl, hydroxy or carboxy substituted alkyl or alkenyl, having from about 2 to about 20 and/or from about 3 to 14 carbon atoms. In one example, such synthetic fatty esters conform to the general Formula (X):

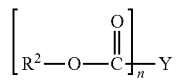

(X)

wherein $R^2$ is independently a $C_8$ to $C_{10}$ alkyl, alkenyl, hydroxyalkyl or hydroxyalkenyl group; such as a saturated alkyl group, for example a saturated, linear, alkyl group; n and Y are as defined above in Formula (IX).

Non-limiting examples of suitable synthetic fatty esters of the present disclosure include P-43 ($C_8$-$C_{10}$ triester of trimethylolpropane), MCP-684 (tetraester of 3,3 diethanol-1,5 pentadiol), MCP 121 ($C_8$-$C_{10}$ diester of adipic acid), all of which are commercially available from Mobil Chemical Company.

Non-limiting examples of metathesized unsaturated polyol esters and their starting materials are set forth in US 2009/0220443 A1 and in US 2016/0244915 A1. A metathesized unsaturated polyol ester refers to the product obtained when one or more unsaturated polyol ester ingredient(s) are subjected to a metathesis reaction. Metathesis is a catalytic reaction that involves the interchange of alkylidene units among compounds containing one or more double bonds (i.e., olefinic compounds) via the formation and cleavage of the carbon-carbon double bonds. Metathesis may occur between two of the same molecules (often referred to as self-metathesis) and/or it may occur between two different molecules (often referred to as cross-metathesis).

Non-limiting examples of suitable silane-modified oils include silane-modified oils having a hydrocarbon chain selected from the group consisting of saturated oil, unsaturated oil, and mixtures thereof; and a hydrolysable silyl group covalently bonded to the hydrocarbon chain. Non-limiting examples of suitable silane-modified oils are described in US 2014/0335032 A1.

Release of Active Agent

One or more active agents may be released from the fibrous element and/or particle and/or fibrous structure when the fibrous element and/or particle and/or fibrous structure is exposed to a triggering condition. In one example, one or more active agents may be released from the fibrous element and/or particle and/or fibrous structure or a part thereof when the fibrous element and/or particle and/or fibrous structure or the part thereof loses its identity, in other words, loses its physical structure. For example, a fibrous element and/or particle and/or fibrous structure loses its physical structure when the filament-forming material dissolves, melts or undergoes some other transformative step such that its structure is lost. In one example, the one or more active agents are released from the fibrous element and/or particle and/or fibrous structure when the fibrous element's and/or particle's and/or fibrous structure's morphology changes.

In another example, one or more active agents may be released from the fibrous element and/or particle and/or fibrous structure or a part thereof when the fibrous element and/or particle and/or fibrous structure or the part thereof alters its identity, in other words, alters its physical structure rather than loses its physical structure. For example, a fibrous element and/or particle and/or fibrous structure alters its physical structure when the filament-forming material swells, shrinks, lengthens, and/or shortens, but retains its filament-forming properties.

In another example, one or more active agents may be released from the fibrous element and/or particle and/or fibrous structure with its morphology not changing (not losing or altering its physical structure).

In one example, the fibrous element and/or particle and/or fibrous structure may release an active agent upon the fibrous element and/or particle and/or fibrous structure being exposed to a triggering condition that results in the release of the active agent, such as by causing the fibrous element and/or particle and/or fibrous structure to lose or alter its identity as discussed above. Non-limiting examples of triggering conditions include exposing the fibrous element and/or particle and/or fibrous structure to solvent, a polar solvent, such as alcohol and/or water, and/or a non-polar solvent, which may be sequential, depending upon whether the filament-forming material comprises a polar solvent-soluble material and/or a non-polar solvent-soluble material; exposing the fibrous element and/or particle and/or fibrous structure to heat, such as to a temperature of greater than 75° F. and/or greater than 100° F. and/or greater than 150° F. and/or greater than 200° F. and/or greater than 212° F.; exposing the fibrous element and/or particle and/or fibrous structure to cold, such as to a temperature of less than 40° F. and/or less than 32° F. and/or less than 0° F.; exposing the fibrous element and/or particle and/or fibrous structure to a force, such as a stretching force applied by a consumer using the fibrous element and/or particle and/or fibrous structure; and/or exposing the fibrous element and/or particle and/or fibrous structure to a chemical reaction; exposing the fibrous element and/or particle and/or fibrous structure to a condition that results in a phase change; exposing the fibrous element and/or particle and/or fibrous structure to a pH change and/or a pressure change and/or temperature change; exposing the fibrous element and/or particle and/or fibrous structure to one or more chemicals that result in the fibrous element and/or particle and/or fibrous structure releasing one or more of its active agents; exposing the fibrous element and/or particle and/or fibrous structure to ultrasonics; exposing the fibrous element and/or particle and/or fibrous structure to light and/or certain wavelengths; exposing the fibrous element and/or particle and/or fibrous structure to a different ionic strength; and/or exposing the fibrous element and/or particle and/or fibrous structure to an active agent released from another fibrous element and/or particle and/or fibrous structure.

In one example, one or more active agents may be released from the fibrous elements and/or particles of the present disclosure when a fibrous structure product comprising the fibrous elements and/or particles is subjected to a triggering step selected from the group consisting of: pre-treating stains on a fabric article with the fibrous structure product; forming a wash liquor by contacting the fibrous structure product with water; tumbling the fibrous structure product in a dryer; heating the fibrous structure product in a dryer; and combinations thereof.

Filament-forming Composition

The fibrous elements of the present disclosure are made from a filament-forming composition. The filament-forming composition is a polar-solvent-based composition. In one example, the filament-forming composition is an aqueous composition comprising one or more filament-forming materials and one or more active agents.

The filament-forming composition of the present disclosure may have a shear viscosity as measured according to the Shear Viscosity Test Method described herein of from about 1 Pascal·Seconds to about 25 Pascal·Seconds and/or from about 2 Pascal·Seconds to about 20 Pascal·Seconds and/or from about 3 Pascal·Seconds to about 10 Pascal·Seconds, as measured at a shear rate of 3,000 sec$^{-1}$ and at the processing temperature (50° C. to 100° C.).

The filament-forming composition may be processed at a temperature of from about 50° C. to about 100° C. and/or from about 65° C. to about 95° C. and/or from about 70° C. to about 90° C. when making fibrous elements from the filament-forming composition.

In one example, the filament-forming composition may comprise at least 20% and/or at least 30% and/or at least 40% and/or at least 45% and/or at least 50% to about 90% and/or to about 85% and/or to about 80% and/or to about 75% by weight of one or more filament-forming materials, one or more active agents, and mixtures thereof. The filament-forming composition may comprise from about 10% to about 80% by weight of a polar solvent, such as water.

In one example, non-volatile components of the filament-forming composition may comprise from about 20% and/or 30% and/or 40% and/or 45% and/or 50% to about 75% and/or 80% and/or 85% and/or 90% by weight based on the total weight of the filament-forming composition. The non-volatile components may be composed of filament-forming materials, such as backbone polymers, active agents and combinations thereof. Volatile components of the filament-forming composition will comprise the remaining percentage and range from 10% to 80% by weight based on the total weight of the filament-forming composition.

In a fibrous element spinning process, the fibrous elements need to have initial stability as they leave the spinning die. Capillary Number is used to characterize this initial stability criterion. At the conditions of the die, the Capillary Number should be at least 1 and/or at least 3 and/or at least 4 and/or at least 5.

In one example, the filament-forming composition exhibits a Capillary Number of from at least 1 to about 50 and/or at least 3 to about 50 and/or at least 5 to about 30 such that the filament-forming composition can be effectively polymer processed into a fibrous element.

"Polymer processing" as used herein means any spinning operation and/or spinning process by which a fibrous element comprising a processed filament-forming material is formed from a filament-forming composition. The spinning operation and/or process may include spun bonding, melt blowing, electro-spinning, rotary spinning, continuous filament producing and/or tow fiber producing operations/processes. A "processed filament-forming material" as used herein means any filament-forming material that has undergone a melt processing operation and a subsequent polymer processing operation resulting in a fibrous element.

The Capillary number is a dimensionless number used to characterize the likelihood of this droplet breakup. A larger capillary number indicates greater fluid stability upon exiting the die. The Capillary number is defined as follows:

$$Ca = \frac{V * \eta}{\sigma}$$

V is the fluid velocity at the die exit (units of Length per Time), $\eta$ is the fluid viscosity at the conditions of the die (units of Mass per Length*Time), $\sigma$ is the surface tension of the fluid (units of mass per Time$^2$). When velocity, viscosity, and surface tension are expressed in a set of consistent units, the resulting Capillary number will have no units of its own; the individual units will cancel out.

The Capillary number is defined for the conditions at the exit of the die. The fluid velocity is the average velocity of the fluid passing through the die opening. The average velocity is defined as follows:

$$V = \frac{Vol'}{Area}$$

Vol'=volumetric flowrate (units of Length$^3$ per Time),
Area=cross-sectional area of the die exit (units of Length$^2$).

When the die opening is a circular hole, then the fluid velocity can be defined as $$V = \frac{Vol'}{\pi * R^2}$$

R is the radius of the circular hole (units of length).

The fluid viscosity will depend on the temperature and may depend of the shear rate. The definition of a shear thinning fluid includes a dependence on the shear rate. The surface tension will depend on the makeup of the fluid and the temperature of the fluid.

In one example, the filament-forming composition may comprise one or more release agents and/or lubricants. Non-limiting examples of suitable release agents and/or lubricants include fatty acids, fatty acid salts, fatty alcohols, fatty esters, sulfonated fatty acid esters, fatty amine acetates and fatty amides, silicones, aminosilicones, fluoropolymers and mixtures thereof.

In one example, the filament-forming composition may comprise one or more antiblocking and/or detackifying agents. Non-limiting examples of suitable antiblocking and/or detackifying agents include starches, modified starches, crosslinked polyvinylpyrrolidone, crosslinked cellulose, microcrystalline cellulose, silica, metallic oxides, calcium carbonate, talc and mica.

Active agents of the present disclosure may be added to the filament-forming composition prior to and/or during fibrous element formation and/or may be added to the fibrous element after fibrous element formation. For example, a perfume active agent may be applied to the fibrous element and/or fibrous structure comprising the fibrous element after the fibrous element and/or fibrous structure according to the present disclosure are formed. In another example, an enzyme active agent may be applied to the fibrous element and/or fibrous structure comprising the fibrous element after the fibrous element and/or fibrous structure according to the present disclosure are formed. In still another example, one or more particles, which may not be suitable for passing through the spinning process for making the fibrous element, may be applied to the fibrous element and/or fibrous structure comprising the fibrous element after the fibrous element and/or fibrous structure according to the present disclosure are formed.

Extensional Aids

In one example, the fibrous element comprises an extensional aid. Non-limiting examples of extensional aids can include polymers, other extensional aids, and combinations thereof.

In one example, the extensional aids have a weight-average molecular weight of at least about 500,000 Da. In another example, the weight average molecular weight of the extensional aid is from about 500,000 to about 25,000,000, in another example from about 800,000 to about 22,000,000, in yet another example from about 1,000,000 to about 20,000,000, and in another example from about 2,000,000 to about 15,000,000. The high molecular weight extensional aids are preferred in some examples due to the ability to increase extensional melt viscosity and reducing melt fracture.

The extensional aid, when used in a meltblowing process, is added to the composition of the present disclosure in an amount effective to visibly reduce the melt fracture and capillary breakage of fibers during the spinning process such that substantially continuous fibers having relatively consistent diameter can be melt spun. Regardless of the process employed to produce fibrous elements and/or particles, the extensional aids, when used, can be present from about 0.001% to about 10%, by weight on a dry fibrous element basis and/or dry particle basis and/or dry fibrous structure basis, in one example, and in another example from about 0.005 to about 5%, by weight on a dry fibrous element basis and/or dry particle basis and/or dry fibrous structure basis, in yet another example from about 0.01 to about 1%, by weight on a dry fibrous element basis and/or dry particle basis and/or dry fibrous structure basis, and in another example from about 0.05% to about 0.5%, by weight on a dry fibrous element basis and/or dry particle basis and/or dry fibrous structure basis.

Non-limiting examples of polymers that can be used as extensional aids can include alginates, carrageenans, pectin, chitin, guar gum, xanthum gum, agar, gum arabic, karaya gum, tragacanth gum, locust bean gum, alkylcellulose, hydroxyalkylcellulose, carboxyalkylcellulose, and mixtures thereof.

Nonlimiting examples of other extensional aids can include modified and unmodified polyacrylamide, polyacrylic acid, polymethacrylic acid, polyvinyl alcohol, polyvinylacetate, polyvinylpyrrolidone, polyethylene vinyl acetate, polyethyleneimine, polyamides, polyalkylene oxides including polyethylene oxide, polypropylene oxide, polyethylenepropylene oxide, and mixtures thereof.

Method for Making Fibrous Elements

The fibrous elements of the present disclosure may be made by any suitable process. A non-limiting example of a suitable process for making the fibrous elements is described below.

Figure 12:
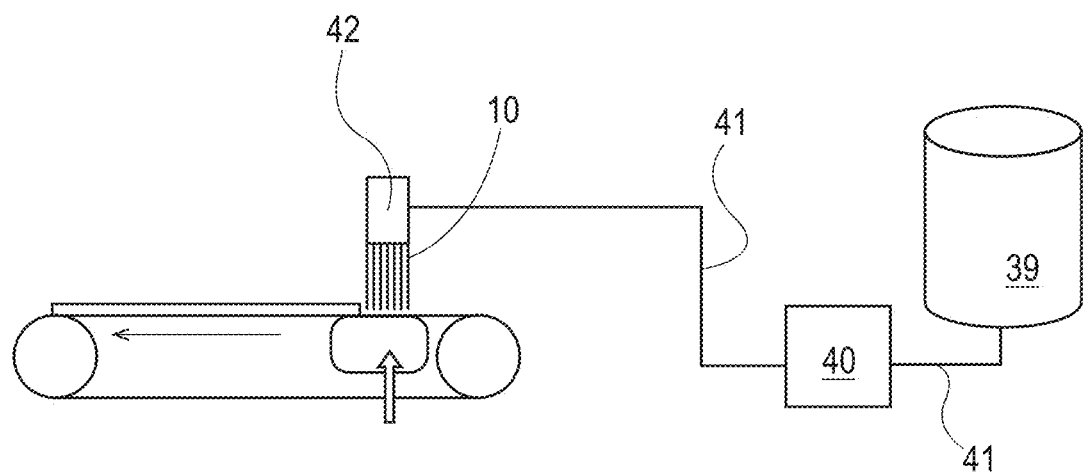
FIG. 12 is a schematic representation of an example of a process for making an example of a fibrous structure according to the present disclosure.
Figure 13:
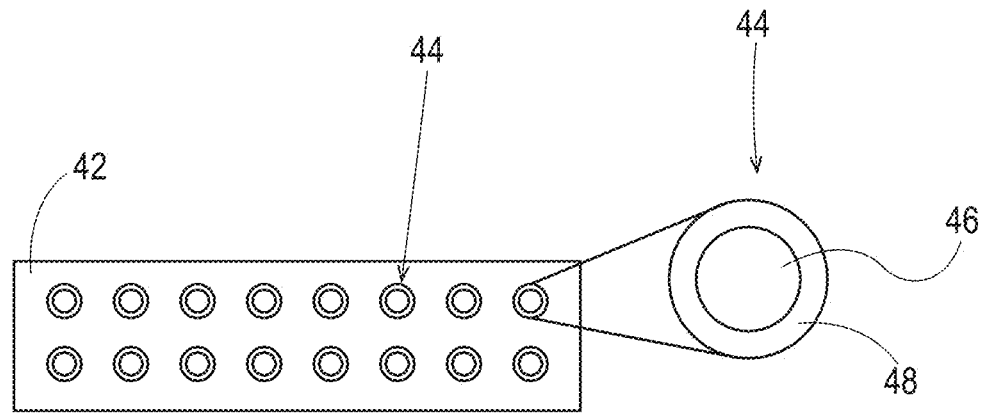
FIG. 13 is a schematic representation of an example of a die with a magnified view used in the process of FIG. 12.

As shown in FIGS. 12 and 13, the fibrous elements of the present disclosure may be made as follows. Fibrous elements may be formed by means of a small-scale apparatus, a schematic representation of which is shown in FIGS. 12 and 13. A pressurized tank 39, suitable for batch operation is filled with a suitable filament-forming composition according to the present disclosure. A pump 40 such as a Zenith®, type PEP II, having a capacity of 5.0 cubic centimeters per revolution (cc/rev), manufactured by Parker Hannifin Corporation, Zenith Pumps division, of Sanford, N.C., USA may be used to facilitate transport of the filament-forming composition via pipes 41 to a spinning die 42. The flow of the filament-forming composition from the pressurized tank 39 to the spinning die 42 may be controlled by adjusting the number of revolutions per minute (rpm) of the pump 40. Pipes 41 are used to connect the pressurized tank 39, the pump 40, and the spinning die 42.

The spinning die 42 shown in FIG. 13 has several rows of circular extrusion nozzles (fibrous element-forming holes 44) spaced from one another at a pitch P of about 1.524 millimeters (about 0.060 inches). The nozzles have individual inner diameters of about 0.305 millimeters (about 0.012 inches) and individual outside diameters of about 0.813 millimeters (about 0.032 inches). Each individual nozzle is encircled by an annular and divergently flared orifice (concentric attenuation fluid hole 48 to supply attenuation air to each individual melt capillary 46. The filament-forming composition extruded through the nozzles is surrounded and attenuated by generally cylindrical, humidified air streams supplied through the orifices.

In one example, as shown in FIGS. 12 and 13, a method 47 for making a fibrous element 10 according to the present disclosure comprises the steps of:

a. providing a filament-forming composition comprising one or more filament-forming materials, and optionally one or more active agents; and b. spinning the filament-forming composition, such as via a spinning die 42, into one or more fibrous elements, such as filaments 10, comprising the one or more filament-forming materials and optionally, the one or more active agents. The one or more active agents may be releasable from the fibrous element when exposed to conditions of intended use. The total level of the one or more filament-forming materials present in the fibrous element, for example filament 10, when active agents are present therein, may be less than 80% and/or less than 70% and/or less than 65% and/or 50% or less by weight on a dry fibrous element basis and/or dry fibrous structure basis and the total level of the one or more active agents, when present in the fibrous element may be greater than 20% and/or greater than 35% and/or 50% or greater 65% or greater and/or 80% or greater by weight on a dry fibrous element basis and/or dry fibrous structure basis.

As shown in FIG. 13, the spinning die 42 may comprise a plurality of fibrous element-forming holes 44 that include a melt capillary 46 encircled by a concentric attenuation fluid hole 48 through which a fluid, such as air, passes to facilitate attenuation of the filament-forming composition into a fibrous element, for example a filament 10 as it exits the fibrous element-forming hole 44.

Attenuation air can be provided by heating compressed air from a source by an electrical-resistance heater, for example, a heater manufactured by Chromalox, Division of Emerson Electric, of Pittsburgh, Pa., USA. An appropriate quantity of steam was added to saturate or nearly saturate the heated air at the conditions in the electrically heated, thermostatically controlled delivery pipe. Condensate is removed in an electrically heated, thermostatically controlled, separator.

The embryonic fibrous elements are dried by a drying air stream having a temperature from about 149° C. (about 300° F.) to about 315° C. (about 600° F.) by an electrical resistance heater (not shown) supplied through drying nozzles and discharged at an angle of about 90° relative to the general orientation of the embryonic fibrous elements being extruded. The dried embryonic fibrous elements are collected on a collection device, such as, for example, a movable foraminous belt or patterned collection belt. The addition of a vacuum source directly under the formation zone may be used to aid collection of the fibers.

In one example, during the spinning step, any volatile solvent, such as water, present in the filament-forming composition is removed, such as by drying, as the fibrous element 10 is formed. In one example, greater than 30% and/or greater than 40% and/or greater than 50% of the weight of the filament-forming composition's volatile solvent, such as water, is removed during the spinning step, such as by drying the fibrous element being produced.

The filament-forming composition may comprise any suitable total level of filament-forming materials and any suitable level of active agents so long as the fibrous element produced from the filament-forming composition comprises a total level of filament-forming materials in the fibrous element of from about 5% to 50% or less by weight on a dry fibrous element basis and/or dry particle basis and/or dry fibrous structure basis and a total level of active agents in the fibrous element of from 50% to about 95% by weight on a dry fibrous element basis and/or dry particle basis and/or dry fibrous structure basis.

In one example, the filament-forming composition may comprise any suitable total level of filament-forming materials and any suitable level of active agents so long as the fibrous element produced from the filament-forming composition comprises a total level of filament-forming materials in the fibrous element and/or particle of from about 5% to 50% or less by weight on a dry fibrous element basis and/or dry particle basis and/or dry fibrous structure basis and a total level of active agents in the fibrous element and/or particle of from 50% to about 95% by weight on a dry fibrous element basis and/or dry particle basis and/or dry fibrous structure basis, wherein the weight ratio of filament-forming material to total level of active agents is 1 or less.

In one example, the filament-forming composition comprises from about 1% and/or from about 5% and/or from about 10% to about 50% and/or to about 40% and/or to about 30% and/or to about 20% by weight of the filament-forming composition of filament-forming materials; from about 1% and/or from about 5% and/or from about 10% to about 50% and/or to about 40% and/or to about 30% and/or to about 20% by weight of the filament-forming composition of active agents; and from about 20% and/or from about 25% and/or from about 30% and/or from about 40% and/or to about 80% and/or to about 70% and/or to about 60% and/or to about 50% by weight of the filament-forming composition of a volatile solvent, such as water. The filament-forming composition may comprise minor amounts of other active agents, such as less than 10% and/or less than 5% and/or less than 3% and/or less than 1% by weight of the filament-forming composition of plasticizers, pH adjusting agents, and other active agents.

The filament-forming composition is spun into one or more fibrous elements and/or particles by any suitable spinning process, such as meltblowing, spunbonding, electro-spinning, and/or rotary spinning. In one example, the filament-forming composition is spun into a plurality of fibrous elements and/or particles by meltblowing. For example, the filament-forming composition may be pumped from a tank to a meltblown spinnerette. Upon exiting one or more of the filament-forming holes in the spinnerette, the filament-forming composition is attenuated with air to create one or more fibrous elements and/or particles. The fibrous elements and/or particles may then be dried to remove any remaining solvent used for spinning, such as the water.

The fibrous elements and/or particles of the present disclosure may be collected on a belt, such as a patterned belt to form a fibrous structure comprising the fibrous elements and/or particles.

Method for Making Fibrous Structures

Figure 14:
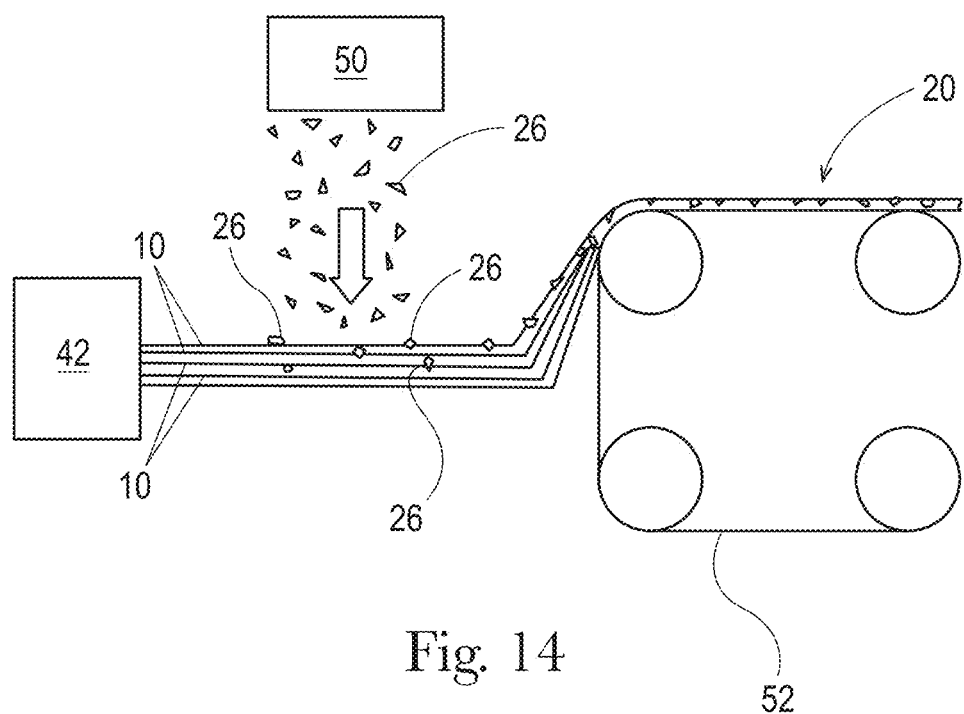
FIG. 14 is a schematic representation of an example of another process for making an example of a fibrous structure according to the present disclosure.

As shown in FIG. 14, a fibrous structure, for example a fibrous structure layer or ply 22 of the present disclosure may be made by spinning a filament-forming composition from a spinning die 42, as described in FIGS. 12 and 13, to form a plurality of fibrous elements, such as filaments 10, and then optionally, associating one or more particles 26 provided by a particle source 50, for example a sifter or a airlaid forming head. The particles 26 may be dispersed within the fibrous elements, for example filaments 10. The mixture of particles 26 and fibrous elements, for example filaments 10 may be collected on a collection belt 52, such as a patterned collection belt that imparts a texture, such as a three-dimensional texture to at least one surface of the fibrous structure layer or ply 22.

Figure 15:
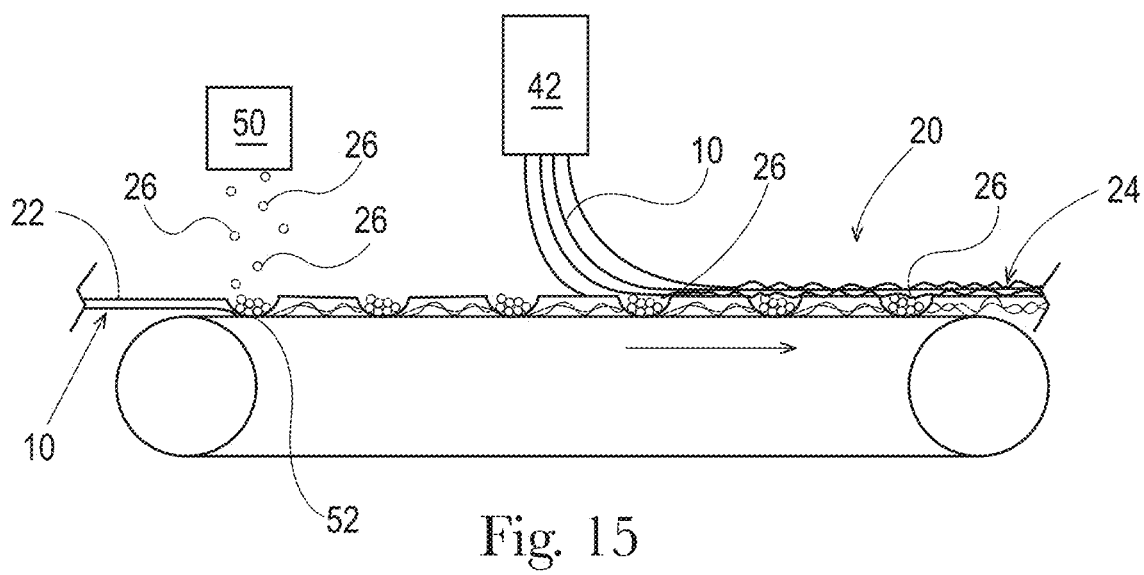
FIG. 15 is a schematic representation of another example of a process for making another example of a fibrous structure according to the present disclosure.

FIG. 15 illustrates an example of a method for making an article 20 according to FIG. 5. The method comprises the steps of forming a first fibrous structure layer 22 of a plurality of fibrous elements, for example filaments 10 such that pockets 28 are formed in a surface of the first fibrous structure layer 22. One or more particles 26 are deposited into the pockets 28 from a particle source 50. A second fibrous structure layer 24 comprising a plurality of fibrous elements, for example filaments 10 produced from a spinning die 42 are then formed on the surface of the first fibrous structure layer 22 such that the particles 26 are entrapped in the pockets 28.

Figure 16:
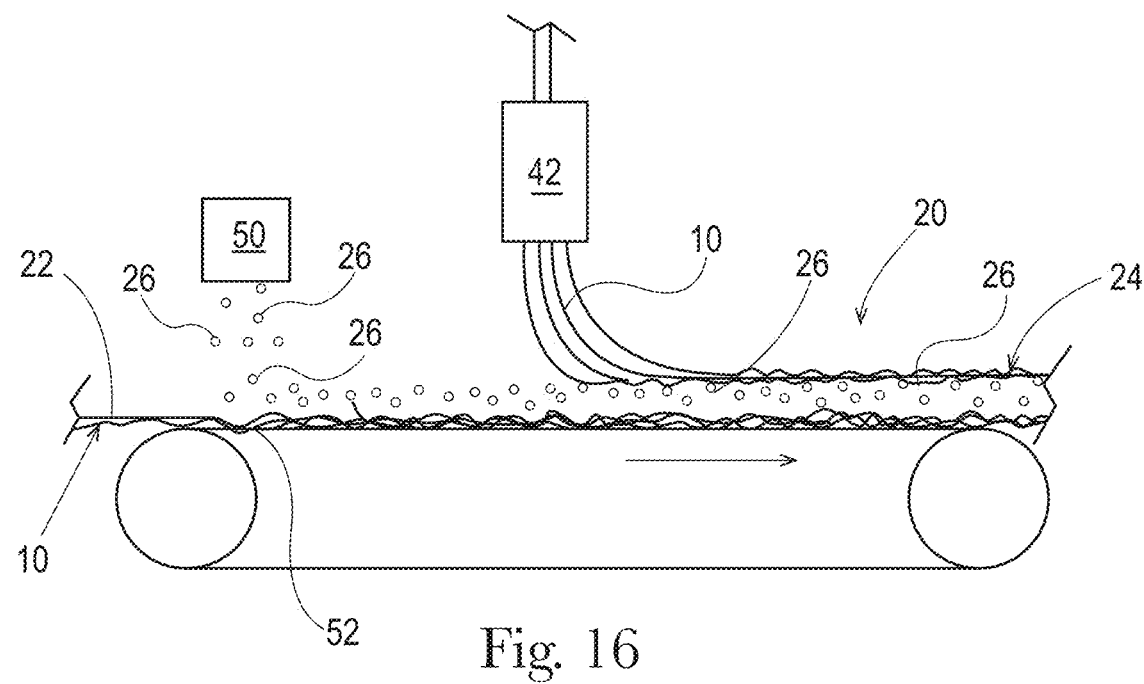
FIG. 16 is a schematic representation of another example of a process for making another example of a fibrous structure according to the present disclosure.

FIG. 16 illustrates yet another example of a method for making an article 20 according to FIG. 4. The method comprises the steps of forming a first fibrous structure layer 22 of a plurality of fibrous elements, for example filaments 10. One or more particles 26 are deposited onto a surface of the first fibrous structure layer 22 from a particle source 50. A second fibrous structure layer 24 comprising a plurality of fibrous elements, for example filaments 10 produced from a spinning die 42 are then formed on top of the particles 26 such that the particles 26 are positioned between the first fibrous structure layer 22 and the second fibrous structure layer 24.

Figure 17:
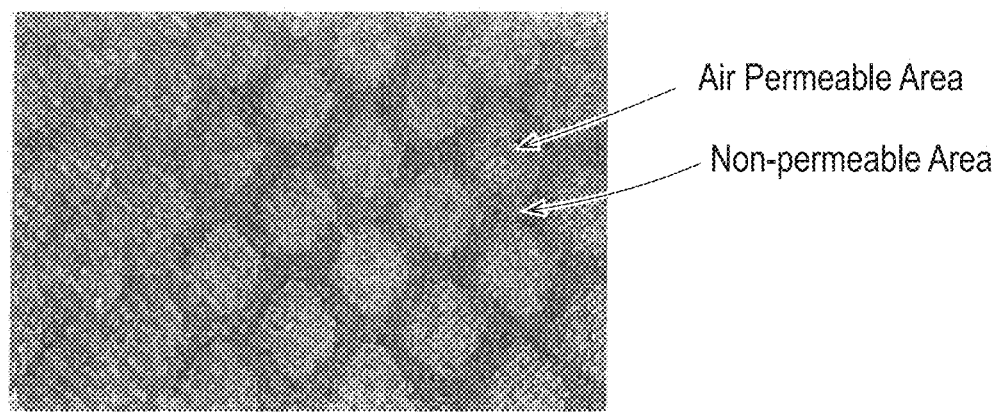
FIG. 17 is a representative image of an example of a patterned belt useful in the processes for making the fibrous structure according to the present disclosure.
Figure 20:
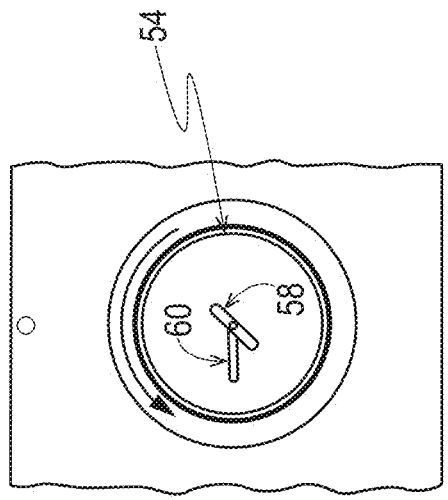
FIG. 20 is a schematic representation of a top view of FIG. 19.
Figure 19:
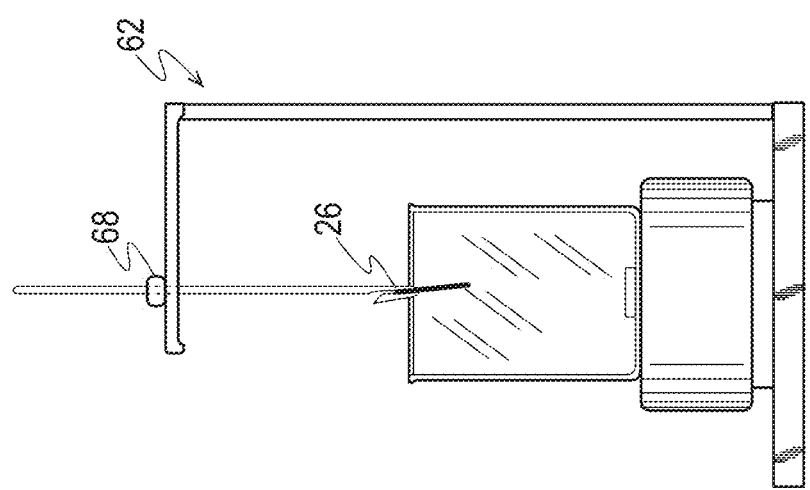
FIG. 19 is a schematic representation of FIG. 18 with during the operation of the dissolution test.

The dry embryonic fibrous elements, for example filaments may be collected on a molding member as described above. The construction of the molding member may provide areas that are air-permeable due to the inherent construction. The filaments that are used to construct the molding member will be non-permeable while the void areas between the filaments will be permeable. Additionally a pattern may be applied to the molding member to provide additional non-permeable areas which may be continuous, discontinuous, or semi-continuous in nature. A vacuum used at the point of lay down is used to help deflect fibers into the presented pattern. An example of one of these molding members is shown in FIG. 17.

In addition to the techniques described herein in forming regions within the fibrous structures having a different properties (e.g., average densities), other techniques can also be applied to provide suitable results. One such example includes embossing techniques to form such regions. Suitable embossing techniques are described in U.S. Patent Application Publication Nos. 2010/0297377, 2010/0295213, 2010/0295206, 2010/0028621, and 2006/0278355.

In one example, in a multi-ply article, one or more fibrous structure plies may be formed and/or deposited directly upon an existing ply of fibrous structure to form a multi-ply fibrous structure. The two or more existing fibrous structure plies may be combined, for example via thermal bonding, gluing, embossing, aperturing, rodding, rotary knife aperturing, die cutting, die punching, needlepunching, knurling, pneumatic forming, hydraulic forming, laser cutting, tufting, and/or other mechanical combining process, with one or more other existing fibrous structure plies to form the multi-ply article of the present disclosure.

Non-limiting Examples of Fibrous Structures (F)

Example 1F-A fibrous structure is made from the formula set forth in Table 1A below according to the present disclosure.

TABLE 1A

| Material | Trade Name (where applicable) | Composition % (bone dry basis) |
|---|---|---|
| Citric Acid, Anhydous | Citric Acid | 0.95 |
| Sodium Benzoate, NF | Sodium Benzoate | 0.42 |
| Guar hydroxypropyltrimonium Chloride | Jaguar C500 | 1.27 |
| Polyquatenium 76 | Mirapol AT-1 | 0.24 |
| Polyvinyl Alcohol | PVA420H | 13.06 |
| Polyvinyl Alcohol | PVA403 | 13.06 |
| Lauryl Hydroxysultaine | Mackam LHS | 16.20 |
| Sodium Chloride (constituent from LHS) | Salt | 2.86 |
| Sodium Laureth 1 Sulfate | Sodium Laureth (1) Sulfate | 29.69 |
| Sodium Laureth 3 Sulfate | Sodium Laureth (3) Sulfate | 4.01 |
| Sodium Undecyl Sulfate | Sodium Undecyl Sulfate | 18.25 |

Example 2F-A fibrous structure is made from the formula set forth in Table 1B below according to the present disclosure.

TABLE 1B

| | Filament-forming composition (i.e., premix) (%) | Filament-Forming Composition (%) | Filament (i.e., components remaining upon drying) (%) | Percent by weight on a dry filament basis (%) |
|---|---|---|---|---|
| C12-15 AES | 28.45 | 11.38 | 11.38 | 28.07 |
| C11.8 HLAS | 12.22 | 4.89 | 4.89 | 12.05 |
| MEA | 7.11 | 2.85 | 2.85 | 7.02 |
| N67HSAS | 4.51 | 1.81 | 1.81 | 4.45 |
| Glycerol | 3.08 | 1.23 | 1.23 | 3.04 |
| PE-20, Polyethyleneimine Ethoxylate, PEI 600 E20 | 3.00 | 1.20 | 1.20 | 2.95 |
| Ethoxylated/Propoxylated Polyethyleneimine | 2.95 | 1.18 | 1.18 | 2.91 |
| Brightener 15 | 2.20 | 0.88 | 0.88 | 2.17 |
| Amine Oxide | 1.46 | 0.59 | 0.59 | 1.44 |
| Sasol 24,9 Nonionic Surfactant | 1.24 | 0.50 | 0.50 | 1.22 |
| DTPA (Chelant) | 1.08 | 0.43 | 0.43 | 1.06 |
| Tiron (Chelant) | 1.08 | 0.43 | 0.43 | 1.06 |
| Celvol 523 PVOH[1] | 0.000 | 13.20 | 13.20 | 32.55 |
| Water | 31.63 | 59.43 | — | — |

Non-limiting Examples of Articles (A)

Example 1A—A fibrous structure according to the present disclosure having nominal basis weight of about 295 gsm and thickness of approximately 1 mm is made according to the present disclosure, such as Example 1F or Example 2F above. The fibrous structure is then cut into 3 strips 7" wide×10" long and equilibrated at about 23° C. (73° F.) and 42% relative humidity for 1 hour. An adhesive composition (described in Table 2 below) is applied in a regular pattern to one surface each of the $1^{st}$ and $2^{nd}$ strips. The adhesive composition is applied at approximately 20-25 psi using an air pressure actuated syringe with a 25 gauge tapered tip, for example a Nordson-EFD Ultimus/Optimum system commercially available from Nordson Corporation. The syringe tip is passed over the web at approximately 120 mm/sec, forming essentially linear beads of adhesive composition at a spacing of approximately 8 mm. The resulting beads have an average 17 gsm coating weight as calculated over entire sheet area.

The resulting strips (2 adhesive coated and 1 uncoated) are stacked such that the adhesive is sandwiched between the individual strips, forming a 3-strip (3-ply) stack. Light pressure (approximately 0.09-0.12 psi) is applied uniformly over the surface of the stack for 5 seconds to adhere the strips to one another.

Figure 18:
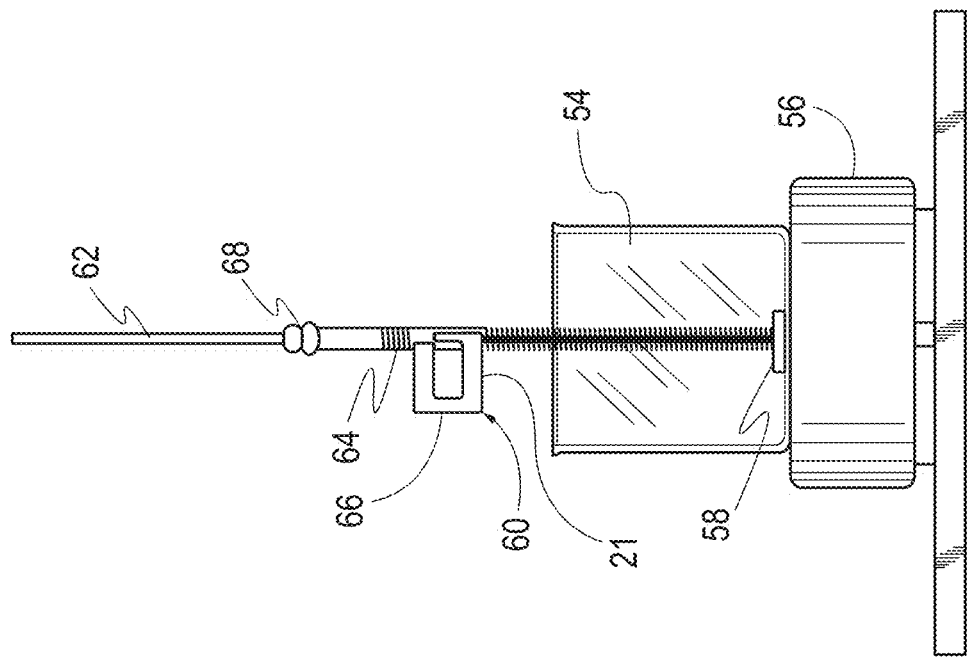
FIG. 18 is a schematic representation of an example of a setup of equipment used in measuring dissolution according to the present disclosure.

The resulting 3-ply laminated article 54 is then apertured to create apertures penetrating through the 3-ply laminated article 54 by passing the 3-ply laminated article 54 through a nip of a rotary knife aperturing apparatus 56 as shown in FIGS. 17 and 18 and described further below. The aperturing process serves a dual purpose—to provide channels for rapid water penetration into the 3-ply laminated article 54 and to further secure the plies together. The 3-ply laminated article 54 is passed through a nip that comprises a 100 pitch toothed roll (rotary knife aperturing roll—100 pitch ROD tooling) intermeshed with a 100 pitch ring roll forming roughly conical apertures from one side of the 3-ply laminated article 54. The teeth on the toothed roll have a pyramidal shape tip with six sides that taper from the base section of the tooth to a sharp point at the tip. The base section of the tooth has vertical leading and trailing edges and is joined to the pyramidal shape tip and the surface of the toothed roller. The teeth are oriented so the long direction runs in the machine direction (MD). The teeth are arranged in a staggered pattern, with a cross-machine direction (CD) pitch P of 0.100 inch (2.5 mm) and a uniform tip to tip spacing in the machined direction of 0.223 inch (5.7 mm). The overall tooth height TH (including pyramidal and vertical base sections) is 0.270 inch (6.9 mm), the side wall angle on the long side of the tooth is 6.8 degrees and the side wall angle of the leading and trailing edges of the teeth in the pyramidal tip section is 25°. The 100 pitch ring roll also has a CD pitch P of 0.100 inch, a tooth height TH of 0.270 inch, a tip radius TR of 0.005 inch, and a side wall angle of 4.7 degrees. The toothed roll (rotary knife aperturing roll) and ring roll are aligned in the CD such that the clearances on either side of the teeth are about equal. The depth of engagement between the toothed and ring rolls is set to about 0.070 inches. The 3-ply laminated article is passed through the nip with essentially zero wrap around the rolls both ingoing and outgoing. While not required by the present disclosure, a sacrificial polymeric spunbond web of approximately 20 gsm is passed through the nip between the 3-ply laminated article and the toothed roller to provide a convenient means to strip the 3-ply laminated article from the toothed roller. The 3-ply laminated article is passed through the nip at a speed of about 10 fpm.

The resulting apertured 3-ply laminated article 58 is then cut into ovals having a minor axis of 40 mm and a major axis of 55 mm using a hydraulic press with a rule die of the same dimensions.

TABLE 2

| Raw Material | Formula (%) |
| --- | --- |
| Distilled Water | 40.3000 |
| SLE1S (surfactant paste) | 58.3000 |
| Polyox N60K (polyethylene oxide) | 0.1700 |
| Polyox N750 (polyethylene oxide) | 1.5000 |
| Total | 100.0000 |

Example 2A—A 3-ply laminated article is made according to Example 1 above except the tapered tip used for glue application is replaced with a 22 gauge tapered tip and pressure is adjusted to 15-17 psi to deliver approximately 73 gsm of coat weight.

Example 3A—A 3-ply laminated article is made according to Example 1 above except that no adhesive application or pressure is applied to the strips of the 3-ply laminated article prior to aperturing the 3-ply laminated article.

Example 4A—A 3-ply laminated article is made according to Example 3 above except that the nip comprises two 100 pitch toothed roll (rotary knife aperturing roll—100 pitch ROD tooling) arranged such that their respective teeth intermesh with the other's respective teeth at a Depth of Engagement of 0.225 inches. This configuration forms roughly conical shaped apertures, half oriented towards one surface of the 3-ply laminated article and half towards the opposite surface, in an alternating grid pattern.

Table 3 below shows the respective properties exhibited by the articles of Examples 1 to 4 of the present disclosure. The data shows that desired ply bond, lap shear, modified circular bending, and/or hand dissolution performance levels are achieved in the articles of the present disclosure.

TABLE 3

| | Example 1A | Example 2A | Example 3A | Example 4A |
| --- | --- | --- | --- | --- |
| Inter-Ply, Intra-Ply, & Whole 180° Peel | | | | |
| Average Inter-Ply Peak Force (N) | 0.31 | 0.38 | 0.04 | 0.04 |
| Average Inter-Ply Average Peel Force (N) | 0.18 | 0.26 | 0.02 | 0.03 |
| Average Intra-Ply Peak Force (N) | 0.45 | 0.54 | 0.25 | 0.21 |
| Average Intra-Ply Average Peel Force (N) | 0.28 | 0.36 | 0.16 | 0.14 |
| Average Whole 180 Peel Peak Force (N) | 0.31 | 0.38 | 0.04 | 0.04 |
| Average Whole 180° Peel Average Force (N) | 0.18 | 0.26 | 0.02 | 0.03 |
| Lap Shear | | | | |
| Average Lap Shear Peak Force (N) | 3.39 | 9.89 | 0.17 | 0.65 |
| Average Lap Shear Average Energy (N * mm) | 11.79 | 36.79 | 0.57 | 0.82 |
| Modified Circular Bend | | | | |
| Average Maximum Peak Force (N) | 8.39 | 8.40 | 7.17 | 5.03 |
| Average Bending Stiffness (N/m) | 1827.5 | 1515.1 | 1647.8 | 808.5 |
| Hand Dissolution Test | | | | |
| Average Hand Dissolution Value (strokes) | 15 | 30 | 5 | Not Tested |
| Article Dimensions and Properties | | | | |
| Length (cm) | 5.50 | 5.50 | 5.50 | 5.50 |
| Width (cm) | 4.00 | 4.00 | 4.00 | 4.00 |
| Height (mm) | 2.80 | 2.80 | 2.80 | 2.80 |
| Volume (cc) | 4.84 | 4.84 | 4.84 | 4.84 |
| Mass (g) | 1.56 | 1.66 | 1.53 | 1.53 |
| Density (g/cc) | 0.33 | 0.34 | 0.32 | 0.32 |

Automatic Dishwashing Articles

Automatic dishwashing articles comprise one or more fibrous structures of the present disclosure and a surfactant system, and optionally one or more optional ingredients known in the art of cleaning, for example useful in cleaning dishware in an automatic dishwashing machine. Examples of these optional ingredients include: anti-scalants, chelants, bleaching agents, perfumes, dyes, antibacterial agents, enzymes (e.g., protease, amylase), cleaning polymers (e.g., alkoxylated polyethyleneimine polymer), anti-redeposition polymers, hydrotropes, suds inhibitors, carboxylic acids, thickening agents, preservatives, disinfecting agents, glass and metal care agents, pH buffering means so that the automatic dishwashing liquor generally has a pH of from 3 to 14 (alternatively 8 to 11), or mixtures thereof. Examples of automatic dishwashing actives are described in U.S. Pat. Nos. 5,679,630; 5,703,034; 5,703,034; 5,705,464; 5,962,386; 5,968,881; 6,017,871; 6,020,294.

Scale formation can be a problem. It can result from precipitation of alkali earth metal carbonates, phosphates, and silicates. Examples of anti-scalants include polyacrylates and polymers based on acrylic acid combined with other moieties. Sulfonated varieties of these polymers are particular effective in nil phosphate formulation executions. Examples of anti-scalants include those described in U.S. Pat. No. 5,783,540, col. 15, 1. 20-col. 16, 1. 2; and EP 0 851 022 A2, pg. 12, 1. 1-20.

In one example, an automatic dishwashing article comprising a fibrous structure of the present disclosure may contain a dispersant polymer typically in the range from 0 to about 30% and/or from about 0.5% to about 20% and/or from about 1% to about 10% by weight of the automatic dishwashing article. The dispersant polymer may be ethoxylated cationic diamines or ethoxylated cationic polyamines described in U.S. Pat. No. 4,659,802. Other suitable dispersant polymers include co-polymers synthesized from acrylic acid, maleic acid and methacrylic acid such as ACUSOL® 480N and ACUSOL 588® supplied by Rohm & Haas and an acrylic-maleic (ratio 80/20) phosphono end group dispersant copolymers sold under the tradename of Acusol 425N® available from Rohm &Haas. Polymers containing both carboxylate and sulphonate monomers, such as ALCOSPERSE® polymers (supplied by Alco) are also acceptable dispersant polymers. In one example an ALCOSPERSE® polymer sold under the trade name ALCOSPERSE® 725, is a co-polymer of Styrene and Acrylic Acid. ALCOSPERSE® 725 may also provide a metal corrosion inhibition benefit. Other dispersant polymers are low molecular weight modified polyacrylate copolymers including the low molecular weight copolymers of unsaturated aliphatic carboxylic acids disclosed in U.S. Pat. Nos. 4,530,766, and 5,084,535 and European Patent Application No. 66,915, published Dec. 15, 1982.

In one example, an automatic dishwashing article comprising a fibrous structure of the present disclosure may contain a nonionic surfactant, a sulfonated polymer, optionally a chelant, optionally a builder, and optionally a bleaching agent, and mixtures thereof. A method of cleaning dishware is provided comprising the step of dosing an automatic dishwashing article of the present disclosure into an automatic dishwashing machine.

Hand Dishwashing Articles

Hand dish washing articles comprise one or more fibrous structures of the present disclosure that contains a surfactant system, and optionally one or more optional ingredients known in the art of cleaning and hand care, for example useful in cleaning dishware by hand. Examples of these optional ingredients include: perfume, dyes, pearlescent agents, antibacterial agents, enzymes (e.g., protease), cleaning polymers (e.g., alkoxylated polyethyleneimine polymer), cationic polymers, hydrotropes, humectants, emollients, hand care agents, polymeric suds stabilizers, bleaching agent, diamines, carboxylic acids, thickening agents, preservatives, disinfecting agents, pH buffering means so that the dish washing liquor generally has a pH of from 3 to 14 and/or from 8 to 11, or mixtures thereof. Examples of hand dishwashing actives are described in U.S. Pat. Nos. 5,990,065; and 6,060,122.

In one example, the surfactant of the hand dishwashing article comprises an alkyl sulfate, an alkoxy sulfate, an alkyl sulfonate, an alkoxy sulfonate, an alkyl aryl sulfonate, an amine oxide, a betaine or a derivative of aliphatic or heterocyclic secondary and ternary amine, a quaternary ammonium surfactant, an amine, a singly or multiply alkoxylated alcohol, an alkyl polyglycoside, a fatty acid amide surfactant, a $C_8$-$C_{20}$ ammonia amide, a monoethanolamide, a diethanolamide, an isopropanolamide, a polyhydroxy fatty acid amide, or a mixture thereof.

A method of washing dishware is provided comprising the step of dosing a hand dishwashing article of the present disclosure in a sink or basin suitable for containing soiled dishware. The sink or basin may contain water and/or soiled dishware.

Hard Surface Cleaning Article

Hard surface cleaning articles comprise one or more fibrous structures of the present disclosure that contains one or more ingredients known in the art of cleaning, for example useful in cleaning hard surfaces, such as an acid constituent, for example an acid constituent that provides good limescale removal performance (e.g., formic acid, citric acid, sorbic acid, acetic acid, boric acid, maleic acid, adipic acid, lactic acid malic acid, malonic acid, glycolic acid, or mixtures thereof). Examples of ingredients that may be included an acidic hard surface cleaning article may include those described in U.S. Pat. No. 7,696,143. Alternatively the hard surface cleaning article comprises an alkalinity constituent (e.g., alkanolamine, carbonate, bicarbonate compound, or mixtures thereof). Examples of ingredients that may be included in an alkaline hard surface cleaning article may include those described in US 2010/0206328 A1. A method of cleaning a hard surface includes using or dosing a hard surface cleaning article in a method to clean a hard surface. In one example, the method comprises dosing a hard surface cleaning article in a bucket or similar container, optionally adding water to the bucket before or after dosing the article to the bucket. In another example, the method comprising dosing a hard surface cleaning article in a toilet bowl, optionally scrubbing the surface of the toilet bowl after the article has dissolved in the water contained in the toilet bowl.

Toilet Bowl Cleaning Head

A toilet bowl cleaning head for a toilet bowl cleaning implement comprising one or more fibrous structures of the present disclosure is provided. The toilet bowl cleaning head may be disposable. The toilet bowl cleaning head may be removably attached to a handle, so that the user's hands remain remote from the toilet bowl. In one example, the toilet bowl cleaning head may contain a water dispersible shell. In turn, the water dispersible shell may comprise one or more fibrous structures of the present disclosure. This water dispersible shell may encase a core. The core may comprise at least one granular material. The granular material of the core may comprise surfactants, organic acids, perfumes, disinfectants, bleaches, detergents, enzymes, particulates, or mixtures thereof. Optionally, the core may be free from cellulose, and may comprise one or more fibrous structures of the present disclosure. Examples a suitable toilet bowl cleaning head may be made according to commonly assigned U.S. patent application Ser. No. 12/901,804. A suitable toilet bowl cleaning head containing starch materials may be made according to commonly assigned U.S. patent application Ser. Nos. 13/073,308, 13/073,274, and/or 13/073,346. A method of cleaning a toilet bowl surface is provided comprising the step of contacting the toilet bowl surface with a toilet bowl cleaning head of the present disclosure.

Methods of Use

The fibrous structures of the present disclosure comprising one or more fabric care active agents according the present disclosure may be utilized in a method for treating a fabric article. The method of treating a fabric article may comprise one or more steps selected from the group consisting of: (a) pre-treating the fabric article before washing the fabric article; (b) contacting the fabric article with a wash liquor formed by contacting the fibrous structure with water; (c) contacting the fabric article with the fibrous structure in a dryer; (d) drying the fabric article in the presence of the fibrous structure in a dryer; and (e) combinations thereof.

In some examples, the method may further comprise the step of pre-moistening the fibrous structure prior to contacting it to the fabric article to be pre-treated. For example, the fibrous structure can be pre-moistened with water and then adhered to a portion of the fabric comprising a stain that is to be pre-treated. Alternatively, the fabric may be moistened and the fibrous structure placed on or adhered thereto. In some examples, the method may further comprise the step of selecting of only a portion of the fibrous structure for use in treating a fabric article. For example, if only one fabric care article is to be treated, a portion of the fibrous structure may be cut and/or torn away and either placed on or adhered to the fabric or placed into water to form a relatively small amount of wash liquor which is then used to pre-treat the fabric. In this way, the user may customize the fabric treatment method according to the task at hand. In some examples, at least a portion of a fibrous structure may be applied to the fabric to be treated using a device. Exemplary devices include, but are not limited to, brushes, sponges and tapes. In yet another example, the fibrous structure may be applied directly to the surface of the fabric. Any one or more of the aforementioned steps may be repeated to achieve the desired fabric treatment benefit.

Test Methods

Unless otherwise specified, all tests described herein including those described under the Definitions section and the following test methods are conducted on samples that have been conditioned in a conditioned room at a temperature of 23° C.±1.0° C. and a relative humidity of 50%±2% for a minimum of 2 hours prior to the test. The samples tested are "usable units." "Usable units" as used herein means sheets, flats from roll stock, pre-converted flats, and/or single or multi-ply products. All tests are conducted under the same environmental conditions and in such conditioned room. Do not test samples that have defects such as wrinkles, tears, holes, and like. Samples conditioned as described herein are considered dry samples (such as "dry filaments") for testing purposes. All instruments are calibrated according to manufacturer's specifications.

Basis Weight Test Method

Basis weight of a fibrous structure is measured on stacks of twelve usable units using a top loading analytical balance with a resolution of ±0.001 g. The balance is protected from air drafts and other disturbances using a draft shield. A precision cutting die, measuring 3.500 in ±0.0035 in by 3.500 in ±0.0035 in is used to prepare all samples.

With a precision cutting die, cut the samples into squares. Combine the cut squares to form a stack twelve samples thick. Measure the mass of the sample stack and record the result to the nearest 0.001 g.

The Basis Weight is calculated in lbs/3000 ft² or g/m² as follows:

Basis Weight=(Mass of stack)/[(Area of 1square in stack)×(No. of squares in stack)]

For example,

Basis Weight(lbs/3000 ft²)=[[Mass of stack (g)/453.6 (g/lbs)]/[12.25 (in²)/144 (in²/ft²)×12]]×3000 or,

Basis Weight (g/m²)=Mass of stack (g)/[79.032 (cm²)/10,000 (cm²/m²)×12]

Report result to the nearest 0.1 lbs/3000 ft² or 0.1 g/m². Sample dimensions can be changed or varied using a similar precision cutter as mentioned above, so as at least 100 square inches of sample area in stack.

Water Content Test Method

The water (moisture) content present in a fibrous element and/or particle and/or fibrous structure is measured using the following Water Content Test Method. A fibrous element and/or particle and/or fibrous structure or portion thereof ("sample") in the form of a pre-cut sheet is placed in a conditioned room at a temperature of 23° C.±1.0° C. and a relative humidity of 50%±2% for at least 24 hours prior to testing. Each fibrous structure sample has an area of at least 4 square inches, but small enough in size to fit appropriately on the balance weighing plate. Under the temperature and humidity conditions mentioned above, using a balance with at least four decimal places, the weight of the sample is recorded every five minutes until a change of less than 0.5% of previous weight is detected during a 10 minute period. The final weight is recorded as the "equilibrium weight". Within 10 minutes, the samples are placed into the forced air oven on top of foil for 24 hours at 70° C.±2° C. at a relative humidity of 4%±2% for drying. After the 24 hours of drying, the sample is removed and weighed within 15 seconds. This weight is designated as the "dry weight" of the sample.

The water (moisture) content of the sample is calculated as follows:

$$\% \text{ Water in sample} = 100\% \times \frac{(\text{Equilibrium weight of sample} - \text{Dry weight of sample})}{\text{Dry weight of sample}}$$

The % Water (moisture) in sample for 3 replicates is averaged to give the reported % Water (moisture) in sample. Report results to the nearest 0.1%.

Dissolution Test Method

Apparatus and Materials (also, see FIGS. 18 though 20):

600 mL Beaker 54

Magnetic Stirrer 56 (Labline Model No. 1250 or equivalent)

Magnetic Stirring Rod 58 (5 cm)

Thermometer (1 to 100° C. +/−1° C.)

Cutting Die—Stainless Steel cutting die with dimensions 3.8 cm×3.2 cm

Timer (0-3,600 seconds or 1 hour), accurate to the nearest second. Timer used should have sufficient total time measurement range if sample exhibits dissolution time greater than 3,600 seconds. However, timer needs to be accurate to the nearest second.

Polaroid 35 mm Slide Mount 60 (commercially available from Polaroid Corporation or equivalent) -)

35 mm Slide Mount Holder 62 (or equivalent)

City of Cincinnati Water or equivalent having the following properties: Total Hardness=155 mg/L as $CaCO_3$; Calcium content=33.2 mg/L; Magnesium content=17.5 mg/L; Phosphate content=0.0462.

Test Protocol

Equilibrate samples in constant temperature and humidity environment of 23° C.±1.0° C. and 50% RH±2% for at least 2 hours. Measure the basis weight of the fibrous structure sample to be measured using Basis Weight Test Method defined herein. Cut three dissolution test specimens from the article, for example fibrous structure sample using cutting die (3.8 cm×3.2 cm), so it fits within the 35 mm Slide Mount 60, which has an open area dimensions 24×36 mm Lock each specimen in a separate 35 mm slide mount 60. Place magnetic stirring rod 58 into the 600 mL beaker 54. Turn on the city water tap flow (or equivalent) and measure water temperature with thermometer and, if necessary, adjust the hot or cold water to maintain it at the testing temperature. Testing temperature is 15° C.±1° C. water. Once at testing temperature, fill beaker 54 with 500 mL±5 mL of the 15° C.±1° C. city water. Place full beaker 54 on magnetic stirrer 56, turn on stirrer 56, and adjust stir speed until a vortex develops and the bottom of the vortex is at the 400 mL mark on the beaker 54. Secure the 35 mm slide mount 60 in the alligator clamp 64 of the 35 mm slide mount holder 62 such that the long end 66 of the slide mount 60 is parallel to the water surface. The alligator clamp 64 should be positioned in the middle of the long end 66 of the slide mount 60. The depth adjuster 68 of the holder 62 should be set so that the distance between the bottom of the depth adjuster 68 and the bottom of the alligator clip 64 is ~11+/−0.125 inches. This set up will position the sample surface perpendicular to the flow of the water. In one motion, drop the secured slide and clamp into the water and start the timer. The sample is dropped so that the sample is centered in the beaker. Disintegration occurs when the nonwoven structure breaks apart. Record this as the disintegration time. When all of the visible nonwoven structure is released from the slide mount, raise the slide out of the water while continuing the monitor the solution for undissolved nonwoven structure fragments. Dissolution occurs when all nonwoven structure fragments are no longer visible. Record this as the dissolution time.

Three replicates of each sample are run and the average disintegration and dissolution times are recorded. Average disintegration and dissolution times are in units of seconds.

The average disintegration and dissolution times can be normalized for basis weight by dividing each by the sample basis weight as determined by the Basis Weight Method defined herein. Basis weight normalized disintegration and dissolution times are in units of seconds/gsm of sample ($s/(g/m^2)$).

Median Particle Size Test Method

This test method must be used to determine median particle size.

The median particle size test is conducted to determine the median particle size of the seed material using ASTM D 502-89, "Standard Test Method for Particle Size of Soaps and Other Detergents", approved May 26, 1989, with a further specification for sieve sizes used in the analysis. Following section 7, "Procedure using machine-sieving method," a nest of clean dry sieves containing U.S. Standard (ASTM E 11) sieves #8 (2360 um), #12 (1700 um), #16 (1180 um), #20 (850 um), #30 (600 um), #40 (425 um), #50 (300 um), #70 (212 um), #100 (150 um) is required. The prescribed Machine-Sieving Method is used with the above sieve nest. The seed material is used as the sample. A suitable sieve-shaking machine can be obtained from W. S. Tyler Company of Mentor, Ohio, U.S.A.

The data are plotted on a semi-log plot with the micron size opening of each sieve plotted against the logarithmic abscissa and the cumulative mass percent ($Q_3$) plotted against the linear ordinate. An example of the above data representation is given in ISO 9276-1:1998, "Representation of results of particle size analysis—Part 1: Graphical Representation", Figure A.4. The seed material median particle size ($D_{50}$), for the purpose of the present disclosure, is defined as the abscissa value at the point where the cumulative mass percent is equal to 50 percent, and is calculated by a straight line interpolation between the data points directly above (a50) and below (b50) the 50% value using the following equation:

$$D50=10^{\wedge}[\text{Log}(D_{a50})-(\text{Log}(D_{a50})-\text{Log}(D_{b50}))*(Q_{a50}-50\%)/(Q_{a50}-Q_{b50})]$$

where $Q_{a50}$ and $Q_{b50}$ are the cumulative mass percentile values of the data immediately above and below the 50th percentile, respectively; and $D_{a50}$ and $D_{b50}$ are the micron sieve size values corresponding to these data.

In the event that the 50th percentile value falls below the finest sieve size (150 um) or above the coarsest sieve size (2360 um), then additional sieves must be added to the nest following a geometric progression of not greater than 1.5, until the median falls between two measured sieve sizes.

The Distribution Span of the Seed Material is a measure of the breadth of the seed size distribution about the median. It is calculated according to the following:

$$\text{Span}=(D_{84}/D_{50}+D_{50}/D_{16})/2$$

Where $D_{50}$ is the median particle size and $D_{84}$ and $D_{16}$ are the particle sizes at the sixteenth and eighty-fourth percentiles on the cumulative mass percent retained plot, respectively.

In the event that the D16 value falls below the finest sieve size (150 um), then the span is calculated according to the following:

$$\text{Span}=(D_{84}/D_{50})$$

In the event that the D84 value falls above the coarsest sieve size (2360 um), then the span is calculated according to the following:

$$\text{Span}=(D_{50}/D_{16}).$$

In the event that the D16 value falls below the finest sieve size (150 um) and the D84 value falls above the coarsest sieve size (2360 um), then the distribution span is taken to be a maximum value of 5.7.

Diameter Test Method

The diameter of a discrete fibrous element or a fibrous element within a fibrous structure is determined by using a Scanning Electron Microscope (SEM) or an Optical Microscope and an image analysis software. A magnification of 200 to 10,000 times is chosen such that the fibrous elements are suitably enlarged for measurement. When using the SEM, the samples are sputtered with gold or a palladium compound to avoid electric charging and vibrations of the fibrous element in the electron beam. A manual procedure for determining the fibrous element diameters is used from the image (on monitor screen) taken with the SEM or the optical microscope. Using a mouse and a cursor tool, the edge of a randomly selected fibrous element is sought and then measured across its width (i.e., perpendicular to fibrous element direction at that point) to the other edge of the fibrous element. A scaled and calibrated image analysis tool provides the scaling to get actual reading in μm. For fibrous elements within a fibrous structure, several fibrous element are randomly selected across the sample of the fibrous structure using the SEM or the optical microscope. At least two portions of the fibrous structure are cut and tested in this manner Altogether at least 100 such measurements are made and then all data are recorded for statistical analysis. The recorded data are used to calculate average (mean) of the fibrous element diameters, standard deviation of the fibrous element diameters, and median of the fibrous element diameters.

Another useful statistic is the calculation of the amount of the population of fibrous elements that is below a certain upper limit. To determine this statistic, the software is programmed to count how many results of the fibrous element diameters are below an upper limit and that count (divided by total number of data and multiplied by 100%) is reported in percent as percent below the upper limit, such as percent below 1 micrometer diameter or %-submicron, for example. We denote the measured diameter (in μm) of an individual circular fibrous element as di.

In the case that the fibrous elements have non-circular cross-sections, the measurement of the fibrous element diameter is determined as and set equal to the hydraulic diameter which is four times the cross-sectional area of the fibrous element divided by the perimeter of the cross-section of the fibrous element (outer perimeter in case of hollow fibrous elements). The number-average diameter, alternatively average diameter is calculated as:

$$d_{num} = \frac{\sum_{i=1}^{n} d_i}{n}$$

Tensile Test Method: Elongation, Tensile Strength, TEA and Modulus

Elongation, Tensile Strength, TEA and Tangent Modulus are measured on a constant rate of extension tensile tester with computer interface (a suitable instrument is the EJA Vantage from the Thwing-Albert Instrument Co. Wet Berlin, NJ) using a load cell for which the forces measured are within 10% to 90% of the limit of the cell. Both the movable (upper) and stationary (lower) pneumatic jaws are fitted with smooth stainless steel faced grips, 25.4 mm in height and wider than the width of the test specimen. An air pressure of about 60 psi is supplied to the jaws.

Eight usable units of a fibrous structure are divided into two stacks of four samples each. The samples in each stack are consistently oriented with respect to machine direction (MD) and cross direction (CD). One of the stacks is designated for testing in the MD and the other for CD. Using a one inch precision cutter (Thwing Albert JDC-1-10, or similar) cut 4 MD strips from one stack, and 4 CD strips from the other, with dimensions of 1.00 in ±0.01 in wide by 3.0-4.0 in long. Each strip of one usable unit thick will be treated as a unitary specimen for testing.

Program the tensile tester to perform an extension test, collecting force and extension data at an acquisition rate of 20 Hz as the crosshead raises at a rate of 2.00 in/min (5.08 cm/min) until the specimen breaks. The break sensitivity is set to 80%, i.e., the test is terminated when the measured force drops to 20% of the maximum peak force, after which the crosshead is returned to its original position.

Set the gauge length to 1.00 inch. Zero the crosshead and load cell. Insert at least 1.0 in of the unitary specimen into the upper grip, aligning it vertically within the upper and lower jaws and close the upper grips. Insert the unitary specimen into the lower grips and close. The unitary specimen should be under enough tension to eliminate any slack, but less than 5.0 g of force on the load cell. Start the tensile tester and data collection. Repeat testing in like fashion for all four CD and four MD unitary specimens. Program the software to calculate the following from the constructed force (g) verses extension (in) curve:

Tensile Strength is the maximum peak force (g) divided by the sample width (in) and reported as g/M to the nearest 1 g/M.

Adjusted Gauge Length is calculated as the extension measured at 3.0 g of force (in) added to the original gauge length (in).

Elongation is calculated as the extension at maximum peak force (in) divided by the Adjusted Gauge Length (in) multiplied by 100 and reported as % to the nearest 0.1%.

Total Energy (TEA) is calculated as the area under the force curve integrated from zero extension to the extension at the maximum peak force (g*in), divided by the product of the adjusted Gauge Length (in) and specimen width (in) and is reported out to the nearest 1 g*in/in².

Replot the force (g) verses extension (in) curve as a force (g) verses strain curve. Strain is herein defined as the extension (in) divided by the Adjusted Gauge Length (in).

Program the software to calculate the following from the constructed force (g) verses strain curve: Tangent Modulus is calculated as the slope of the linear line drawn between the two data points on the force (g) versus strain curve, where one of the data points used is the first data point recorded after 28 g force, and the other data point used is the first data point recorded after 48 g force. This slope is then divided by the specimen width (2.54 cm) and reported to the nearest 1 g/cm.

The Tensile Strength (g/in), Elongation (%), Total Energy (g*in/in²) and Tangent Modulus (g/cm) are calculated for the four CD unitary specimens and the four MD unitary specimens. Calculate an average for each parameter separately for the CD and MD specimens.

Calculations

Geometric Mean Tensile=Square Root of [*MD* Tensile Strength (g/in)×*CD* Tensile Strength (g/in)]

Geometric Mean Peak Elongation=Square Root of [*MD* Elongation (%)×*CD* Elongation (%)]

Geometric Mean TEA=Square Root of [*MD* TEA (g*in/in²)×*CD* TEA (g/in²)]

Geometric Mean Modulus=Square Root of [*MD* Modulus (g/cm)×*CD* Modulus (g/cm)]

Total Dry Tensile Strength(*TDT*)=*MD* Tensile Strength (g/in)+*CD* Tensile Strength (g/in)

Total TEA=*MD* TEA (g*in/in²)+*CD* TEA (g*in/in²)

Total Modulus=*MD* Modulus (g/cm)+*CD* Modulus (g/cm)

Tensile Ratio=*MD* Tensile Strength (g/in)/*CD* Tensile Strength (g/in)

Thickness Test Method

The thickness of a fibrous structure and/or article height is measured using a ProGage Thickness Tester (Thwing-Albert Instrument Company, West Berlin, NJ) with a circular pressure foot diameter of 2.00 inches (area of 3.14 in²) at a pressure of 15.5 g/cm². Five (5) samples are prepared by cutting samples of a fibrous structure such that each cut sample is larger in size than the pressure foot surface, avoiding creases, folds, and obvious defects. If an article has a length or width less than the diameter of the pressure foot a smaller diameter pressure foot may be used, while making the appropriate adjustments so that a pressure of 15.5 g/cm² is still applied. An individual sample is placed on the anvil with the sample centered underneath the pressure foot, or centered on the location of the maximum height of an article. The foot is lowered at 0.03 in/sec to an applied pressure of 15.5 g/cm². The reading is taken after 3 sec dwell time, and the foot is raised. The measure is repeated in like fashion for the remaining 4 samples. The thickness or article height is calculated as the average thickness of the five samples and is reported to the nearest 0.01 mm Shear Viscosity Test Method The shear viscosity of a filament-forming composition of the present disclosure is measured using a capillary rheometer, Goettfert Rheograph 6000, manufactured by Goettfert USA of Rock Hill SC, USA. The measurements are conducted using a capillary die having a diameter D of 1.0 mm and a length L of 30 mm (i.e., L/D=30). The die is attached to the lower end of the rheometer's 20 mm barrel, which is held at a die test temperature of 75° C. A preheated to die test temperature, 60 g sample of the filament-forming composition is loaded into the barrel section of the rheometer. Rid the sample of any entrapped air. Push the sample from the barrel through the capillary die at a set of chosen rates 1,000-10,000 seconds$^{-1}$. An apparent shear viscosity can be calculated with the rheometer's software from the pressure drop the sample experiences as it goes from the barrel through the capillary die and the flow rate of the sample through the capillary die. The log (apparent shear viscosity) can be plotted against log (shear rate) and the plot can be fitted by the power law, according to the formula $\eta=K\gamma^{n-1}$, wherein K is the material's viscosity constant, n is the material's thinning index and $\gamma$ is the shear rate. The reported apparent shear viscosity of the filament-forming composition herein is calculated from an interpolation to a shear rate of 3,000 sec$^{-1}$ using the power law relation.

Weight Average Molecular Weight

The weight average molecular weight (Mw) of a material, such as a polymer, is determined by Gel Permeation Chromatography (GPC) using a mixed bed column. A high performance liquid chromatograph (HPLC) having the following components: Millenium®, Model 600E pump, system controller and controller software Version 3.2, Model 717 Plus autosampler and CHM-009246 column heater, all manufactured by Waters Corporation of Milford, MA, USA, is utilized. The column is a PL gel 20 μm Mixed A column (gel molecular weight ranges from 1,000 g/mol to 40,000,000 g/mol) having a length of 600 mm and an internal diameter of 7.5 mm and the guard column is a PL gel 20 μm, 50 mm length, 7.5 mm ID. The column temperature is 55° C. and the injection volume is 200 μL. The detector is a DAWN® Enhanced Optical System (EOS) including Astra® software, Version 4.73.04 detector software, manufactured by Wyatt Technology of Santa Barbara, CA, USA, laser-light scattering detector with K5 cell and 690 nm laser. Gain on odd numbered detectors set at 101. Gain on even numbered detectors set to 20.9. Wyatt Technology's Optilab® differential refractometer set at 50° C. Gain set at 10. The mobile phase is HPLC grade dimethylsulfoxide with 0.1% w/v LiBr and the mobile phase flow rate is 1 mL/min, isocratic. The run time is 30 minutes.

A sample is prepared by dissolving the material in the mobile phase at nominally 3 mg of material/1 mL of mobile phase. The sample is capped and then stirred for about 5 minutes using a magnetic stirrer. The sample is then placed in an 85° C. convection oven for 60 minutes. The sample is then allowed to cool undisturbed to room temperature. The sample is then filtered through a 5 μm Nylon membrane, type Spartan-25, manufactured by Schleicher & Schuell, of Keene, NH, USA, into a 5 milliliter (mL) autosampler vial using a 5 mL syringe.

For each series of samples measured (3 or more samples of a material), a blank sample of solvent is injected onto the column. Then a check sample is prepared in a manner similar to that related to the samples described above. The check sample comprises 2 mg/mL of pullulan (Polymer Laboratories) having a weight average molecular weight of 47,300 g/mol. The check sample is analyzed prior to analyzing each set of samples. Tests on the blank sample, check sample, and material test samples are run in duplicate. The final run is a run of the blank sample. The light scattering detector and differential refractometer is run in accordance with the "Dawn EOS Light Scattering Instrument Hardware Manual" and "Optilab® DSP Interferometric Refractometer Hardware Manual," both manufactured by Wyatt Technology Corp., of Santa Barbara, CA, USA, and both incorporated herein by reference.

The weight average molecular weight of the sample is calculated using the detector software. A dn/dc (differential change of refractive index with concentration) value of 0.066 is used. The baselines for laser light detectors and the refractive index detector are corrected to remove the contributions from the detector dark current and solvent scattering. If a laser light detector signal is saturated or shows excessive noise, it is not used in the calculation of the molecular mass. The regions for the molecular weight characterization are selected such that both the signals for the 90° detector for the laser-light scattering and refractive index are greater than 3 times their respective baseline noise levels. Typically the high molecular weight side of the chromatogram is limited by the refractive index signal and the low molecular weight side is limited by the laser light signal.

The weight average molecular weight can be calculated using a "first order Zimm plot" as defined in the detector software. If the weight average molecular weight of the sample is greater than 1,000,000 g/mol, both the first and second order Zimm plots are calculated, and the result with the least error from a regression fit is used to calculate the molecular mass. The reported weight average molecular weight is the average of the two runs of the material test sample.

Fibrous Element Composition Test Method

In order to prepare fibrous elements for fibrous element composition measurement, the fibrous elements must be conditioned by removing any coating compositions and/or materials present on the external surfaces of the fibrous elements that are removable. An example of a method for doing so is washing the fibrous elements 3 times with a suitable solvent that will remove the external coating while leaving the fibrous elements unaltered. The fibrous elements are then air dried at 23° C.±1.0° C. until the fibrous elements comprise less than 10% moisture. A chemical analysis of the conditioned fibrous elements is then completed to determine the compositional make-up of the fibrous elements with respect to the filament-forming materials and the active agents and the level of the filament-forming materials and active agents present in the fibrous elements.

The compositional make-up of the fibrous elements with respect to the filament-forming material and the active agents can also be determined by completing a cross-section analysis using TOF-SIMs or SEM. Still another method for determining compositional make-up of the fibrous elements uses a fluorescent dye as a marker. In addition, as always, a manufacturer of fibrous elements should know the compositions of their fibrous elements.

Inter-Ply, Intra-Ply, and Whole 180° Peel Test Method

The Inter-Ply, Intra-Ply, and Whole 180° Peel of a sample of a fibrous structure to be tested is measured on a constant rate of extension tensile tester (a suitable instrument is the MTS Alliance using Testworks 4.0 Software, as available from MTS Systems Corp., Eden Prairie, MN) using a load cell for which the forces measured are within 10% to 90% of the limit of the cell. Both the movable (upper) and stationary (lower) pneumatic jaws are fitted with rubber faced grips, wider than the width of a testing strip (described below) of the sample. All testing is performed in a room controlled at 23° C.±3° C. and 50%±2% relative humidity.

Figure 21A:
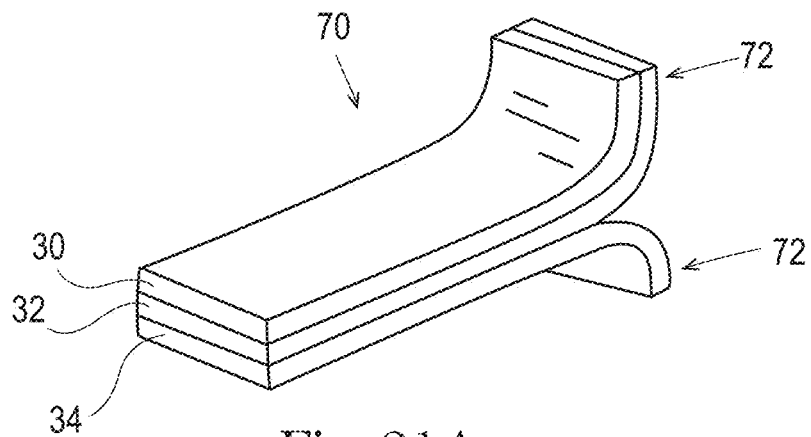
FIG. 21A is a schematic representation of preparing a fibrous structure for measuring Inter-ply Peel properties of the fibrous structure according to the Inter-ply, Intra-ply, Whole 180° Test Method described herein.
Figure 21B:
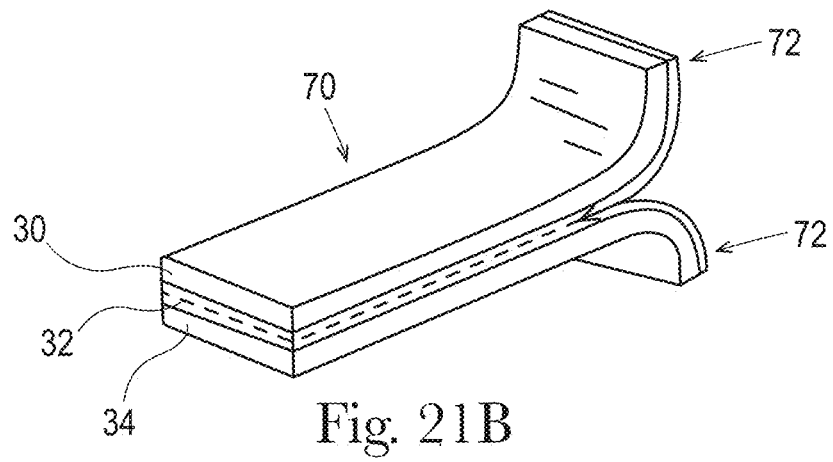
FIG. 21B is a schematic representation of preparing a fibrous structure for measuring Intra-ply Peel properties of the fibrous structure according to the Inter-ply, Intra-ply, Whole 180° Test Method described herein.
Figure 21C:
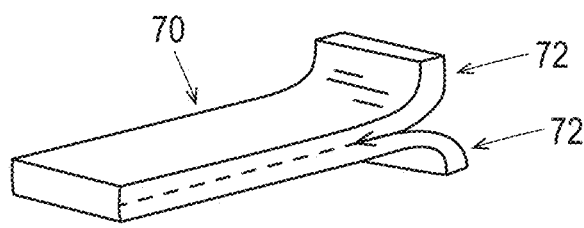
FIG. 21C is a schematic representation of preparing a fibrous structure for measuring Whole 180° Peel properties of the fibrous structure according to the Inter-ply, Intra-ply, Whole 180° Test Method described herein.

As shown in FIGS. 21A-21C, samples of a fibrous structure to be tested are conditioned at about 23° C.±2° C. and about 50° C.±2% ° C. relative humidity for at least two hours before testing. The samples are prepared by cutting a testing strip sample 70 of a fibrous structure, 25.4 mm±0.5 mm wide centered along the longitudinal axis of the sample, using a cutting die, razor knife or other appropriate means. If both lateral edges are not rectilinear, select one of the curved ends and make a lateral cut perpendicular to the longitudinal axis, such that the end is a full 25.4 mm wide. Identify the cut end as the back end. If both ends are rectilinear, choose either end and identify as the back end.

For samples where individual plies can be identified and separated as shown in FIGS. 21A and 21B, both inter-ply and intra-ply peels are conducted.
1) To prepare an inter-ply peel testing strip sample 70 as shown in FIG. 21A (as described above), select the end opposite the back end and identify the interface where two or more plies 30, 32, and 34 are bonded together. Manually initiate a peel between the two plies (in this case at the interface between plies 32 and 34) that extends longitudinally 10 mm into the testing strip sample 70 to create two leads 72 to grip the testing strip sample 70 for testing. A total of five Inter-Ply testing strip samples 70 are prepared for testing.
2) To prepare an intra-ply peel testing strip sample 70 as shown in FIG. 21B (as described above), identify two adjacent ply interfaces (interfaces between plies 30 and 32 and between plies 32 and 34) and manually initiate the peel midway between the identified ply interfaces that extends longitudinally in the direction of the arrow 10 mm into the testing strip sample 70 to create two leads 72 to grip the testing strip sample 70 for testing. A total of five Intra-Ply testing strip samples 70 are prepared for testing.

For samples where individual plies cannot be identified and separated as shown in FIG. 21C, a single peel (whole 180° peel) is conducted without regard to plies. To prepare a whole 180° peel testing strip sample 70 as shown in FIG. 21C (as described above), select the end opposite the back end. Manually initiate a peel at the middle of the z-direction of the testing strip sample 70 that extends longitudinally in the direction of the arrow 10 mm into the testing strip sample 70 to create two leads 72 to grip the testing strip sample 70 for testing. A total of five whole 180° peel testing strip samples 70 are prepared for testing.

Program the tensile tester for an extension test collecting force (N) and extension (mm) data at 200 Hz as the crosshead is raised at 5.0 mm/s until the testing strip sample is completely separated into two layers.

Set the gage length to 10 mm Zero the crosshead and load cell. Insert one of the testing strip sample leads in the upper grip and close. Insert the other testing strip sample lead into the lower grips and close. The sample should be under enough tension to eliminate any slack, but less than 0.05 N of force on the load cell. Start the test and acquire data. Repeat in like fashion for all five Inter-ply peel testing strip samples and all five intra-ply peel testing strip samples, or all five whole 180° peel testing strip samples.

Construct a force (N) versus extension (mm) curve. Record the Peak Peel Force (N) to the nearest 0.01 N. Calculate the average peel force (N) from the force (N) versus extension (mm) curve starting 10 mm from the start of the peel and ending 10 mm from the point the two layers separate. Record the Average Peel Force (N) to the nearest 0.01 N.

For testing strip samples that the plies can be identified and selected, calculate the arithmetic mean for Peak Peel Force (N) and Average Peel Force (N) separately for the inter-ply peel and intra-ply peel testing strip samples and report the averages. The arithmetic means for Peak Peel Force (N), namely the Average Inter-Ply Peak Peel Force and Average Intra-Ply Peak Peel Forceare reported to the nearest 0.01 N. For this case the lowest value of either the Average Inter-Ply Peak Peel Force or Average Intra-Ply Peak Peel Force is assigned as the Average Whole 180° Peak Peel Force and reported to the nearest 0.01 N. The arithmetic mean of the Average Peel Force (N) namely, the Average Inter-Ply Average Peel Force and Average Intra-Ply Average Peel Force, are reported to the nearest 0.01 N. For this case, the lowest value of either the Average Inter-Ply Average Peel Force or Average Intra-Ply Average Peel Force is assigned as the Average Whole 180° Average Peel Force and reported to the nearest 0.01 N.

For testing strip samples that the plies cannot be identified and selected, calculate the arithmetic mean for Peak Peel Force (N) and Average Peel Force (N) separately for intra-ply peel testing strip samples and report the Average Intra-Ply Peak Peel Force and the Average Intra-Ply Average Peel Force to the nearest 0.01 N. For this case, the Average Intra-Ply Peak Peel Force is assigned as the Average Whole 180° Peak Peel Force and reported to the nearest 0.01 N. Also, for this case, the Average Intra-Ply Average Peel Force is assigned as the Average Whole 180° Average Peel Force and reported to the nearest 0.01 N Lap Shear Test Method The Lap Shear of a sample of fibrous structure to be tested is measured on a constant rate of extension tensile tester (a suitable instrument is the MTS Alliance using Testworks 4.0 Software, as available from MTS Systems Corp., Eden Prairie, MN) using a load cell for which the forces measured are within 10% to 90% of the limit of the cell. Both the movable (upper) and stationary (lower) pneumatic jaws are fitted with rubber faced grips, wider than the width of the testing strip (described below) of the sample. All testing is performed in a room controlled at 23° C.±3° C. and 50%±2% relative humidity.

Figure 22:
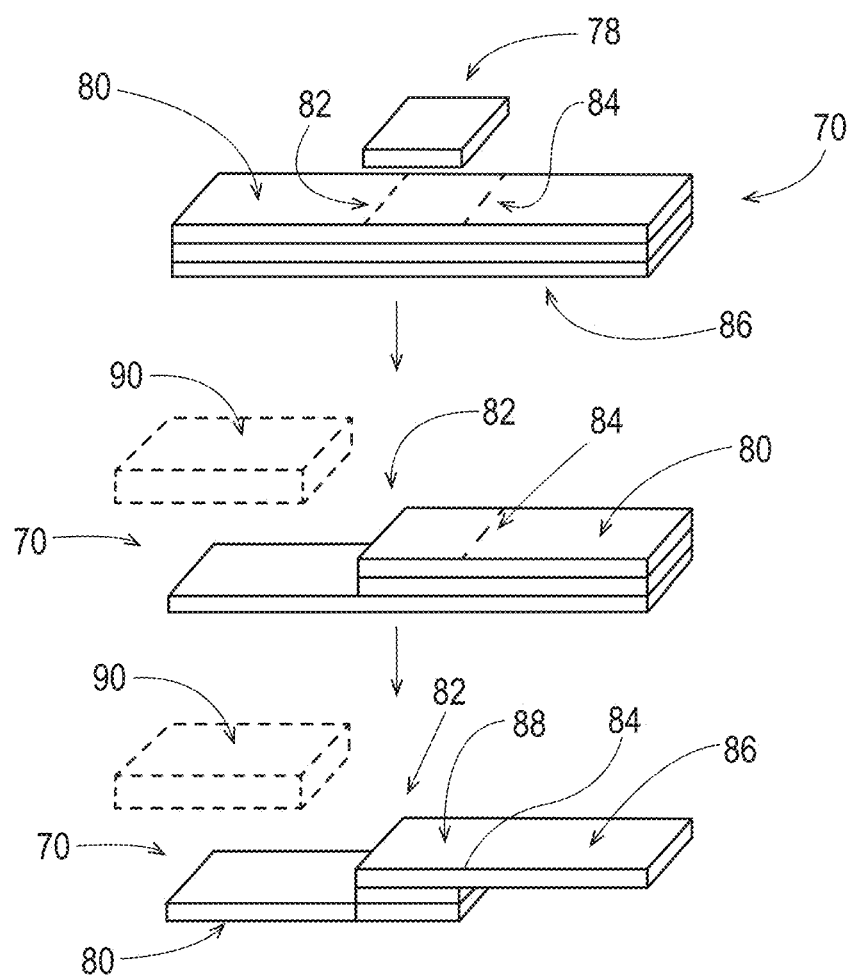
FIG. 22 is a schematic flow chart representing the preparation of a fibrous structure for measuring Lap Shear properties of the fibrous structure according to the Lap Shear Test Method described herein.

As shown in FIG. 22, samples of a fibrous structure to be tested are conditioned at about 23° C.±2° C. and about 50° C.±2° C. % relative humidity for at least two hours before testing. The samples are prepared by cutting a testing strip sample 70, 25.4 mm±0.5 mm wide centered along the longitudinal axis of the sample, using a cutting die, razor knife or other appropriate means. Place the testing strip sample 70 on a flat horizontal surface (not shown). Place a 25 mm gage block 78 onto the top surface 80 of the testing strip sample 70 centered at the longitudinal and lateral centerline of the testing strip sample 70. Mark two lateral lines, 82 and 84 parallel to the sides of the testing strip sample 70 on either side the gage block 78. Turn the testing strip sample 70 over, and in like fashion mark the surface 86 of the other side of the testing strip sample 70. The region interior to these marks will be the lap region 88. Divide the testing strip sample 70 horizontally into thirds. From the left lateral edge identify the bottom one third of the testing strip sample 70. At the left surface mark, lateral line 82, carefully make a lateral cut through the z-direction of testing strip sample 70 from the surface down to the bottom one third of the testing strip sample 70. Remove the cut plies 90 from the left mark to the distal edge of the testing strip sample 70. Flip the testing strip sample 70 over (side to side) so that surface 86 of the other side is facing upward. From the left lateral edge identify the bottom one third of the testing strip sample 70. At the left surface mark, carefully make a lateral cut through the z-direction of the testing strip sample 70 from the surface down to the bottom one third of the testing strip sample 70. Remove the cut plies 90 (two thirds of thickness) from the left mark to the distal edge of the testing strip sample 70. The lap region 88 consists of the total thickness of the testing strip sample 70.

Program the tensile tester for an extension test collecting force (N) and extension (mm) data at 200 Hz as the crosshead is raised at 5.0 mm/s until the testing strip sample is completely separated into two layers. The crosshead is then returned to its initial position.

Set the gage length to 35 mm Zero the crosshead and load cell. Insert one end of the testing strip sample 70 into the upper grip such that there is 5 mm between the bottom of the grip and the lap region 88 and close. Insert the other end of the testing strip sample 70 into the lower grips and close. The testing strip sample 70 should be under enough tension to eliminate any slack, but less than 0.05 N of force on the load cell. Start the test and acquire data. Repeat in like fashion for five replicate testing strip samples 70, each from equivalent fibrous structure samples.

Construct a force (N) versus extension (mm) curve. Record the Lap Shear Peak Force (N) to the nearest 0.01 N. Calculate the energy (N*mm) as the area under the force (N) versus extension (mm) curve from the first 25 mm of the curve. Record the Lap Shear Average Energy (N*mm) to the nearest 0.01 N. Calculate the arithmetic mean for Lap Shear Peak Force and Lap Shear Average Energy and report the averages (Average Lap Shear Peak Force and Average Lap Shear Average Energy) to the nearest report to the nearest 0.01 N and 0.01 N*mm respectively.

Modified Circular Bend Test Method

The Modified Circular Bend of a sample of fibrous structure to be tested is measured on a constant rate of extension tensile tester (a suitable instrument is the MTS Alliance using Testworks 4.0 Software, as available from MTS Systems Corp., Eden Prairie, MN) using a load cell for which the forces measured are within 10% to 90% of the limit of the cell. All testing is performed in a room controlled at 23° C.±3° C. and 50%±2% relative humidity.

Figure 23B:
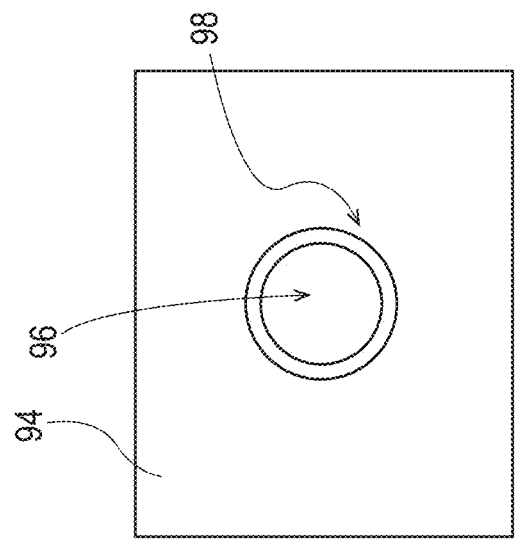
FIG. 23B is a schematic representation of a top view of a portion of FIG. 23A.
Figure 23A:
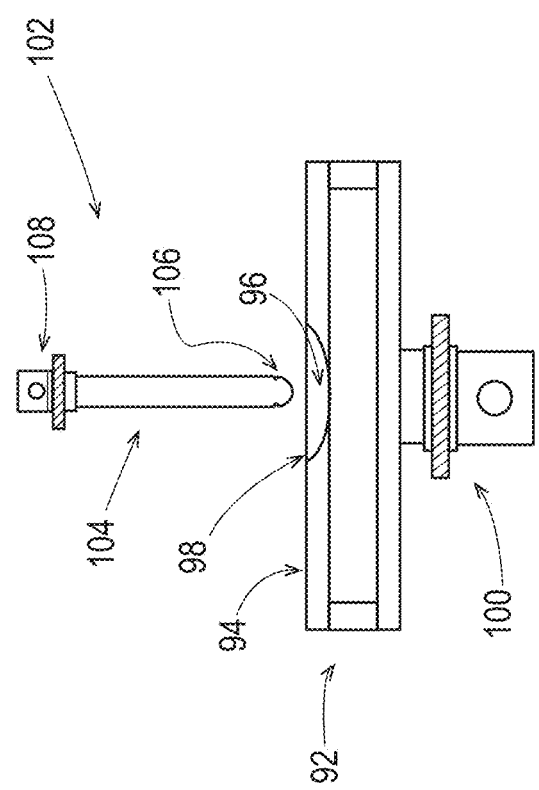
FIG. 23A is a schematic representation of an example of a setup of equipment used in measuring the Modified Circular Bend properties of a fibrous structure according to the Modified Circular Bend Test Method.

As shown in FIGS. 23A and 23B, a bottom stationary fixture 92 consists of a horizontal smooth-polished stainless steel platform 94 which is 102.0 mm wide by 102.0 mm long by 6.35 mm thick. The platform 94 has a 18.75 mm diameter orifice 96 at its center with a lap edge 98 of that orifice 96 having a 45 degree angle to a depth of 4.75 mm (i.e., the outer diameter of bevel is 28.25 mm). The bottom stationary fixture 92 is constructed such that it has at least 20 mm of clearance underneath the platform 94. The platform 94 has an adapter 100 compatible with the mount of the tensile tester capable of securing the platform 94 horizontally and orthogonal to the pull direction of the tensile tester. An upper fixture 102 consists of a cylindrical plunger 104 having an overall length of 70 mm with a diameter of 6.25 mm. The plunger 104 has a contact tip 106, which is a ball nose having a radius of 2.97 mm. The plunger 104 has an adapter 108 compatible with the mount on the load cell capable of securing the plunger 104 orthogonal to the platform 94. Once assembled, the plunger 94 is concentric with the orifice 96 with equal clearance on all sides.

Fibrous structure samples are conditioned at 23° C.±3° C. and 50%±2% relative humidity two hours prior to testing. Take 10 individual fibrous structure samples and divide into 2 stacks of five, maintaining top to bottom orientation. The first stack is tested with the top of the sample facing upward and the second stack is tested with the bottom of the sample facing upward.

Set the gage length to 25.0 mm from the bottom of the contact tip 106 of the plunger 104 to the bottom surface of the platform 94. Program the tensile tester as a compression test, to lower the crosshead at 50.0 cm per minute for 25.0 mm and record force (N) and displacement (mm) at a data rate of 100 Hz, and then return the crosshead to its original gage length.

Zero the crosshead and load cell. Position a sample centered underneath the plunger with its edges parallel and perpendicular with the edges of the platform 94. Begin the test and collect force (N) and displacement (mm) data.

Construct a graph of force (N) verses displacement (mm). Read the Maximum Peak Force (N) from the graph and record to the nearest 0.01 N. Calculate the Bending Stiffness as the greatest slope of the curve utilizing a line segment that is at least 20% of the Maximum Peak Force and record to the nearest 0.1 N/m.

Repeat in like fashion for all 10 samples and report the arithmetic mean for Average Maximum Peak Force (N) to the nearest 0.01 N and Average Bending Stiffness to the nearest 0.1 N/m.

Hand Dissolution Test Method

Materials Needed:

Articles to be tested: 5 articles will be tested so that an average of the number of strokes for each if the individual article samples is calculated and recorded as the Average Hand Dissolution value for the article. For this method, the entire consumer saleable or consumer use article is tested. If the entire consumer saleable or consumer use article has a length and/or width greater than 7 cm, then the article is cut such that each greater than 7 cm dimension is reduced to 4-5 cm.

Nitrile Gloves 10 cc syringe

Plastic Weigh boat (~3 in×3 in)

100 mL Glass beaker

Water (City of Cincinnati Water or equivalent having the following properties: Total Hardness=155 mg/L as $CaCO_2$; Calcium content=33.2 mg/L; Magnesium content=17.5 mg/L; Phosphate content=0.0462 mg/L)

Protocol:

Add 80 mL of water to glass beaker.

Heat water in beaker until water is at a temperature of 100° F.±3° F.

Transfer 10 mL of the 100° F.±3° F. water from the beaker into the weigh boat via the syringe.

Within 30 seconds of transferring the water to the weigh boat, place article sample in palm of gloved hand (hand in cupped position to hold article sample and hold water that insults the article sample).

Add water quickly from the weigh boat to the article sample and allow to immediately wet for a period of 5-10 seconds.

Rub with opposite hand (also gloved) in 2 rapid circular strokes.

Visually examine the article sample in hand after the 2 strokes. If article sample is completely dissolved, record number of strokes=2 Dissolution Strokes. If not completely dissolved, rub remaining article sample for 2 more circular strokes (4 total) and observe degree of dissolution. If article sample contains no solid pieces after the 2 additional strokes, record number of strokes=4 Dissolution Strokes. If after the 4 strokes total, the article sample still contains solid pieces of un-dissolved article sample, continue rubbing remaining article sample in additional 2 circular strokes and check if there are any remaining solid pieces of article sample after each additional 2 strokes until article sample is completely dissolved or until reaching a total of 30 strokes, whichever comes first. Record the total number of strokes. Record 30 Dissolution Strokes even if solid article sample pieces remain after the maximum of 30 strokes.

Repeat this process for each of the additional 4 article samples.

Calculate the arithmetic mean of the recorded values of Dissolution Strokes for the 5 individual article samples and record as the Average Hand Dissolution Value for the article. The Average Hand Dissolution Value is reported to the nearest single Dissolution Stroke unit.

The invention of the disclosure can be described by any of the following paragraphs:

An article having one or more fibrous elements wherein at least one of the fibrous elements includes one or more filament-forming materials and one or more active agents releasable from the fibrous elements, wherein the article exhibits an Average Inter-Ply Peak Peel Force of greater than 0.03 N as measured according to the Inter-Ply, Intra-Ply, and Whole 180° Peel Test Method, wherein the article has one or more of a width from about 1 cm to about 11 cm; a length from about 1 cm to about 20 cm; a height from about 0.01 mm to about 50.0 mm; a mass from about 0.25 g to about 40 g; a volume from about 0.25 cc to about 60 cc; and a density from about 0.05 g/cc to about 0.8 g/cc.

An article having one or more fibrous elements wherein at least one of the fibrous elements includes one or more filament-forming materials and one or more active agents releasable from the fibrous elements, wherein the article exhibits an Average Intra-Ply Peak Peel Force of greater than 0.10 N as measured according to the Inter-Ply, Intra-Ply, and Whole 180° Peel Test Method, wherein the article has one or more of a width from about 1 cm to about 11 cm; a length from about 1 cm to about 20 cm; a height from about 0.01 mm to about 50.0 mm; a mass from about 0.25 g to about 40 g; a volume from about 0.25 cc to about 60 cc; and a density from about 0.05 g/cc to about 0.8 g/cc.

An article having one or more fibrous elements wherein at least one of the fibrous elements includes one or more filament-forming materials and one or more active agents releasable from the fibrous elements, wherein the article exhibits an Average Whole 180° Peak Peel Force of greater than 0.03 N as measured according to the Inter-Ply, Intra-Ply, and Whole 180° Peel Test Method, wherein the article has one or more of a width from about 1 cm to about 11 cm; a length from about 1 cm to about 20 cm; a height from about 0.01 mm to about 50.0 mm; a mass from about 0.25 g to about 40 g; a volume from about 0.25 cc to about 60 cc; and a density from about 0.05 g/cc to about 0.8 g/cc.

A multi-ply article having a first ply and a second ply, wherein at least one of the first and second plies includes an article including one or more filaments wherein at least one of the filaments includes one or more filament-forming materials and one or more active agents releasable from the filament, wherein the article exhibits an Average Inter-Ply Peak Peel Force of greater than 0.03 N as measured according to the Inter-Ply, Intra-Ply, and Whole 180° Peel Test Method, wherein the article has one or more of a width from about 1 cm to about 11 cm; a length from about 1 cm to about 20 cm; a height from about 0.01 mm to about 50.0 mm; a mass from about 0.25 g to about 40 g; a volume from about 0.25 cc to about 60 cc; and a density from about 0.05 g/cc to about 0.8 g/cc.

A multi-ply article having a first ply and a second ply, wherein at least one of the first and second plies includes an article including one or more filaments wherein at least one of the filaments includes one or more filament-forming materials and one or more active agents releasable from the filament, wherein the article exhibits an Average Intra-Ply Peak Peel Force of greater than 0.10 N as measured according to the Inter-Ply, Intra-Ply, and Whole 180° Peel Test Method, wherein the article has one or more of a width from about 1 cm to about 11 cm; a length from about 1 cm to about 20 cm; a height from about 0.01 mm to about 50.0 mm; a mass from about 0.25 g to about 40 g; a volume from about 0.25 cc to about 60 cc; and a density from about 0.05 g/cc to about 0.8 g/cc.

A multi-ply article having a first ply and a second ply, wherein at least one of the first and second plies includes an article including one or more filaments wherein at least one of the filaments includes one or more filament-forming materials and one or more active agents releasable from the filament, wherein the article exhibits an Average Whole 180° Peak Peel Force of greater than 0.03 N as measured according to the Inter-Ply, Intra-Ply, and Whole 180° Peel Test Method, wherein the article has one or more of a width from about 1 cm to about 11 cm; a length from about 1 cm to about 20 cm; a height from about 0.01 mm to about 50.0 mm; a mass from about 0.25 g to about 40 g; a volume from about 0.25 cc to about 60 cc; and a density from about 0.05 g/cc to about 0.8 g/cc.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular examples of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A multi-ply water-soluble article comprising two or more plies, wherein the two or more plies are bonded to each other to form the multi-ply water-soluble article, wherein at least one of the two or more plies comprises a water-soluble fibrous structure comprising one or more water-soluble fibrous elements wherein at least one of the water-soluble fibrous elements comprises one or more filament-forming materials and one or more active agents releasable from the water-soluble fibrous elements;
  wherein the multi-ply water-soluble article exhibits an Average Inter-Ply Peak Peel Force of greater than 0.03 N to about 5.00 N as measured according to the Inter-Ply, Intra-Ply, and Whole 180° Peel Test Method, such that the multi-ply water-soluble article exhibits an Average Hand Dissolution Value of less than 30 Dissolution Strokes to greater than 0 Dissolution Strokes as measured according to the Hand Dissolution Test Method, an Average Maximum Peak Force of less than 20.00 N as measured according to the Modified Circular Bend Test Method, and an Average Bending Stiffness of less than 2500.0 N/m as measured according to the Modified Circular Bend Test Method;
    wherein the multi-ply water-soluble article has one or more of:
      a width from about 1 cm to about 11 cm;
      a length from about 1 cm to about 20 cm;
      a height from about 0.01 mm to about 50 mm;
      a mass from about 0.25 g to about 50 g;
      a volume from about 0.25 cc to about 60 cc; and
      a density from about 0.05 g/cc to about 0.8 g/cc.

2. The multi-ply water-soluble article according to claim 1 wherein the one or more active agents comprises one or more effervescent agents.

3. The multi-ply water-soluble article according to claim 1 comprising about 30% or more of one or more active agents.

4. The multi-ply water-soluble article according to claim 1 wherein the multi-ply water-soluble article exhibits an average disintegration time of less than 360 seconds as measured according to the Dissolution Test Method.

5. The multi-ply water-soluble article according to claim 1 wherein the multi-ply water-soluble article exhibits an average dissolution time of less than 3600 seconds as measured according to the Dissolution Test Method.

6. The multi-ply water-soluble article according to claim 1 wherein the multi-ply water-soluble article exhibits Average Hand Dissolution Value of less than 29 dissolution strokes as measured according to the Hand Dissolution Test Method.

7. The multi-ply water-soluble article according to claim 1 wherein the multi-ply water-soluble article further comprises a plurality of particles.

8. The multi-ply water-soluble article according to claim 7 wherein the plurality of particles are positioned between at least two of the two or more plies.

9. The multi-ply water-soluble article according to claim 7 wherein at least one of the plurality of particles comprises an active agent-containing particle.

10. A multi-ply water-soluble article comprising two or more plies, wherein the two or more plies are bonded to each other to form the multi-ply water-soluble article, wherein at least one of the two or more plies comprises a water-soluble fibrous structure comprising one or more water-soluble fibrous elements wherein at least one of the water-soluble fibrous elements comprises one or more filament-forming materials and one or more active agents releasable from the water-soluble fibrous elements;
  wherein the multi-ply water-soluble article exhibits an Average Intra-Ply Peak Peel Force of greater than 0.10 N to about 5.00 N as measured according to the Inter-Ply, Intra-Ply, and Whole 180° Peel Test Method, such that the multi-ply water-soluble article exhibits an Average Hand Dissolution Value of less than 30 Dissolution Strokes to greater than 0 Dissolution Strokes as measured according to the Hand Dissolution Test Method, an Average Maximum Peak Force of less than 20.00 N as measured according to the Modified Circular Bend Test Method, and an Average Bending Stiffness of less than 2500.0 N/m as measured according to the Modified Circular Bend Test Method;
    wherein the multi-ply water-soluble article has one or more of:
      a width from about 1 cm to about 11 cm;
      a length from about 1 cm to about 20 cm;
      a height from about 0.01 mm to about 50 mm;
      a mass from about 0.25 g to about 50 g;
      a volume from about 0.25 cc to about 60 cc; and
      a density from about 0.05 g/cc to about 0.8 g/cc.

11. The multi-ply water-soluble article according to claim 10 wherein the one or more active agents comprises one or more effervescent agents.

12. The multi-ply water-soluble article according to claim 10 comprising about 30% or more of one or more active agents.

13. The multi-ply water-soluble article according to claim 10 wherein the multi-ply water-soluble article exhibits an average disintegration time of less than 360 seconds as measured according to the Dissolution Test Method.

14. The multi-ply water-soluble article according to claim 10 wherein the multi-ply water-soluble article exhibits an average dissolution time of less than 3600 seconds as measured according to the Dissolution Test Method.

15. The multi-ply water-soluble article according to claim 10 wherein the multi-ply water-soluble article exhibits Average Hand Dissolution Value of less than 29 dissolution strokes as measured according to the Hand Dissolution Test Method.

16. The multi-ply water-soluble article according to claim 10 wherein the multi-ply water-soluble article further comprises a plurality of particles.

17. The multi-ply water-soluble article according to claim 16 wherein the plurality of particles are positioned between at least two of the two or more plies.

18. The multi-ply water-soluble article according to claim 16 wherein at least one of the plurality of particles comprises an active agent-containing particle.

19. A multi-ply water-soluble article comprising two or more plies, wherein the two or more plies are bonded to each other to form the multi-ply water-soluble article, wherein at least one of the two or more plies comprises a water-soluble fibrous structure comprising one or more water-soluble fibrous elements wherein at least one of the water-soluble fibrous elements comprises one or more filament-forming materials and one or more active agents releasable from the water-soluble fibrous elements;
  wherein the multi-ply water-soluble article exhibits an Average Whole 180° Peak Peel Force of greater than 0.03 N to about 5.00 N as measured according to the Inter-Ply, Intra-Ply, and Whole 180° Peel Test Method, such that the multi-ply water-soluble article exhibits an Average Hand Dissolution Value of less than 30 Dissolution Strokes to greater than 0 Dissolution Strokes as measured according to the Hand Dissolution Test Method, an Average Maximum Peak Force of less than 20.00 N as measured according to the Modified Circular Bend Test Method, and an Average Bending Stiffness of less than 2500.0 N/m as measured according to the Modified Circular Bend Test Method;

wherein the multi-ply water-soluble article has one or more of:
a width from about 1 cm to about 11 cm;
a length from about 1 cm to about 20 cm;
a height from about 0.01 mm to about 50 mm;
a mass from about 0.25 g to about 50 g;
a volume from about 0.25 cc to about 60 cc; and
a density from about 0.05 g/cc to about 0.8 g/cc.

20. The multi-ply water-soluble article according to claim 19 wherein the multi-ply water-soluble article exhibits an average disintegration time of less than 360 seconds as measured according to the Dissolution Test Method.

21. The multi-ply water-soluble article according to claim 19 wherein the one or more active agents comprises one or more effervescent agents.

22. The multi-ply water-soluble article according to claim 19 comprising about 30% or more of one or more active agents.

23. The multi-ply water-soluble article according to claim 19 wherein the multi-ply water-soluble article exhibits an average dissolution time of less than 3600 seconds as measured according to the Dissolution Test Method.

24. The multi-ply water-soluble article according to claim 19 wherein the multi-ply water-soluble article further comprises a plurality of particles.

25. The multi-ply water-soluble article according to claim 24 wherein the plurality of particles are positioned between at least two of the two or more plies.

26. The multi-ply water-soluble article according to claim 24 wherein at least one of the plurality of particles comprises an active agent-containing particle.

* * * * *